(12) United States Patent
Watanabe et al.

(10) Patent No.: US 7,825,146 B2
(45) Date of Patent: Nov. 2, 2010

(54) SULFONAMIDE DERIVATIVE HAVING ISOXAZOLE RING

(75) Inventors: Fumihiko Watanabe, Osaka (JP); Naoki Yoshikawa, Osaka (JP); Yoshinori Tamura, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 1315 days.

(21) Appl. No.: 10/565,948

(22) PCT Filed: Jul. 28, 2004

(86) PCT No.: PCT/JP2004/010697

§ 371 (c)(1),
(2), (4) Date: Jan. 26, 2006

(87) PCT Pub. No.: WO2005/012268

PCT Pub. Date: Feb. 10, 2005

(65) Prior Publication Data

US 2006/0183770 A1    Aug. 17, 2006

(30) Foreign Application Priority Data

Jul. 30, 2003    (JP) .............................. 2003-282354

(51) Int. Cl.
*A61K 31/422*    (2006.01)

(52) U.S. Cl. ...................... 514/378; 548/247; 549/440; 549/496

(58) Field of Classification Search ................. 546/172, 546/329, 334; 548/247; 549/74, 442, 443, 549/496, 440; 514/378
See application file for complete search history.

(56) References Cited

U.S. PATENT DOCUMENTS

| 2003/0203940 A1 | 10/2003 | Yoshika et al. |
| 2004/0024029 A1 | 2/2004 | Watanabe et al. |

FOREIGN PATENT DOCUMENTS

| EP | 0 950 656 A1 | 1/1999 |
| EP | 1 029 541 | 8/2000 |
| EP | 1 172 361 | 1/2002 |
| WO | 97/27174 | 7/1997 |
| WO | 99/04780 | 2/1999 |
| WO | 00/63194 A1 | 10/2000 |
| WO | 01/83431 A1 | 11/2001 |
| WO | 01/83461 A1 | 11/2001 |
| WO | 01/83463 | 11/2001 |
| WO | 01/83464 A1 | 11/2001 |
| WO | 02/28844 A1 | 4/2002 |

*Primary Examiner*—Janet L Andres
*Assistant Examiner*—David E Gallis
(74) *Attorney, Agent, or Firm*—Hamre, Schumann, Mueller & Larson, P.C.

(57) ABSTRACT

A compound represented by the general formula (I-A):

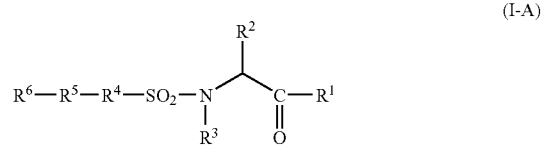

(I-A)

wherein $R^1$ is hydroxy and the like; $R^2$ is optionally substituted lower alkyl and the like; $R^3$ is hydrogen atom and the like; $R^4$ is optionally substituted arylene and the like; $R^5$ is a group represented by the formula:

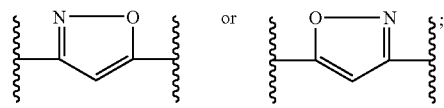

$R^6$ is optionally substituted aryl and the like, its optically active substance, their pharmaceutically acceptable salt, or a solvate thereof; and a metalloproteinase inhibitor containing them.

13 Claims, No Drawings ial
SULFONAMIDE DERIVATIVE HAVING ISOXAZOLE RING

TECHNICAL FIELD

This invention relates to sulfonamide derivatives having an isoxazole ring and metalloproteinase inhibitors containing the same.

BACKGROUND ART

An extracellular matrix, consisting of collagen, fibronectin, laminin, proteoglycan, etc., has a function to support tissues, and plays a role in propagation, differentiation, adhesion, and the like in cells. Metalloproteinases which are protease having a metal ion in the active center, especially matrix metalloproteinases (MMP), are concerned with the degradation of the extracellular matrix. Many types of MMP, from MMP-1 (collagenase type I) to MMP-23, have been reported as enzymes working for the growth, remodeling of tissues, etc. under usual physiological conditions. It is reported, however, that the progression of various kinds of diseases involving breakdown and fibrosis of tissues (e.g., osteoarthritis, rheumatoid arthritis, corneal ulceration, periodontitis, metastasis and invasion of tumor, and virus infection (HIV infection)) is related with increase of the manifestation or activity of the above-mentioned enzyme.

Sulfonamide derivatives having an inhibitory activity against MMP are described in Patent Document 1, Non Patent Document 1, and the like.

Sulfonamide derivatives having an oxazole ring, a thiazole ring, or an oxadiazole ring are described in Patent Documents 2 to 7.

Patent Document 1: International Publication WO 97/27174
Patent Document 2: International Publication WO 99/04780
Patent Document 3: International Publication WO 01/83461
Patent Document 4: International Publication WO 02/28844
Patent Document 5: International Publication WO 01/83463
Patent Document 6: International Publication WO 01/83464
Patent Document 7: International Publication WO 00/63194
Non Patent Document 1: Tamura Y., et al., J. Med. Chem., 41(4), 640-649, 1998.

DISCLOSURE OF INVENTION

Problems to be Solved by the Invention

It is considered that MMP inhibitors contribute to the treatment or prevention of the above-mentioned diseases caused by or related to the MMP activities. Therefore, the development of MMP inhibitors has been desired.

Means to Solve the Problems

In the above situation, the inventors of the present invention have found that certain sulfonamide derivatives having an isoxazole ring have a potent inhibitory activity against MMP, and have accomplished the present invention.

The present invention relates to 1) A compound represented by the formula (I):

$$R^6—R^5—R^4—SO_2—W \qquad (I)$$

wherein W is a group represented by the formula:

[chemical structures]

wherein $R^1$ is NHOH, hydroxy, or lower alkyloxy;
$R^2$ and $R^{2'}$ are each independently hydrogen atom, optionally substituted lower alkyl, optionally substituted aryl, optionally substituted aralkyl, optionally substituted heteroaryl, or optionally substituted heteroarylalkyl;
$R^3$ is hydrogen atom, optionally substituted lower alkyl, optionally substituted aryl, optionally substituted aralkyl, optionally substituted heteroaryl, or optionally substituted heteroarylalkyl;
$Z^1$ is $—CH_2—$, $—NH—$, $—O—$, or $—S—$;
a broken line ( - - - ) represents the presence or absence of a bond;
$R^4$ is optionally substituted arylene or optionally substituted heteroarylene;
$R^5$ is a group represented by the formula:

[chemical structures]

$R^6$ is optionally substituted aryl, optionally substituted heteroaryl, optionally substituted cycloalkyl, or optionally substituted non-aromatic heterocyclic groups;

its optically active substance, their pharmaceutically acceptable salt, or a solvate thereof.

In more detail, the invention relates to the following 2) to 20).
2) A compound described in 1) wherein W is a group represented by the formula:

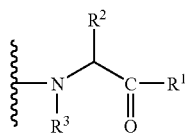

wherein $R^1$, $R^2$, and $R^3$ are as defined in 1), its optically active substance, their pharmaceutically acceptable salt, or a solvate thereof.

3) A compound described in 1) or 2) wherein $R^6$ is a group represented by the formula:

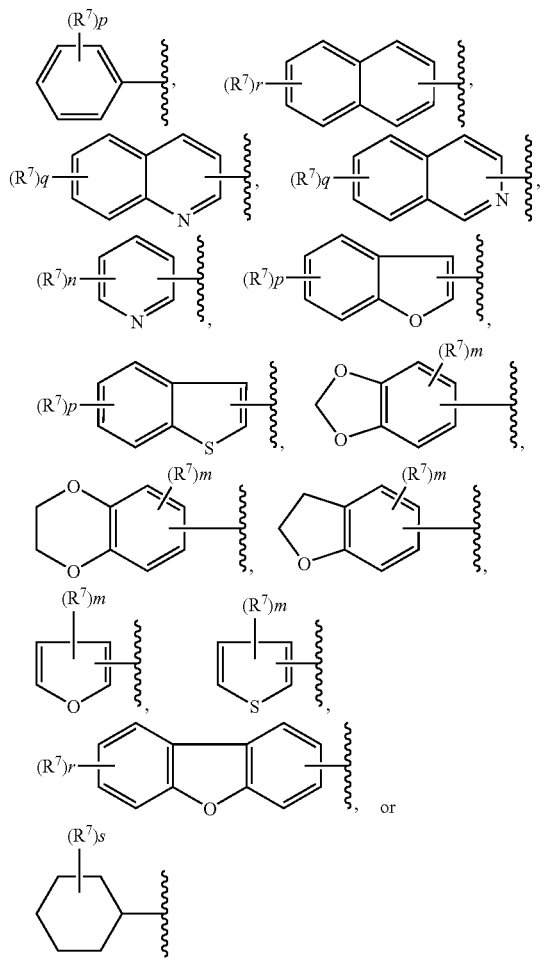

wherein $R^7$ is each independently halogen, lower alkyl, cycloalkyl, lower alkenyl, lower alkynyl, lower alkyloxy, lower alkenyloxy, lower alkylthio, halo(lower)alkyl, halo(lower)alkyloxy, halo(lower)alkylthio, hydroxy, hydroxy(lower)alkyl, carboxy, lower alkyloxycarbonyl, lower alkylsulfonyl, carbamoyl, acyl, acyloxy, nitro, cyano, optionally substituted amino, or optionally substituted aminocarbonyl; m is an integer from 0 to 3; n is an integer from 0 to 4; p is an integer from 0 to 5; q is an integer from 0 to 6; r is an integer from 0 to 7; s is an integer from 0 to 11, its optically active substance, their pharmaceutically acceptable salt, or a solvate thereof.

Wherein a cyclic substituent for $R^6$ as above may be substituted with $R^7$ at any possible position. And the cyclic substituent as above may be substituted with $R^7$ at any possible position.

4) A compound described in any one of 1) to 3) wherein $R^1$ is hydroxy, its optically active substance, their pharmaceutically acceptable salt, or a solvate thereof.

5) A compound described in any one of 1) to 4) wherein $R^2$ and $R^{2'}$ are each independently selected from lower alkyl optionally, substituted by halogen, hydroxy, carboxy, carbamoyl, mercapto, lower alkylthio, guanidino, amino, or cycloalkyl; aryl optionally substituted by hydroxy; aralkyl optionally substituted by halogen, hydroxy, or nitro; heteroaryl optionally substituted by hydroxy; heteroarylalkyl optionally substituted by hydroxy; or hydrogen atom, its optically active substance, their pharmaceutically acceptable salt, or a solvate thereof.

6) A compound described in 5) wherein $R^2$ and $R^{2'}$ are each independently selected from hydrogen atom, methyl, isopropyl, s-butyl, isobutyl, t-butyl, hydroxymethyl, 1-hydroxyethyl, 2-hydroxyethyl, carboxymethyl, carboxyethyl, carbamoylmethyl, carbamoylethyl, mercaptomethyl, 2-methylthioethyl, cyclohexylmethyl, 3-guanidinopropyl, 4-aminobutyl, phenyl, 4-hydroxyphenyl, benzyl, 4-hydroxybenzyl, 4-fluorobenzyl, 4-chlorobenzyl, 4-bromobenzyl, 4-nitrobenzyl, phenylethyl, 1-naphthylmethyl, 2-naphthylmethyl, biphenylmethyl, indolyl, thienyl, indol-3-ylmethyl, (5-hydroxyindol-3-yl)methyl, thiophen-2-ylmethyl, imidazolylmethyl, benzoxazol-2-ylmethyl, benzthiazol-2-ylmethyl, or benzimidazol-2-ylmethyl, its optically active substance, their pharmaceutically acceptable salt, or a solvate thereof.

7) A compound described in any one of 1) to 6) wherein $R^3$ is hydrogen atom, its optically active substance, their pharmaceutically acceptable salt, or a solvate thereof.

8) A compound described in any one of 1) to 7) wherein $R^4$ is 1,4-phenylene or 2,5-thiophendiyl, its optically active substance, their pharmaceutically acceptable salt, or a solvate thereof.

9) A compound described in any one of 1) to 8) wherein $R^6$ is a group represented by the formula:

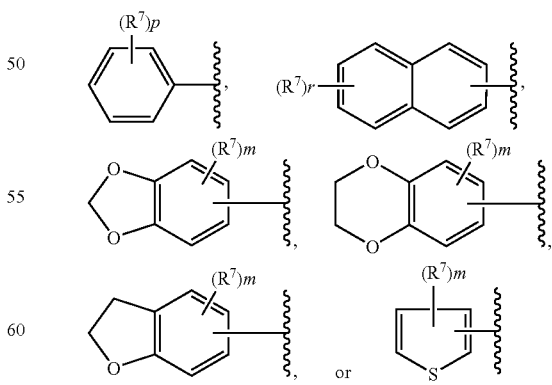

wherein $R^7$, m, p, and r are as defined in 3), its optically active substance, their pharmaceutically acceptable salt, or a solvate thereof.

10) A compound represented by the general formula (II-A):

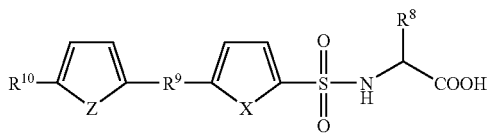

(II-A)

wherein $R^8$ is hydrogen atom, methyl, isopropyl, s-butyl, isobutyl, t-butyl, hydroxymethyl, 1-hydroxyethyl, 2-hydroxyethyl, carboxymethyl, carboxyethyl, 2-methylthioethyl, phenyl, 4-hydroxyphenyl, benzyl, 4-hydroxybenzyl, or indol-3-ylmethyl;
X is —CH=CH— or —S—;
$R^9$ is a group represented by the formula:

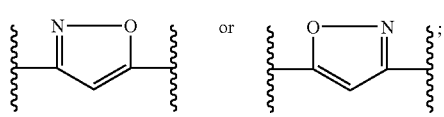

Z is —CH=CH— or —S—;
$R^{10}$ is hydrogen atom, halogen, lower alkyl, lower alkyloxy, lower alkylthio, halo(lower)alkyl, halo(lower)alkyloxy, halo(lower)alkylthio, hydroxy, hydroxy(lower)alkyl, acyl, nitro, cyano, or optionally substituted amino, its optically active substance, their pharmaceutically acceptable salt, or a solvate thereof.

11) A compound represented by the general formula (II-B):

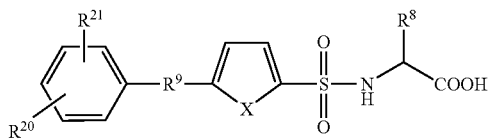

(II-B)

wherein $R^8$ is hydrogen atom, methyl, isopropyl, s-butyl, isobutyl, t-butyl, hydroxymethyl, 1-hydroxyethyl, 2-hydroxyethyl, carboxymethyl, carboxyethyl, 2-methylthioethyl, phenyl, 4-hydroxyphenyl, benzyl, 4-hydroxybenzyl, or indol-3-ylmethyl;
X is —CH=CH— or —S—;
$R^9$ is a group represented by the formula:

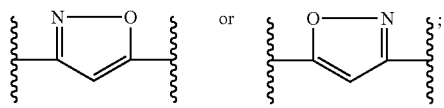

$R^{20}$ and $R^{21}$ are each independently hydrogen atom, halogen, lower alkyl, lower alkyloxy, lower alkylthio, halo(lower)alkyl, halo(lower) alkyloxy, halo(lower)alkylthio, hydroxy, hydroxy(lower)alkyl, acyl, nitro, cyano, or optionally substituted amino; or $R^{20}$ and $R^{21}$ are taken together to form a group represented by the formula: —CH=CH—CH=CH—, —O—CH$_2$—O—, —O—CH$_2$—CH$_2$—O—, —CH$_2$—CH$_2$—O—, or —O—CH$_2$—CH$_2$— when the carbon atom bonded to $R^{20}$ is adjacent to the carbon atom bonded to $R^{21}$, its optically active substance, their pharmaceutically acceptable salt, or a solvate thereof.

12) A compound represented by the general formula (II-C):

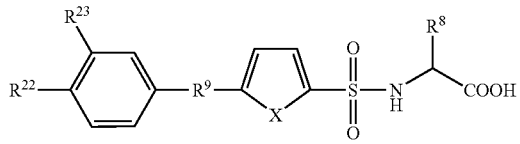

(II-C)

wherein $R^8$ is hydrogen atom, methyl, isopropyl, s-butyl, isobutyl, t-butyl, hydroxymethyl, 1-hydroxyethyl, 2-hydroxyethyl, carboxymethyl, carboxyethyl, 2-methylthioethyl, phenyl, 4-hydroxyphenyl, benzyl, 4-hydroxybenzyl, or indol-3-ylmethyl;
X is —CH=CH— or —S—;
$R^9$ is a group represented by the formula:

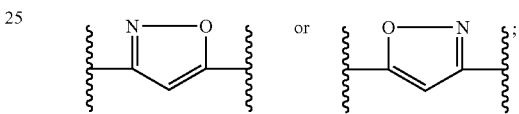

$R^{22}$ and $R^{23}$ are each independently hydrogen atom, halogen, lower alkyl, lower alkyloxy, lower alkylthio, halo(lower)alkyl, halo(lower)alkyloxy, halo(lower)alkylthio, hydroxy, hydroxy(lower)alkyl, acyl, nitro, cyano, or optionally substituted amino, its optically active substance, their pharmaceutically acceptable salt, or a solvate thereof.

13) A compound represented by the general formula (II-D):

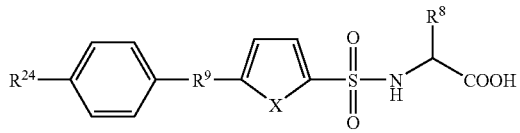

(II-D)

wherein $R^8$ is hydrogen atom, methyl, isopropyl, s-butyl, isobutyl, t-butyl, hydroxymethyl, 1-hydroxyethyl, 2-hydroxyethyl, carboxymethyl, carboxyethyl, 2-methylthioethyl, phenyl, 4-hydroxyphenyl, benzyl, 4-hydroxybenzyl, or indol-3-ylmethyl;
X is —CH=CH— or —S—;
$R^9$ is a group represented by the formula:

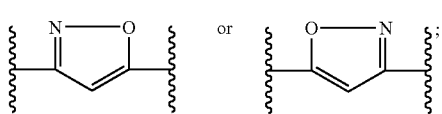

$R^{24}$ is hydrogen atom, halogen, lower alkyl, lower alkyloxy, lower alkylthio, halo(lower)alkyl, halo(lower)alkyloxy, halo(lower)alkylthio, hydroxy, hydroxy(lower)alkyl, acyl, nitro, cyano, or optionally substituted amino, its optically active substance, their pharmaceutically acceptable salt, or a solvate thereof.

14) A compound represented by the general formula (II-E):

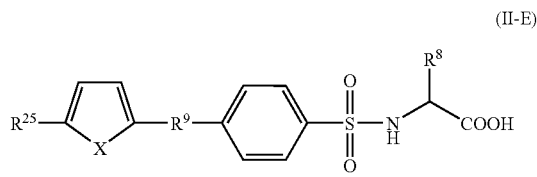

(II-E)

wherein $R^8$ is hydrogen atom, methyl, isopropyl, s-butyl, isobutyl, t-butyl, hydroxymethyl, 1-hydroxyethyl, 2-hydroxyethyl, carboxymethyl, carboxyethyl, 2-methylthioethyl, phenyl, 4-hydroxyphenyl, benzyl, 4-hydroxybenzyl, or indol-3-ylmethyl;

$R^9$ is a group represented by the formula:

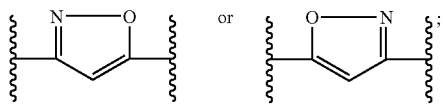

X is —CH=CH— or —S—;

$R^{25}$ is hydrogen atom, halogen, lower alkyl, lower alkyloxy, lower alkylthio, halo(lower)alkyl, halo(lower)alkyloxy, halo(lower)alkylthio, hydroxy, hydroxy(lower)alkyl, acyl, nitro, cyano, or optionally substituted amino, its optically active substance, their pharmaceutically acceptable salt, or a solvate thereof.

15) A compound described in any one of 10) to 14) wherein $R^8$ is isopropyl, s-butyl, or isobutyl, its optically active substance, their pharmaceutically acceptable salt, or a solvate thereof.

16) A pharmaceutical composition which contains a compound described in any one of 1) to 15) as an active ingredient.

17) A metalloproteinase inhibitor which contains a compound described in any one of 1) to 15) as an active ingredient.

18) A matrix metalloproteinase inhibitor which contains a compound described in any one of 1) to 15) as an active ingredient.

19) Use of a compound described in any one of 1) to 15) for the preparation of a medicament for treating a disease caused by or related to metalloproteinase.

20) A method for treating a disease caused by or related to metalloproteinase of a mammal comprising administering to said mammal including human a therapeutically effective amount of a compound described in any one of 1) to 15).

In the present specification, the term "lower alkyl" employed alone or in combination with other terms means a straight- or branched chain monovalent hydrocarbon group having 1 to 8 carbon atom(s). Examples of the alkyl include methyl, ethyl, n-propyl, isopropyl, n-butyl, isobutyl, sec-butyl, tert-butyl, n-pentyl, isopentyl, neo-pentyl, n-hexyl, isohexyl, n-heptyl, n-octyl and the like. $C_1$ to $C_6$ alkyl is preferred. $C_1$ to $C_3$ alkyl is more preferred.

In the present specification, the term "cycloalkyl" includes cycloalkyl group having 3 to 8 carbon atoms. Examples of cycloalkyl group include cyclopropyl, cyclobutyl, cyclopentyl, cyclohexyl, cycloheptyl, cyclooctyl and the like. $C_3$ to $C_6$ cycloalkyl is preferred.

In the present specification, the term "lower alkenyl" employed alone or in combination with other terms means a straight- or branched chain monovalent hydrocarbon group having 2 to 8 carbon atoms and at least one double bond. Examples of the alkenyl include vinyl, allyl, propenyl, crotonyl, isopentenyl, a variety of butenyl isomers and the like. $C_2$ to $C_6$ alkenyl is preferred. $C_2$ to $C_4$ alkenyl is more preferred.

In the present specification, the term "lower alkynyl" means a straight- or branched chain monovalent hydrocarbon group having 2 to 8 carbon atoms and at least one triple bond. The alkynyl may contain (a) double bond(s). Examples of the alkynyl include ethynyl, 2-propynyl, 3-butynyl, 4-pentynyl, 5-hexynyl, 6-heptynyl, 7-octynyl and the like. $C_2$ to $C_6$ alkynyl is preferred. $C_2$ to $C_4$ alkynyl is more preferred.

In the present specification, the term "aryl" employed alone or in combination with other terms includes monocyclic or condensed ring aromatic hydrocarbons, or an aromatic hydrocarbon containing continuously bonded two or three of the aromatic rings. Examples of the aryl include phenyl, 1-naphthyl, 2-naphthyl, anthryl, 4-biphenyl and the like.

Preferable is phenyl as "aryl" for $R^2$ and $R^{2'}$.

Preferable is phenyl as "aryl" for $R^3$.

Preferable are phenyl, 1-naphthyl, and 2-naphthyl as "aryl" for $R^6$.

In the present specification, the term "aralkyl" herein used means the above mentioned "lower alkyl" substituted one or more with the above mentioned "aryl" at any possible position. Examples of the aralkyl are benzyl, phenylethyl (e.g., 2-phenylethyl), phenylpropyl (e.g., 3-phenylpropyl), naphthylmethyl (e.g., 1-naphthylmethyl and 2-naphthylmethyl), anthrylmethyl (e.g., 9-anthrylmethyl), biphenylmethyl (e.g., 4-biphenylmethyl), and the like. Benzyl and phenylethyl are preferred.

Preferable are benzyl, phenylethyl, 1-naphthylmethyl, 2-naphthylmethyl, and 4-biphenylmethyl as "aralkyl" for $R^2$ and $R^{2'}$.

Preferable is phenyl $C_1$ to $C_3$ alkyl as "aralkyl" for $R^3$. Benzyl is more preferable.

In the present specification, the term "heteroaryl" employed alone or in combination with other terms includes a 5 to 6 membered aromatic heterocyclic group which contains one or more hetero atoms selected from the group consisting of oxygen, sulfur, and nitrogen atoms in the ring and may be fused with cycloalkyl, aryl, non-aromatic heterocyclic group, and other heteroaryl at any possible position. Examples of the heteroaryl are pyrrolyl (e.g., 1-pyrrolyl, 2-pyrrolyl, 3-pyrrolyl), furyl (e.g., 2-furyl, 3-furyl), thienyl (e.g., 2-thienyl, 3-thienyl), imidazolyl (e.g., 2-imidazolyl, 4-imidazolyl), pyrazolyl (e.g., 1-pyrazolyl, 3-pyrazolyl), isothiazolyl (e.g., 3-isothiazolyl), isoxazolyl (e.g., 3-isoxazolyl), oxazolyl (e.g., 2-oxazolyl), thiazolyl (e.g., 2-thiazolyl), pyridyl (e.g., 2-pyridyl, 3-pyridyl, 4-pyridyl), pyrazinyl (e.g., 2-pyrazinyl), pyrimidinyl (e.g., 2-pyrimidinyl, 4-pyrimidinyl), pyridazinyl (e.g., 3-pyridazinyl), tetrazolyl (e.g., 1H-tetrazolyl), oxadiazolyl (e.g., 1,3,4-oxadiazolyl), thiadiazolyl (e.g., 1,3,4-thiadiazolyl), indolizinyl (e.g., 2-indolizinyl, 6-indolizinyl), isoindolyl (e.g., 2-isoindolyl), indolyl (e.g., 1-indolyl, 2-indolyl, 3-indolyl), indazolyl (e.g., 3-indazolyl), purinyl (e.g., 8-purinyl), quinolizinyl (e.g., 2-quinolizinyl), isoquinolyl (e.g., 3-isoquinolyl), quinolyl (e.g., 2-quinolyl, 5-quinolyl), phthalazinyl (e.g., 1-phthalazinyl), naphthyridinyl (e.g., 2-naphthyridinyl), quinoxanyl (e.g., 2-quinoxanyl), quinazolinyl (e.g., 2-quinazolinyl), cinnolinyl (e.g., 3-cinnolinyl), pteridinyl (e.g., 2-pteridinyl), carbazolyl (e.g., 2-carbazolyl, 3-carbazolyl), phenanthridinyl (e.g., 2-phenanthridinyl, 3-phenanthridinyl), acridinyl (e.g., 1-acridinyl, 2-acridinyl), dibenzofuranyl (e.g., 1-dibenzofuranyl, 2-dibenzofuranyl), benzimidazolyl (e.g., 2-benzimidazolyl), benzisoxazolyl (e.g., 3-benzisoxazolyl), benzoxazolyl (e.g., 2-benzoxazolyl), benzoxadiazolyl (e.g., 4-benzoxadiazolyl), benzisothiazolyl (e.g., 3-benzisothiazolyl), benzothiazolyl (e.g., 2-benzothiazolyl), benzofuryl (e.g., 3-benzofuryl), benzothienyl (e.g., 2-benzothienyl) and the like.

Preferable are indolyl, imidazolyl, furyl, thienyl, and the like as "heteroaryl" for $R^2$ and $R^{2'}$.

Preferable are pyridyl, thienyl, furyl, imidazolyl, and the like as "heteroaryl" for $R^3$.

Preferable are quinolyl (e.g., 2-quinolyl), isoquinolyl (e.g., 1-isoquinolyl, 3-isoquinolyl), pyridyl (e.g., 3-pyridyl), benzofuranyl (e.g., 2-benzofuranyl), benzothienyl (e.g., 2-benzothienyl), dibenzofuranyl, thienyl (e.g., 2-thienyl), furyl (e.g., 2-furyl), and the like as "heteroaryl" for $R^6$.

In the present specification, the term "heteroarylalkyl" herein used includes the above mentioned "lower alkyl" substituted one or more with the above mentioned "heteroaryl" at any possible position.

Examples of the heteroarylalkyl are oxazolylmethyl (e.g., 2-oxazolylmethyl, 4-oxazolylmethyl), thiazolylmethyl (e.g., 2-thiazolylmethyl, 4-thiazolylmethyl), oxazolylethyl (e.g., 5-oxazolyl-2-ethyl), thiazolylethyl (e.g., 5-thiazolyl-2-ethyl), benzoxazolylmethyl (e.g., benzoxazol-2-ylmethyl), benzothiazolylmethyl (e.g., benzothiazol-2-ylmethyl), indolylmethyl (e.g., indol-3-ylmethyl), imidazolylmethyl (e.g., 4-imidazolylmethyl), indazolylmethyl (e.g., 1-indazolylmethyl), benzotriazolylmethyl (e.g., 1-benzotriazolylmethyl), benzoquinolylmethyl (e.g., 2-benzoquinolylmethyl), benzimidazolylmethyl (e.g., benzimidazol-2-ylmethyl), pyridylmethyl (e.g., 4-pyridylmethyl), furylmethyl (e.g., furan-2-ylmethyl), thienylmethyl (e.g., thiophen-2-ylmethyl) and the like.

Preferable are indolylmethyl (e.g., indol-3-ylmethyl), imidazolylmethyl (e.g., imidazol-5-ylmethyl), benzoxazolylmethyl (e.g., benzoxazol-2-ylmethyl), benzothiazolylmethyl (e.g., benzothiazol-2-ylmethyl), benzimidazolylmethyl (e.g., benzimidazol-2-ylmethyl), thienylmethyl (e.g., thiophen-2-ylmethyl), thiazolylmethyl (e.g., 2-thiazolylmethyl, 4-thiazolylmethyl) and the like as "heteroarylalkyl" for $R^2$ and $R^{2'}$.

Preferable are indolylmethyl (e.g., indol-3-ylmethyl), imidazolylmethyl (e.g., imidazol-5-ylmethyl), thienylmethyl (e.g., thiophen-2-ylmethyl), thiazolylmethyl (e.g., 2-thiazolylmethyl, 4-thiazolylmethyl) and the like as "heteroarylalkyl" for $R^3$.

In the present specification, the term "non-aromatic heterocyclic group" employed alone or in combination with other terms includes a 5 to 7 membered non-aromatic ring which contains one or more hetero atoms selected from the group consisting of oxygen, sulfur, and nitrogen atoms in the ring and a condensed ring which are formed with two or more of the non-aromatic ring. Examples of the non-aromatic heterocyclic group are pyrrolidinyl (e.g., 1-pyrrolidinyl, 2-pyrrolidinyl), pyrrolinyl (e.g., 3-pyrrolinyl), imidazolidinyl (e.g., 2-imidazolidinyl), imidazolinyl (e.g., imidazolinyl), pyrazolidinyl (e.g., 1-pyrazolidinyl, 2-pyrazolidinyl), pyrazolinyl (e.g., pyrazolinyl), piperidinyl (piperidino, 2-piperidinyl), piperazinyl (e.g., 1-piperazinyl), indolynyl (e.g., 1-indolynyl), isoindolinyl (e.g., isoindolinyl), morpholinyl (e.g., morpholino, 3-morpholinyl), 4H-1,2,4-oxadiazol-5-one, 1,2,3,4-teterahydro-1,8-naphthyridine, 1,3-benzodioxolanyl, 1-benzoxolanyl, 1,4-benzodioxanyl and the like.

Preferable are pyrazolidinyl, piperidinyl, pyrrolinyl, morpholinyl, 1,3-benzodioxolanyl, 1-benzoxolanyl, 1,4-benzodioxanyl and the like as "non-aromatic heterocyclic group" for $R^6$.

In the present specification, the term "arylene" herein used means a divalent group of the above-mentioned "aryl". Examples of the arylene are phenylene naphthylene, and the like. Mentioned in more detail, it is exemplified by 1,2-phenylene, 1,3-phenylen, 1,4-phenylene, and the like. Preferable is 1,4-phenylene.

In the present specification, the term "heteroarylene" herein used means a divalent group of the above-mentioned "heteroaryl". Examples of the heteroarylene are thionphene-diyl, furan-diyl, pyridine-diyl, and the like. Preferable are 2,5-thionphene-diyl, 2,5-furan-diyl, and the like.

In the present specification, the term "halogen" herein used means fluoro, chloro, bromo, and iodo. Fluoro, chloro, and bromo are preferred.

In the present specification, the term "lower alkyloxy" herein used are methyloxy, ethyloxy, n-propyloxy, isopropyloxy, n-butyloxy, isobutyloxy, s-butyloxy, t-butyloxy, n-pentyloxy, n-hexyloxy and the like. Preferable are methyloxy, ethyloxy, n-propyloxy, isopropyloxy, n-butyloxy, s-butyloxy, isobutyloxy, and t-butyloxy. Preferable is $C_1$ to $C_3$ alkyloxy.

In the present specification, the term "lower alkenyloxy" herein used are vinyloxy, allyloxy, propenyloxy, 3-butenyloxy, 2-butenyloxy (crotonyloxy, isocrotonyloxy), 1-butenyloxy, isopentenyloxy and the like. Preferable is $C_2$ to $C_3$ alkenyloxy.

In the present specification, the term "lower alkylthio" herein used are methylthio, ethylthio, propylthio, isopropylthio, butylthio, s-butylthio, isobutylthio, t-butylthio and the like. Preferable is $C_1$ to $C_3$ alkylthio.

In the present specification, the term "halo(lower)alkyl" employed alone or in combination with other terms includes the above-mentioned "lower alkyl" which is substituted with the above mentioned "halogen" at 1 to 8 positions, preferably, at 1 to 5. Examples of the halo(lower)alkyl are trifluoromethyl, trichloromethyl, difluoroethyl, trifluoroethyl, dichloroethyl, trichloroethyl, and the like. Preferable is trifluoromethyl.

In the present specification, examples of the term "halo (lower)alkyloxy" herein used are trifluoromethyloxy and the like.

In the present specification, examples of the term "halo (lower)alkylthio" herein used are trifluoromethylthio and the like.

In the present specification, the term "hydroxy(lower) alkyl" includes the above-mentioned "lower alkyl" which is substituted with hydroxyl group. Examples of the hydroxy (lower)alkyl are hydroxymethyl, 1-hydroxyethyl, 2-hydroxyethyl, 1-hydroxypropyl, 2-hydroxypropyl, 3-hydroxypropyl, and the like. Preferable are hydroxymethyl, 1-hydroxyethyl, and 2-hydroxyethyl.

In the present specification, examples of the term "lower alkyloxycarbonyl" herein used are methyloxycarbonyl, ethyloxycarbonyl, n-propyloxycarbonyl, isopropyloxycarbonyl, and the like.

In the present specification, examples of the term "lower alkylsulfonyl" herein used are methylsulfonyl, ethylsulfonyl, and the like. Preferable is methylsulfonyl.

In the present specification, the term "acyl" employed alone or in combination with other terms includes alkylcarbonyl in which alkyl group is the above mentioned "lower alkyl" or arylcarbonyl in which aryl group is the above mentioned "aryl". Examples of the acyl are acetyl, propyonyl, benzoyl, and the like. "Lower alkyl" and "aryl" may be substituted respectively with substituents mentioned below.

In the present specification, examples of the term "acyloxy" herein used are acetyloxy, propyonyloxy, benzoyloxy, and the like.

In the present specification, examples of the term "aryloxy" herein used are phenyloxy, 1-naphthoxy, 2-naphthoxy, and the like.

In the present specification, examples of the term "aralkyloxy" herein used are benzyloxy, phenylethyloxy, phenylpropyloxy, and the like.

In the present specification, the term "optionally substituted amino" employed alone or in combination with other terms includes amino, or amino substituted with one or two of the above mentioned "lower alkyl", "aralkyl", "heteroarylalkyl" or "acyl". Preferable are amino or amino substituted with one or two of $C_1$ to $C_6$ alkyl, phenyl $C_1$ to $C_3$ alkyl, pyridyl $C_1$ to $C_3$ alkyl, $C_1$ to $C_6$ alkylcarbonyl, or arylcarbonyl. Examples are amino, methylamino, dimethylamino, ethylmethylamino, diethylamino, benzylamino, acetylamino, benzoylamino, and the like. Preferable are amino, methylamino, dimethylamino, ethylmethylamino, diethylamino, and acetylamino.

In the present specification, preferable are aminocarbonyl or aminocarbonyl optionally substituted with one or two of $C_1$ to $C_6$ alkyl as "optionally substituted aminocarbonyl". Examples are aminocarbonyl, methylaminocarbonyl, dimethylaminocarbonyl, ethylmethylaminocarbonyl, diethylaminocarbonyl, and the like. Preferable are aminocarbonyl and dimethylaminocarbonyl.

In the present specification, the substituents of "optionally substituted lower alkyl" are cycloalkyl, hydroxy, lower alkyloxy, mercapto, lower alkylthio, halogen, nitro, cyano, carboxy, lower alkyloxycarbonyl, halo(lower)alkyl, halo(lower)alkyloxy, optionally substituted amino, optionally substituted aminocarbonyl, acyl, acyloxy, optionally substituted non-aromatic heterocyclic group, aryloxy, aralkyloxy, lower alkylsulfonyl, guanidino, azo group, optionally substituted ureide, carbamoyl, and the like. These substituents are able to locate at one or more of any possible positions.

Preferred substituents of "optionally substituted lower alkyl" for $R^2$ and $R^{2'}$ are halogen, hydroxy, carboxy, carbamoyl, mercapto, lower alkylthio, and cycloalkyl.

Preferred substituents of "optionally substituted lower alkyl" for $R^3$ are hydroxy, lower alkyloxy, and optionally substituted non-aromatic heterocyclic group.

In the present specification, the substituents of "optionally substituted arylene", "optionally substituted heteroarylene", "optionally substituted aryl", "optionally substituted heteroaryl", "optionally substituted non-aromatic heterocyclic group", "optionally substituted aralkyl", "optionally substituted heteroarylalkyl", and "optionally substituted ureide" herein used are optionally substituted lower alkyl, cycloalkyl, lower alkenyl, lower alkynyl, hydroxy, lower alkyloxy, mercapto, lower alkylthio, halogen, nitro, cyano, carboxy, lower alkyloxycarbonyl, halo(lower)alkyl, halo(lower)alkyloxy, halo(lower)alkylthio, optionally substituted amino, optionally substituted aminocarbonyl, acyl, acyloxy, optionally substituted aryl, optionally substituted heteroaryl, optionally substituted non-aromatic heterocyclic group, optionally substituted aralkyl, lower alkylsulfonyl, guanidino, azo group, or optionally substituted ureide, carbamoyl, lower alkenyloxy and the like. These substituents are able to locate at one or more of any possible positions.

Substituents of "optionally substituted arylene" and "optionally substituted heteroarylene" for $R^4$ are halogen, nitro, cyano, lower alkyloxy, and the like. Preferable are unsubstituted "arylene" and unsubstituted "heteroarylene".

Preferred substituents of "optionally substituted aryl" for $R^2$ and $R^{2'}$ is hydroxy.

Preferred substituents of "optionally substituted aryl" for $R^3$ are hydroxy, lower alkyloxy, halogen, or halo(lower)alkyl.

Substituents of "optionally substituted aryl" for $R^6$ are halogen, lower alkyl, cycloalkyl, lower alkenyl, lower alkynyl, lower alkyloxy, lower alkenyloxy, lower alkylthio, halo(lower)alkyl, halo(lower)alkyloxy, halo(lower)alkylthio, hydroxy, hydroxy(lower)alkyl, carboxy, lower alkyloxycarbonyl, lower alkylsulfonyl, carbamoyl, acyl, acyloxy, nitro, cyano, optionally substituted amino, or optionally substituted aminocarbonyl. Preferable are halogen, lower alkyl, lower alkyloxy, lower alkylthio, halo(lower)alkyl, halo(lower)alkyloxy, halo(lower)alkylthio, hydroxy, hydroxy(lower)alkyl, acyl, nitro, cyano, or optionally substituted amino.

Preferred substituents of "optionally substituted heteroaryl" for $R^2$ and $R^{2'}$ are hydroxy or halogen.

Preferred substituents of "optionally substituted heteroaryl" for $R^3$ are hydroxy, lower alkyloxy, halogen, or halo(lower)alkyl.

Substituents of "optionally substituted heteroaryl" for $R^6$ herein used are halogen, lower alkyl, cycloalkyl, lower alkenyl, lower alkynyl, lower alkyloxy, lower alkenyloxy, lower alkylthio, halo(lower)alkyl, halo(lower)alkyloxy, halo(lower)alkylthio, hydroxy, hydroxy(lower)alkyl, carboxy, lower alkyloxycarbonyl, lower alkylsulfonyl, carbamoyl, acyl, acyloxy, nitro, cyano, optionally substituted amino, or optionally substituted aminocarbonyl. Preferable are halogen, lower alkyl, lower alkyloxy, lower alkylthio, halo(lower)alkyl, halo(lower)alkyloxy, halo(lower)alkylthio, hydroxy, hydroxy(lower)alkyl, acyl, nitro, cyano, or optionally substituted amino.

Preferred substituents of "optionally substituted aralkyl" for $R^2$ and $R^{2'}$ are hydroxy, halogen, nitro, lower alkyloxy, or halo(lower)alkyl.

Preferred substituents of "optionally substituted aralkyl" for $R^3$ are hydroxy, lower alkyloxy, halogen, halo(lower)alkyl, or nitro.

Preferred substituents of "optionally substituted heteroarylalkyl" for $R^2$ and $R^{2'}$ are halogen or hydroxy.

Preferred substituents of "optionally substituted heteroarylalkyl" for $R^3$ are hydroxy, lower alkyloxy, halogen, or halo(lower)alkyl.

Substituents of "optionally substituted non-aromatic heterocyclic group" for $R^6$ herein used are halogen, lower alkyl, cycloalkyl, lower alkenyl, lower alkynyl, lower alkyloxy, lower alkenyloxy, lower alkylthio, halo(lower)alkyl, halo(lower)alkyloxy, halo(lower)alkylthio, hydroxy, hydroxy(lower)alkyl, carboxy, lower alkyloxycarbonyl, lower alkylsulfonyl, carbamoyl, acyl, acyloxy, nitro, cyano, optionally substituted amino, or optionally substituted aminocarbonyl. Preferable are halogen, lower alkyl, lower alkyloxy, lower alkylthio, halo(lower)alkyl, halo(lower)alkyloxy, halo(lower)alkylthio, hydroxy, hydroxy(lower)alkyl, acyl, nitro, cyano, or optionally substituted amino.

A compound of the present invention has excellent inhibitory activities against plural MMPs (e.g., MMP-2, MMP-8, MMP-9, MMP-12, and MMP-13). Furthermore, it has relatively low protein binding ratio, high oral absorbability, and low toxicity. Therefore, it is excellent for medicament.

The sulfonamide derivatives having an isoxazole ring of the present invention have inhibitory activities against the matrix metalloproteinase, especially excellent inhibitory activities against plural MMPs and are useful for the treating or preventing agent for diseases caused by MMP. Furthermore, it has relatively low protein binding ratio, high oral absorbability, and low toxicity. Therefore, it is excellent for medicament.

BEST MODE FOR CARRYING OUT THE INVENTION

The isoxazole derivatives of the present invention are able to be synthesized in accordance with the following methods A or B. Further, a compound represented by the general formula (I) wherein W has a cyclic group may be synthesized by the methods described in WO00/46189, WO00/58304, and WO00/58280.

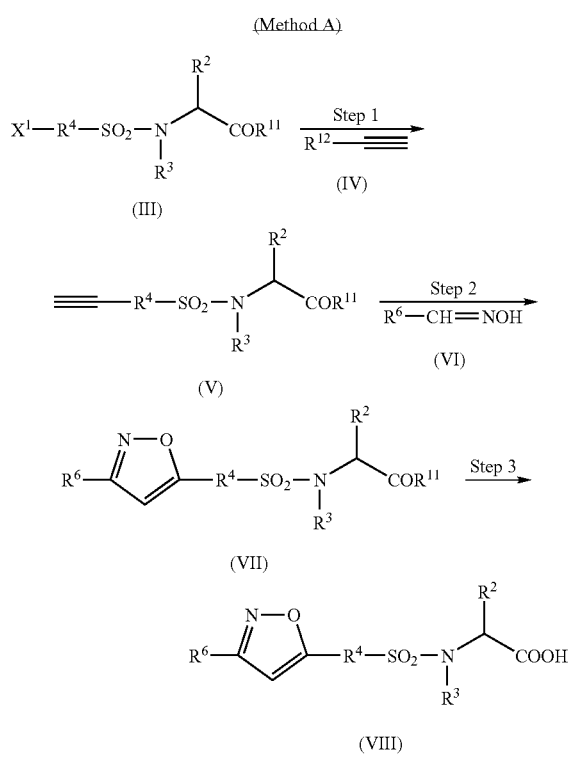

wherein $R^2$, $R^3$, $R^4$, and $R^6$ are as defined above, $R^{11}$ is a protecting group of carboxyl group, $R^{12}$ is a protecting group including a silyl group, and $X^1$ is halogen.

Step 1

This step is a process of obtaining a compound (V) by introduction of a triple bond into a compound (III). To a solution of a halide (III) and a silylacetylene compound (IV) in a solvent are added a palladium catalyst and a copper catalyst at −10° C. to 80° C., preferably 0° C. to 50° C., and the mixture is degassed under argon atmosphere sufficiently. Then to the mixture is added an amine, and stirred at 0° C. to 100° C., preferably 10° C. to 80° C. for 3 to 72 h, preferably 8 to 24 h. After cooling, the mixture is extracted under an acidic condition, and then subjected to a usual work-up. The extract is dried, and concentrated under reduced pressure. To the residue is added a base and a solvent, and the mixture is stirred at −10° C. to 80° C., preferably 0° C. to 50° C. for 3 to 72 h, preferably 8 to 24 h. After the solvent is evaporated, the residue is subjected to a usual work-up. A compound (V) is obtained.

Preferred silylacetylene compounds are trimethylsilylacetylene and the like.

Preferred solvents for the coupling reaction are dimethylformamide, benzene, toluene, ethyl acetate, tetrahydrofuran and the like.

Preferred palladium catalysts are dichlorobis(triphenylphosphine)palladium, tetrakis(triphenylphosphine)palldium, palladium acetate and the like.

Preferred copper catalysts are copper iodide and the like.

Preferred amines are triethylamine, tripropylamine, tributylamine and the like.

Preferred bases for the deprotection reaction are potassium carbonate, sodium carbonate and the like.

Preferred solvents for the deprotection reaction are methanol, ethanol and the like.

Step 2

This step is a process of constructing an isoxazole ring. An aldoxime (VI) is dissolved in a solvent under an argon atmosphere, and a halogenating reagent is added thereto. Then the mixture is stirred at 10° C. to 150° C., preferably 30° C. to 100° C. for 0.1 to 6 h, preferably 3 to 5 h. A solution of a compound (V) and an amine is added thereto at −20° C. to 30° C., preferably −10° C. to 10° C., and the mixture is stirred at −10° C. to 80° C., preferably 10° C. to 50° C. for 6 to 72 h, preferably 12 to 24 h. A compound (VII) is obtained.

Examples of the solvents are dimethylformamide, dimethylsulfoxide and the like.

Examples of the halogenating reagents are N-chlorosuccinimide, N-bromosuccinimide and the like.

Examples of the amines are trimethylamine, triethylamine N-methylmorpholine and the like.

Step 3

This step is a process of deprotection of the protecting group for carboxy in a compound (VII). The process may be carried out in accordance with the same procedure as Method A-Step 1 described in WO97/27174.

(Method B)

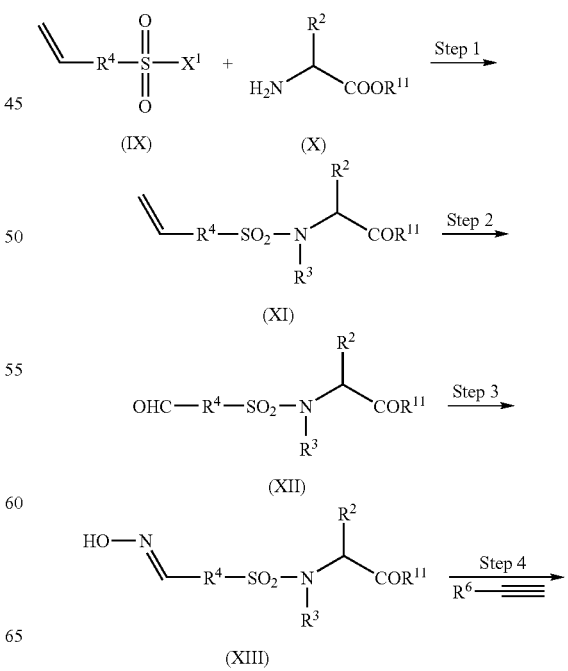

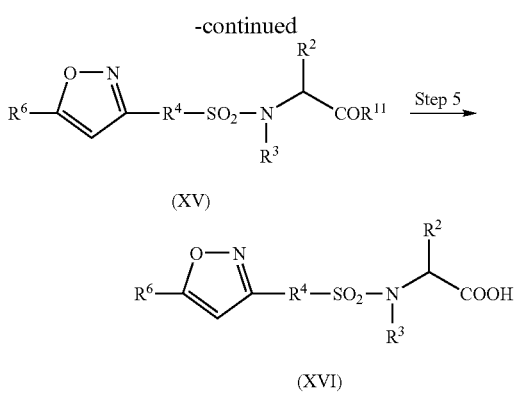

(XV)

(XVI)

wherein $R^2$, $R^3$, $R^4$, $R^6$, $R^{11}$, and $X^1$ are as defined above.

Step 1

This step is a process of obtaining a compound (XI) by sulfonylation to the amino group of a compound (X). The process may be carried out in accordance with the same procedure as Method A-Step 1 described in WO97/27174.

Step 2

This step is a process of obtaining an aldehyde (XII) by ozone oxidation of the double bond of a compound (XI). The process may be carried out under a usual condition of ozone oxidation. For example, a compound (XI) is dissolved in a solvent, cooled to −100° C. to −30° C., preferably −90° C. to −50° C., and then stirred with bubbling ozone gas for 0.1 to 6 h, preferably 0.2 to 3 h. A reductant is added thereto at the same temperature, and the mixture is stirred for 0.1 to 6 h, preferably 0.2 to 3 h, moreover stirred at −10° C. to 50° C., preferably 0° C. to 40° C. for 0.1 to 6 h, preferably 0.2 to 3 h. The reaction mixture is concentrated under reduced pressure, and the obtained compound (XII) is used for next step without any purification.

Preferred solvents are methylene chloride, chloroform, methanol, mixed solvent of methylene chloride and methanol, and the like.

Preferred reductants are methyl sulfide, triphenylphosphine and the like.

Step 3

This step is a process of deriving to an aldoxime (XIII) from an aldehyde (XII) obtained by the step as above. To a solution of a compound (XII) and a hydroxylamine derivative is added a base, and the mixture is stirred at −10° C. to 80° C., preferably 0° C. to 50° C. for 3 to 72 h, preferably 8 to 48 h. A compound (XIII) is obtained.

Preferred solvents are tetrahydrofuran, water, mixed solvent of tetrahydrofuran and water and the like.

Examples of the hydroxylamine derivatives are hydroxylamine hydrochloride, hydroxylamine sulfate and the like.

Examples of the bases are sodium hydrogencarbonate, sodium carbonate, potassium hydrogencarbonate, potassium carbonate, and the like.

Step 4

This step is a process of constructing an isoxazole ring from an aldoxime (XIII). A solution of an aldoxime (XIII) and a halogenating reagent is stirred at 10° C. to 150° C., preferably 30° C. to 100° C. for 0.1 to 6 h. After the temperature of the mixture is controlled to −20° C. to 30° C., preferably −10° C. to 10° C., a solution of a compound (XIV) and an amine is added thereto. The mixture is stirred at the same temperature as above for 1 to 60 min, preferably 3 to 30 min, and then stirred at −10° C. to 80° C., preferably 10° C. to 50° C. for 6 to 72 h, preferably 12 to 48 h. A compound (XV) is obtained.

Examples of the solvents are dimethylformamide, dimethylsulfoxide and the like.

Examples of the halogenating reagents are N-chlorosuccinimide, N-bromosuccinimide and the like.

Examples of the amines are N-methylmorpholine, triethylamine and the like.

Step 5

This step is a process of deprotection of the protecting group for carboxy in a compound (XV). The process may be carried out in accordance with the same procedure as Method A-Step 1 described in WO97/27174.

Therapeutic effects of the compounds of the present invention for chronic obstructive pulmonary disease, nephritis, cancer, heart failure, aortic aneurysm, osteoarthritis, adjuvant arthritis, intraocular angiogenesis, and diabetic retinopathy may be confirmed by the methods as follow.

1) Chronic Obstructive Pulmonary Disease

Sprague-Dawley male rats (390-430 g initial body weight) are exposed daily to smoke from commercial filtered cigarettes (30 cigarettes/rat/day, 5 days/week, for 7 to 8 weeks) with a smoke-generating and whole-body exposure system. The animals receive 30 mg/kg p.o. twice daily of the test compound, which is suspended with 0.5% methyl cellulose. Vehicle animals receive 2 ml/kg of 0.5% methyl cellulose. At 16-24 hr after the last exposure with cigarette smoke, anesthesia is induced with intraperitoneal injection of 40 mg/kg of pentobarbital sodium. Immediately after muscle relaxation with intravenous pancuronium bromide (0.3 mg/rat), animals are mechanically ventilated with a pressure-limited ventilator and are evaluated dynamic compliance. After exsanguination, the lung is attached to a glass syringe via a connector tube and continuously inflated through the airway to a transpulmonary pressure of 30 $cmH_2O$, deflated them to a Ptp of 0 $cmH_2O$, and aspirated them to a Ptp of −20 $cmH_2O$. The change of Ptp and lung volume is monitored and recorded as the deflation pressure-volume (P-V) curve. Static lung compliance defined as the slope of steep portion of the deflation P-V curve is evaluated. Inspiratory capacity (IC) defined as the difference in lung volume between total lung capacity at a Ptp of 25 $cmH_2O$ and functional residual capacity at a Ptp of 0 $cmH_2O$ is evaluated.

Data are expressed as means±S.D. Statistical analysis is performed with one-sided Student's t-test. A value of P<0.05 is considered significant.

2) Nephritis 5-week-old male Slc-Wistar rats are reared under the conditions of room temperature of 25° C., 40-60% humidity and 12 hour cycles of light and darkness and fed on solid chow (CA-1, Clea Japan) and tap water ad libitum. After one week's preliminary rearing, each rat is housed in a stainless metabolic cage for acclimation for one week, and is used for experiment at 7 weeks of old (body weight: 150-180 g). E-30 monoclonal antibody (J.J.N., vol. 36, p 106, 1994) is diluted with saline at 100 μg/0.4 ml and is administered from tail vein at the volume of 0.4 ml/body. A test compound is suspended with 5% gum arabic solution and is given at the dose of 30 mg 1.5 hours before E-30 injection. Subsequently, the test compound of 30 mg is orally administered once a day from the next day. The rats are housed in stainless metabolic cages just after the administration of test compound, and then 24-hour urine samples are collected. After measuring the volume, the urine is centrifuged at 3000 rpm for 10 min at room temperature. The supernatant is used for the determination of urinary excretion of protein. Urinary protein is determined by pyrogallole red method (Micro TP-test Wako, Wako Pure Chemical Industries, Ltd.). The amount of urinary protein excretion on day 5 or 2 in compound-treated group is compared with that in vehicle-treated one, and inhibitory ratio of urinary protein excretion is calculated.

On the follow-up day (day 5), blood samples were collected and processed for the determination of blood urea nitrogen (BUN). Concentration of blood urea nitrogen was measured with Urea nitrogen B-test Wako (Wako Pure Chemical Industries, Ltd.), and inhibitory effects on increased blood urea nitrogen is calculated by comparing with that in vehicle-treated one.

3) Cancer

Lewis mouse lung carcinoma cells ($4\times10^5$ cells) are inoculated into the tail vein of BDF1 mice. Test compounds are suspended in the vehicle (0.5% methylcellulose solution) and are orally administered to the mice total five times (−4, 1, 24, 48 and 72 h after tumor inoculation). The doses of the compounds are 20 and 200 mg/kg. At 14 day after tumor inoculation, tumor nodules formed in the lung of the treated mice are counted and the antitumor efficacy is evaluated.

4) Heart Failure a) Permanent Coronary Ligation

Male Wistar rats (12 weeks old) are anesthetized with sodium pentobarbital (30 mg/kg, i.p.) and intubated and ventilated with room air before a left thoracotomy is performed. The pericardium is opened and the left anterior descending coronary artery is located and ligated with a 5-0 nylon suture, and then the incision is immediately closed. After the rats began to awaken, the rats are returned to the animal cages, and then housed under normal conditions. Seven days after the coronary ligation the 1-lead electrocardiogram is recorded and then the rats are selected, of which the descent of Q-wave is detected. Test compound (30 mg/kg/day, as the suspension with 1.5% gum arabic) is orally administered from the 8th to the 21st day after permanent ligation. On the next day of last administration, the left ventricular (LV) end-diastolic pressure is measured, and then the assessment of pressure-volume relationships is performed, according to the methods of Experiment b) and c) mentioned as follows.

b) Measurement of LV Systolic and Diastolic Pressures (Cardiac Function)

Under anesthesia with halothane, polyethylene catheter is inserted into left ventricle via right carotid artery. LV end-diastolic pressure and the maximum rate of pressure rise (+dP/dt) and decline (−dP/dt) are measured by a pressure transducer connected to the catheter.

c) Measurement of Pressure-volume Relationships

To define the passive pressure-volume characteristics of the left ventricle, the heart is arrested in diastole with 5M potassium chloride under anesthesia with halothane, and immediately isolated. After the removal of the right ventricular free wall, a saline-filled double lumen catheter is inserted 6 mm into the left ventricle via the aorta, and the atrioventricular groove is ligated. The ventricle is compressed manually to expel blood by perfusion of heparinized saline via the catheter and adjusted a negative pressure of −5 mmHg, which is taken as zero volume. Saline is infused at 0.68 or 0.20 mL/min (0.34 mL/min=20.4 mL/h) via one lumen while intraventricular pressure is continually recorded through the other lumen over the pressure range −5 to 30 mmHg (ref. Sonoki et al., Jpn J Pharmacol, 74, 171 (1991)). The left ventricular compliance (the index of left ventricular dilatation (remodeling)) is calculated by using the left ventricular volume and pressure values measured in Experiment b) and c).

5) Aortic Aneurysm

Examples of the methods for confirming therapeutic effects to aortic aneurysm are two methods as follow.

A) Assay Using an Elastase-induced Rat Abdominal Aortic Aneurysm Model

Adult male Sprague-Dawley rats, weighing 380-430 g are used. Animals undergo elastase perfusion of the infrarenal aorta as described by Anidjar et al. (Circulation 1990; 82:973) with modifications. A laparotomy is performed under anesthesia, and infrarenal abdominal aorta (a 1 cm segment) is dissected free of the inferior vena cava and clamp all lumber branches with microclips. Through a separate groin incision, a PE50 polyethylene tube (Clay Adams) is introduced into the left femoral artery and advance into the distal infrarenal aorta. The infrarenal aorta is clamped above the level of tube tip and the tube within aorta is secured with a silk ligature just above the aortic bifurcation. This isolated segment is perfused continuously for 2 hours with 2 mL of 2.5% elastase in 0.01M phosphate buffer pH 8.0 (Pancreatic Elastase Type I; Sigma Co.) by means of a syringe pump (Terumo Co. ME-STC525). After perfusion is completed, the tube is withdrawn, the femoral artery is ligated, blood flow is restored in the aortic segment and wounds are closed. Following aortic perfusion, rats are treated every 7 days with MMP inhibitors or a control vehicle beginning at the day of purfusion or a few days later and continuing until the animal is killed. Inhibitory effect of the inhibitors on aortic aneurysms is evaluated by a percentage change of aortic diameter, histological assessment of tissue sections with Elastica-Masson stain for elastin or measurement of tissue elastin, desmosine contents in the purfused segment. Maximal diameter of the 1 cm segment before and after perfusion and at autopsy is measured under physiologic conditions for each rat by means of a digital micrometer (Mitutoyo Co., CD-S15C). The increase in aortic diameter is calculated and expressed as a percentage change from post-perfusion.

B) Assay Using a Rabbit Abdominal Aortic Aneurysm Model

Hypercholesterolemic rabbits (NZW weighing about 2.5 kg) that fed 0.5% cholesterol diet for 1-2 weeks are used. Experimental surgery is performed on each animal as described by Freestone et al. (Arterioscler Thromb Vasc Biol. 1997; 17:10) with modifications. A two cm segment of infrarenal abdominal aorta is dissected free of the inferior vena cava after a laparotomy under anesthesia and painted for 15 minutes with a solution containing 0.05M sodium thioglycollate (Sigma) and 0.15M calcium chloride in 0.1M Tris-HCl buffer (pH7.5). Following the experimental surgery, rabbits are treated every day for 2-3 weeks with MMP inhibitors or a control vehicle beginning at the day of surgery or a few days later. All animals are autopsied at the day of final treatment. Inhibitory effect of the inhibitors on aortic aneurysms is evaluated by a percentage change of aortic diameter, histological assessment of tissue sections with Elastica-Masson stain for elastin. Maximal diameter of the 2 cm segment before and after painting with the solution and at autopsy is measured under physiologic conditions by means of a digital micrometer (Mitutoyo Co., CD-S15C). The increase in aortic diameter is calculated and expressed as a percentage change from postpainting.

6) Osteoarthritis

Guinea pig osteoarthritis model is prepared according to the procedure reported by Meacock et. al. (J. Exp. Path. 71: 279-293, 1990), by medial meniscectomy and collateral ligament transection on the right knee of 12 weeks old female Hartley guinea pigs (Charles River Japan). 0.5% methylcellulose or compounds (30 mg/kg) are orally administered once daily from the following day of the surgery for 10 days.

On the next day of final administration, femoral chondyles and tibial plateaus of right knees are removed. The surfaces of the tibial plateau are stained with India ink (Kuretake), then photographed using a digital camera (Nikon). Whole area and stained area of the medial plateaus are measured by using a computer-aided image analyzing system (WinRoof, MITANI CORPORATION).

(Lesion area (%)=Stained area/Whole area×100)

In a similar way, oral administration to 12 weeks old female NZW rabbits (Kitayama Labes) or 12 weeks old female SD rats (Clea Japan) for 6 weeks also shows that the present invention compounds are effective on the treatment of osteoarthritis.

7) Adjuvant Arthritis

Adjuvant arthritis is induced by subcutaneous injection of *Mycobacterium butyricum* into the right foot paw of 7 weeks old female Lewis rats (Japan Charles River) according to the procedures reported by Fretcher et al. (J. Pharmacol. Exp. Ther. 284(2): 714-721). Vehicle (0.5% methylculloose solution) or a test compound (30 mg/kg) is orally administered once a day from the following day of surgery for 21 days. Hind paw volume is measured using a hydroplethysmometer (Shionogi, Japan) 21 days after induction of arthritis. And then spleen and thymus are taken and weighed. Both of hind legs are photographed by X-lay (OHMIC), and destruction level of articulation of X-lay image is scored from 0 (normal) to 3 (perfect destruction of bone and cartilage) in blind manner.

8) Intraocular Angiogenesis 7-day-old C57BL/6J mice are reared under the conditions of 75% oxygen atmosphere for 5 days, and then under normal atmospheric conditions for 5 days. An eyeball are extracted from the mice and subjected to dipping fixation in 10% formalin solution. The fixed eyeball is embedded in paraffin, and interrupted tissue slices of 6 μm thickness are prepared with ca. 100 μm spacing. Tissue slices containing lenticular and not containing optic disk are subjected to PAS staining, and the number of nucleus in cells which protruding from retina to vitreum is counted as the index of neovascular. Test compounds are administered subcutaneously or orally, for evaluating their drug efficacy.

9) Diabetic Retinopathy 20-27 week-old GK rats (Shionogi Aburahi Laboratories, Shiga, Japan Goto Y, Suzuki K, Ono T, Sasaki M, Toyota T. Advances in Experimental Medicine and Biology 246, 1988, 29-31) as the model of type II diabetic animal are anaesthetized with halothane. Mydriasis is induced by administrarion of Mydrin P® (Santen Pharmaceutical Co., Ltd, Generic name: Tropicamide Phenylephrine hydrochloride), and then 10,000 lux of green light (L4887, Hamamatsu Photonics K.K.) is irradiated to optic disk and around its periphery for 3 minutes. Subsequently, lesion on the blood vessel of retina is elicited by intravenous infusion of 20 mg/kg of Rose Bengal as photosensitizer. After 20 minutes of elicitation of lesion, a test compound (30 mg/kg/day po) is administrated. Image of the ocular fundus is photograhed just behind the elicitation of lesion, 1, 3, and 5 days after by retinal camera (PROIII, KOWA) for the observation of change with the lapse of time in ocular fund.

The term "solvate" in the present invention herein used includes a solvate with an organic solvent(s), a hydrate and the like. These hydrates can coordinate with any water molecules.

The term "compound of the present invention" herein used includes a pharmaceutically acceptable salt or its solvate. The salt is exemplified by a salt with alkali metals (e.g., lithium, sodium, potassium, and the like), alkaline earth metals (e.g., magnesium, calcium, and the like), ammonium, organic bases, amino acids, mineral acids (e.g., hydrochloric acid, hydrobromic acid, phosphoric acid, sulfuric acid, and the like), or organic acids (e.g., acetic acid, citric acid, maleic acid, fumaric acid, benzenesulfonic acid, p-toluenesulfonic acid, and the like). These salts and solvates can be formed by the usual method.

The compound of the present invention is not restricted to any particular isomers but includes all possible isomers (e.g. optically active substance) and racemic modifications.

The compound of the present invention has excellent inhibitory activities against MMPs, as described in the following test example.

Definitely, the compounds of the present invention are useful in the treatment of diseases such as chronic obstructive pulmonary disease, osteoarthritis, rheumatoid arthritis, adjuvant arthritis, corneal ulceration, periodontal disease, advanced virus infection (e.g., HIV infection), arteriosclerosis obliterans, arteriosclerotic aneurysm, aortic aneurysm, atherosclerosis, restenosis, sepsis, septic shock, coronary thrombosis, aberrant angiogenesis, intraocular angiogenesis, scleritis, multiple sclerosis, hepatocirrhosis, open angle glaucoma, retinopathies (e.g., diabetic retinopathy), proliferative retinopathy, neovascular glaucoma, pterygium, keratitis, epidermolysis bullosa, psoriasis, diabetes, nephritis, neurodegengerative disease, inflammation, osteoporosis, deossification, gingivitis, tumor growth, tumor angiogenesis, ocular tumor, angiofibroma, hemangioma, fever, hemorrhage, coagulation, cachexia, anorexia, acute infection, shock, autoimmune disease, malaria, Crohn disease, meningitis, heart failure, asthmatic respiratory tract disease, arteriosclerosis, cancer and gastric ulcer.

When the compound of the present invention is administered to a person for the treatment of the above diseases, it can be administered orally as powder, granules, tablets, capsules, pilulae, and liquid medicines, or parenterally as injections, suppositories, percutaneous formulations, insufflation, and the like. An effective dose of the compound is formulated by being mixed with appropriate medicinal admixtures such as excipient, binder, penetrant, disintegrators, lubricant, and the like if necessary. Parenteral injections are prepared by sterilizing the compound together with an appropriate carrier.

The dosage varies with the conditions of the patients, administration route, their age, and body weight. In the case of oral administration, the dosage can generally be between 0.1 to 100 mg/kg/day, and preferably 0.1 to 20 mg/kg/day for adult.

The following examples and test examples are provided to further illustrate the present invention and are not to be constructed as limiting the scope thereof.

EXAMPLE

Abbreviations described below are used in the following examples.
Me: methyl
Et: ethyl
n-Pr: n-propyl
i-Pr: isopropyl
n-Bu: n-butyl
s-Bu: s-butyl
i-Bu: isobutyl
Ph: phenyl
Bn: benzyl
4-OH-Bn: 4-hydroxybenzyl

Example 1

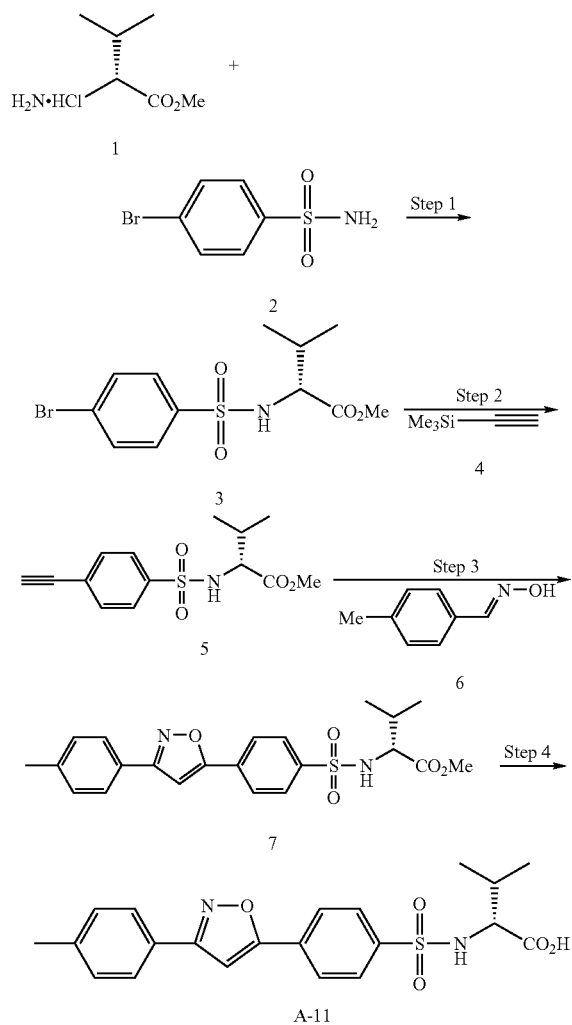

Step 1

To a suspension of D-valine methyl ester hydrochloride (1) (30 g, 179 mmol) in dry tetrahydrofuran (300 mL) were added N-methylmorpholine (49.1 mL, 448 mmol) and 4-bromobenzenesulfonyl chloride (2) (43.4 g, 170 mmol) successively under ice-cooling with stirring. After stirring for 16 h at room temperature, the reaction mixture was poured into the water and extracted with ethyl acetate. The organic layer was washed with 1 mol/L hydrochloric acid, 5% $NaHCO_3$ solution, and water successively, and then dried over anhydrous sodium sulfate. After filtration, the organic layer was concentrated under reduced pressure. Recrystallization of the crystalline residue from ethyl acetate/hexane gave 39.6 g of compound (3). (yield 66.5% from 4-bromobenzenesulfonyl chloride)

$^1$H NMR ($CDCl_3$, δ ppm): 0.87 (d, J=6.9 Hz, 3H), 0.95 (d, J=6.9 Hz, 3H), 2.21 (m, 1H), 3.48 (s, 3H), 3.74 (dd, J=10.2, 5.1 Hz, 1H), 5.19 (br, 1H), 7.63 (d, J=9.0 Hz, 2H), 7.69 (d, J=9.0 Hz, 2H)

Step 2

To a solution of compound (3) (6.59 g, 12.2 mmol) and trimethylsilylacetylene (4) (1.44 g, 14.6 mmol) in dimethylformamide (45 mL) were added dichlorobis(triphenylphosphine)palladium (214 mg, 0.30 mmol) and copper iodide (116 mg, 0.61 mmol) at room temperature, and the mixture was degassed under an argon atmosphere sufficiently. Then to the mixture was added triethylamine (5.0 mL, 36.6 mmol), and the mixture was stirred at 50° C. for 16 h. After cooling to room temperature, the reaction mixture was poured into ice-2 mol/L hydrochloric acid, and extracted with ethyl acetate. The organic layer was washed with water and saturated sodium chloride solution successively. The organic layer was dried over anhydrous sodium sulfate, and then concentrated under reduced pressure. To the residue were added pottasium carbonate (139 mg, 1.01 mmol) and methanol (55 mL), and the mixture was stirred at room temperature for 16 h. After evaporation of methanol, to the residue was added water, and then the mixture was extracted with ethyl acetate. The organic layer was washed with water and saturated sodium chloride solution successively. The organic layer was dried over anhydrous sodium sulfate, and then concentrated under reduced pressure. The residue was subjected to silica gel column chromatography and the fraction eluted with ethyl acetate/hexane=¼ was collected. Recrystallization from ethyl acetate/hexane gave 2.72 g of compound (5) (yield 76%) with a melting point of 134-136° C.

IR (KBr, ν max $cm^{-1}$) 3329, 2971, 1718, 1709, 1347, 1330

$^1$H NMR ($CDCl_3$, δ ppm): 0.87 (d, J=6.9 Hz, 3H), 0.96 (d, J=6.9 Hz, 3H), 2.04 (m, 1H), 3.26 (s, 1H), 3.47 (s, 3H), 3.75 (dd, J=10.2, 5.1 Hz, 1H), 5.14 (d, J=9.6 Hz, 1H), 7.59 (d, J=8.4 Hz, 2H), 7.79 (d, J=8.1 Hz, 2H)

$[α]_D$+8.0±1.0° (c=0.503, DMSO, 22° C.)

Elemental analysis for $C_{13}H_{16}N_2O_4S$
Calcd.: C; 56.93, H; 5.80, N; 4.74, S; 10.86.
Found: C; 56.83, H; 5.68, N; 4.81, S; 10.66.

Step 3

To a solution of 4-methylbenzaldoxime (6) (452 mg, 3.33 mmol) in dimethylformamide (4 mL) was added N-chlorosuccinimide (450 mg, 3.33 mmol) under an argon atmosphere, and the mixture was stirred at 60° C. for 1 h. After ice-cooling, to the mixture was added the solution of compound (5) (493 mg, 1.67 mmol) and triethylamine (708 μl, 5.00 mmol) in dimethylformamide (2 mL), and the mixture was stirred at room temperature for 16 h. The reaction mixture was poured into ice-2 mol/L hydrochloric acid, and extracted with ethyl acetate. The organic layer was washed with water and saturated aqueous sodium chloride solution successively. The organic layer was dried over anhydrous sodium sulfate, and then concentrated under reduced pressure. Recrystallization of the residue from ethyl acetate/hexane gave 618 mg of compound (7) (yield 86%) with a melting point of 221-224° C.

IR (KBr, ν max cm$^{-1}$) 3283, 3113, 2968, 1713, 1615, 1445, 1431, 1387, 1293, 1268, 1140, 835, 819

$^1$H NMR (CDCl$_3$, δ ppm): 0.89 (d, J=6.9 Hz, 3H), 0.98 (d, J=6.9 Hz, 3H), 2.08 (m, 1H), 2.43 (s, 3H), 3.80 (dd, J=10.2, 4.8 Hz, 1H), 5.16 (d, J=10.2 Hz, 1H), 6.94 (s, 1H), 7.30 (d, J=8.4 Hz, 2H), 7.76 (d, J=8.1 Hz, 2H), 7.95 (s, 4H)

[α]$_D$ +3.9±0.9° (c=0.507, DMSO, 22° C.)

HR-FABMS m/z for C$_{22}$H$_{25}$N$_2$O$_5$S [M+H]$^+$

Calcd: 429.1484.

Found: 429.1486.

Step 4

To a solution of compound (7) (330 mg, 0.832 mmol) in dimethylsulfoxide (6 mL) was added 1 mol/L aqueous sodium hydroxide solution (2 mL) at room temperature, and the mixture was stirred for 16 h. The precipitated sodium salt was filtered, added into ice-2 mol/L hydrochloric acid, and extracted with ethyl acetate. The organic layer was washed with saturated aqueous sodium chloride solution. The organic layer was dried over anhydrous sodium sulfate, and then concentrated under reduced pressure. Crystallization of the residue from acetone/hexane gave 185 mg of the compound (A-11) (yield 58%) with a melting point of 241-243° C.

IR (KBr, ν max cm$^{-1}$) 3299, 2967, 1743, 1708, 1465, 1346, 1328, 1166, 1143, 1130, 1091, 1051, 836, 754, 609

$^1$H NMR (DMSO-d$_6$, δ ppm): 0.81-0.86 (m, 6H), 1.98 (m, 1H), 2.39 (s, 3H), 3.59 (m, 1H), 7.37 (d, J=8.1 Hz, 2H), 7.77 (s, 1H), 7.83 (d, J=8.1 Hz, 2H), 7.95 (d, J=8.4 Hz, 2H), 8.08 (d, J=8.4 Hz, 2H), 8.23 (d, J=9.3 Hz, 1H), 12.61 (br s, 1H)

[α]$_D$ −9.5±1.0° (c=0.503, DMSO, 24° C.)

Elemental analysis for C$_{21}$H$_{22}$N$_2$O$_5$S 0.8H$_2$O

Calcd.: C; 58.87, H; 5.56, N; 6.62, S; 7.41.

Found: C; 58.81, H; 5.55, N; 6.53, S; 7.48.

According to Example 1 and above mentioned Method A, the following compound (A-1) to compound (A-117), compound (B-1) to compound (B-20) were synthesized. Their structures and the results of their physical data were shown in Table 1 to 13 and Table 14 to 16. The mark * shows an asymmetric carbon.

TABLE 1

| Example No. | R$^2$ | R$^{2'}$ | R$^6$ | * | 1H-NMR (DMSO-d$_6$) |
|---|---|---|---|---|---|
| A-1 | Me | H | phenyl | R | 1.20(d, J=7.2Hz, 3H), 3.85(m, 1H), 7.52-7.61(m, 3H), 7.81(s, 1H), 7.92-7.98(m, 4H), 8.11(d, J=8.7Hz, 2H), 8.35(br s, 1H), 12.69(br s, 1H) |
| A-2 | Me | H | 4-Me-phenyl | R | 1.17(d, J=7.2Hz, 3H), 2.36(s, 3H), 3.83(m, 1H), 7.35(d, J=8.1Hz, 2H), 7.75(s, 1H), 7.81(d, J=8.1Hz, 2H), 7.94(d, J=8.7Hz, 2H), 8.07(d, J=8.7Hz, 2H), 8.33(d, J=7.5Hz, 1H), 12.7(br s, 1H) |
| A-3 | Me | H | 4-Me-phenyl | S | 1.17(d, J=7.2Hz, 3H), 2.35(s, 3H), 3.84(m, 1H), 7.35(d, J=8.1Hz, 2H), 7.75(s, 1H), 7.82(d, J=8.1Hz, 2H), 7.94(d, J=8.7Hz, 2H), 8.07(d, J=8.7Hz, 2H), 8.35(d, J=7.5Hz, 1H), 12.7(br s, 1H) |
| A-4 | Me | H | 4-MeO-phenyl | R | 1.20(d, J=6.9Hz, 3H), 3.89(s, 3H), 3.90(m, 1H), 7.20(d, J=8.7Hz, 2H), 7.79(s, 1H), 7.90(d, J=9.0Hz, 2H), 8.00(d, J=8.4Hz, 2H), 8.10(d, J=8.4Hz, 2H), 8.40(d, J=8.7Hz, 1H), 12.78(br s, 1H) |
| A-5 | Me | H | 4-CF$_3$O-phenyl | R | 1.19(d, J=7.2Hz, 3H), 3.85(m, 1H), 7.59(d, J=9.0Hz, 2H), 7.86(s, 1H), 7.97(d, J=8.7Hz, 2H), 8.05-7.12(m, 4H), 8.37(d, J=8.4Hz, 1H), 12.70(br s, 1H) |
| A-6 | Me | H | 4-CF$_3$O-phenyl | S | 1.20(d, J=7.2Hz, 3H), 3.86(m, 1H), 7.59(d, J=9.0Hz, 2H), 7.85(s, 1H), 7.97(d, J=8.4Hz, 2H), 8.06-7.13(m, 4H), 8.36(d, J=8.4Hz, 1H) |
| A-7 | Me | Me | 4-F-phenyl | — | 1.31(s, 6H), 7.42(t, J=7.5Hz, 2H), 7.78(s, 1H), 7.94-8.04(m, 4H), 8.09(d, J=8.1Hz, 2H), 8.19(s, 1H), 12.60(br s, 1H) |
| A-8 | Me | Me | 4-MeO-phenyl | — | 1.30(s, 6H), 7.12(d, J=8.7Hz, 2H), 7.72(s, 1H), 7.88(d, J=8.7Hz, 2H), 7.97(d, J=8.4Hz, 2H), 8.08(d, J=8.7Hz, 2H), 8.18(s, 1H), 12.60(br s, 1H) |

TABLE 1-continued

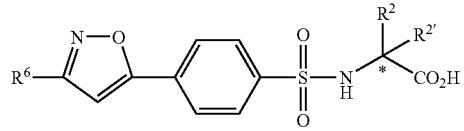

| Example No. | R² | R²' | R⁶ | * | 1H-NMR (DMSO-d₆) |
|---|---|---|---|---|---|
| A-9 | i-Pr | H | 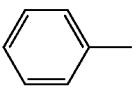 | R | 0.80-0.86(m, 6H), 1.96(m, 1H), 3.58(m, 1H), 7.55-7.58(m, 3H), 7.81(s, 1H), 7.92-7.97(m, 3H), 8.09(d, J=8.4Hz, 2H), 8.24(d, J=9.3Hz, 1H), 12.60(br s, 1H) |
| A-10 | i-Pr | H | 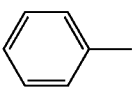 | S | 0.80-0.86(m, 6H), 1.96(m, 1H), 3.58(m, 1H), 7.55-7.58(m, 3H), 7.81(s, 1H), 7.92-7.97(m, 3H), 8.09(d, J=8.4Hz, 2H), 8.24(d, J=9.3Hz, 1H), 12.60(br s, 1H) |
| A-11 | i-Pr | H | 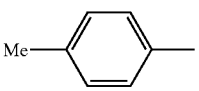 | R | 0.81-0.86(m, 6H), 1.98(m, 1H), 2.39(s, 3H), 3.59(m, 1H), 7.37(d, J=8.1Hz, 2H), 7.77(s, 1H), 7.83(d, J=8.1Hz, 2H), 7.95(d, J=8.4Hz, 2H), 8.08(d, J=8.4Hz, 2H), 8.23(d, J=9.3Hz, 1H), 12.61(br s, 1H) |

TABLE 2

| Example No. | R² | R²' | R⁶ | * | 1H-NMR (DMSO-d₆) |
|---|---|---|---|---|---|
| A-12 | i-Pr | H | 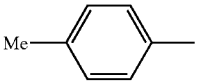 | S | 0.80-0.86(m, 6H), 1.97(m, 1H), 2.39(s, 3H), 3.59(m, 1H), 7.38(d, J=8.1Hz, 2H), 7.78(s, 1H), 7.83(d, J=8.1Hz, 2H), 7.95(d, J=8.4Hz, 2H), 8.09(d, J=8.4Hz, 2H), 8.25(d, J=9.3Hz, 1H), 12.65(br s, 1H) |
| A-13 | i-Pr | H | 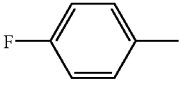 | R | 0.81-0.86(m, 6H), 1.97(m, 1H), 3.85(m, 1H), 7.39-7.46(m, 2H), 7.81(s, 1H), 7.94-8.02(m, 4H), 8.07-8.10(m, 2H), 8.24(d, J=9.3Hz, 1H), 12.64(br s , 1H) |
| A-14 | i-Pr | H | 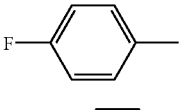 | S | 0.81-0.87(m, 6H), 1.97(m, 1H), 3.58(m, 1H), 7.39-7.47(m, 2H), 7.80(s, 1H), 7.94-8.02(m, 4H), 8.07-8.10(m, 2H), 8.24(d, J=9.3Hz, 1H), 12.65(br s, 1H) |
| A-15 | i-Pr | H | 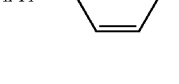 | R | 0.78-0.84(m, 6H), 0.95(t, J=7.5Hz, 3H), 1.67(quint, J=7.5Hz, 2H), 1.95(m, 1H), 2.66(t, J=7.5Hz, 1H), 3.56(br s, 1H), 7.11(s, 1H), 7.89(d, J=8.4Hz, 1H), 8.00(d, J=8.1Hz, 2H), 8.19(d, J=9.0Hz, 1H), 12.64(br s, 1H) |
| A-16 | i-Pr | H | 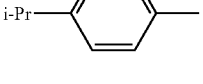 | R | 0.81(d, J=6.9Hz, 3H), 0.85(d, J=6.9Hz, 3H), 1.25(d, J=6.6Hz, 6H), 1.97(m, 1H), 2.97(quint, J=6.9Hz, 1H), 3.57(brs, 1H), 7.44(d, J=8.4Hz, 2H), 7.78(s, 1H), 7.86(d, J=8.7Hz, 2H), 7.95(d, J=8.4Hz, 2H), 8.09(d, J=8.7Hz, 2H), 8.21(brs, 1H), 12.67(brs, 1H) |
| A-17 | i-Pr | H | 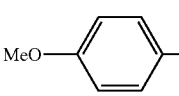 | R | 0.81(d, J=6.9Hz, 3H), 0.85(d, J=6.9Hz, 3H), 1.96(m, 1H), 3.84(s, 3H), 7.12(d, J=8.7Hz, 2H), 7.75(s, 1H), 7.87(d, J=8.7Hz, 2H), 7.94(d, J=8.4Hz, 2H), 8.07(d, J=8.7Hz, 2H), 8.22(br s, 1H), 12.64(br s, 1H) |
| A-18 | i-Pr | H | 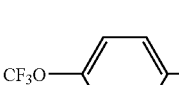 | R | 0.81(d, J=6.9Hz, 3H), 0.85(d, J=6.9Hz, 3H), 1.97(m, 1H), 3.59(m, 1H), 7.59(d, J=8.7Hz, 2H), 7.85(s, 1H), 7.96(d, J=8.4Hz, 2H), 8.05-8.11(m, 4H), 8.24(br s, 1H) |

TABLE 2-continued

| Example No. | R² | R²' | R⁶ | * | 1H-NMR (DMSO-d₆) |
|---|---|---|---|---|---|
| A-19 | i-Pr | H | 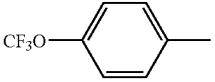 CF₃O—⟨phenyl⟩— | S | 0.81(d, J=6.9Hz, 3H), 0.85(d, J=6.9Hz, 3H), 1.96(m, 1H), 3.84(s, 3H), 7.12(d, J=8.7Hz, 2H), 7.75(s, 1H), 7.87(d, J=8.7Hz, 2H), 7.94(d, J=8.4Hz, 2H), 8.07(d, J=8.7Hz, 2H), 8.22(br s, J=8.7Hz, 2H), 8.24(br s, 1H) |
| A-20 | i-Pr | H | 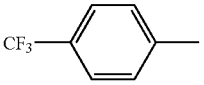 CF₃—⟨phenyl⟩— | R | 0.82(d, J=6.9Hz, 3H), 0.85(d, J=6.9Hz, 3H), 1.97(m, 1H), 3.59(m, 1H), 7.93(s, 1H), 7.96(d, J=8.4Hz, 2H), 7.97(d, J=8.4Hz, 2H), 8.11(d, J=8.4Hz, 2H), 8.17(d, J=7.8Hz, 2H), 8.23(d, J=7.5Hz, 1H), 12.65(br s, 1H) |
| A-21 | i-Pr | H | 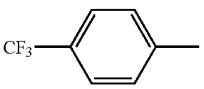 CF₃—⟨phenyl⟩— | S | 0.82(d, J=6.6Hz, 3H), 0.85(d, J=6.9Hz, 3H), 1.97(m, 1H), 3.59(m, 1H), 7.94(s, 1H), 7.93-8.00(m, 4H), 8.11(d, J=8.4Hz, 2H), 8.17(d, J=8.1Hz, 2H), 8.24(m, 1H), 12.60(br s, 1H) |

TABLE 3

| Example No. | R² | R²' | R⁶ | * | 1H-NMR (DMSO-d₆) |
|---|---|---|---|---|---|
| A-22 | i-Pr | H | 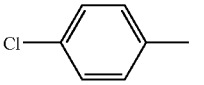 Cl—⟨phenyl⟩— | R | 0.81(d, J=6.9Hz, 3H), 0.85(d, J=6.6Hz, 3H), 1.97(m, 1H), 3.58(m, 1H), 7.65(d, J=8.7Hz, 2H), 7.84(s, 1H), 7.95(d, J=8.7Hz, 2H), 7.96(d, J=8.4Hz, 2H), 8.08(d, J=8.4Hz, 2H), 8.23(d, J=8.7Hz, 1H), 12.65(br s, 1H) |
| A-23 | i-Pr | H | 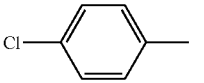 Cl—⟨phenyl⟩— | S | 0.81(d, J=6.6Hz, 3H), 0.85(d, J=6.9Hz, 3H), 1.97(m, 1H), 3.59(m, 1H), 7.66(d, J=8.7Hz, 2H), 7.84(s, 1H), 7.95(d, J=8.7Hz, 2H), 7.96(d, J=8.4Hz, 2H), 8.08(d, J=8.7Hz, 2H), 8.23(d, J=8.1Hz, 1H), 12.60(br s, 1H) |
| A-24 | i-Pr | H |  Br—⟨phenyl⟩— | R | 0.81(d, J=6.6Hz, 3H), 0.85(d, J=6.9Hz, 3H), 1.97(m, 1H), 3.59(m, 1H), 7.79(d, J=8.7Hz, 2H), 7.84(s, 1H), 7.89(d, =8.7Hz, 2H), 7.96(d, J=8.7Hz, 2H), 8.09(d, J=8.4Hz, 2H), 8.24(d, J=8.7Hz, 1H), 12.64(br s, 1H) |
| A-25 | i-Pr | H | 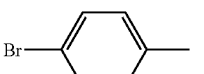 Br—⟨phenyl⟩— | S | 0.81(d, J=6.9Hz, 3H), 0.85(d, J=6.9Hz, 3H), 1.97(m, 1H), 3.58(m, 1H), 7.79(d, J=8.7Hz, 2H), 7.84(s, 1H), 7.89(d, J=8.7Hz, 2H), 7.95(d, J=8.7Hz, 2H), 8.08(d, J=8.7Hz, 2H), 8.23(d, J=8.4Hz, 1H), 12.64(br s, 1H) |
| A-26 | i-Pr | H | 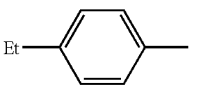 Et—⟨phenyl⟩— | R | 0.81(d, J=6.9Hz, 3H), 0.85(d, J=6.6Hz, 3H), 1.23(t, J=7.8Hz, 3H), 1.97(m, 1H), 2.69(q, J=7.8Hz, 2H), 3.58(m, 1H), 7.41(d, J=8.1Hz, 2H), 7.77(s, 1H), 7.85(d, J=8.4Hz, 2H), 7.95(d, J=8.4Hz, 2H), 8.09(d, J=8.7Hz, 2H), 8.22(m, 1H), 12.64(br s, 1H) |
| A-27 | i-Pr | H | 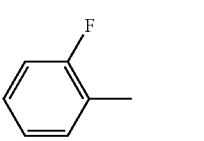 (2-F-phenyl)— | R | 0.82(d, J=6.6Hz, 3H), 0.85(d, J=6.6Hz, 3H), 1.97(m, 1H), 3.59(m, 1H), 7.37-7.51(m, 2H), 7.57-7.67(m, 2H), 7.91-8.00(m, 3H), 8.15(d, J=8.7Hz, 2H), 8.22(d, J=9.3Hz, 1H), 12.63(br s, 1H) |
| A-28 | i-Pr | H | 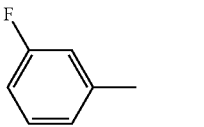 (3-F-phenyl)— | R | 0.82(d, J=6.6Hz, 3H), 0.85(d, J=6.9Hz, 3H), 1.97(m, 1H), 3.59(m, 1H), 7.41(m, 1H), 7.63(m, 1H), 7.73-7.83(m, 2H), 7.86(s, 1H), 7.96(d, J=8.4Hz, 2H), 8.08(d, J=8.4Hz, 2H), 8.22(d, J=8.7Hz, 1H), 12.65(br s, 1H) |

TABLE 3-continued

| Example No. | R² | R²' | R⁶ | * | 1H-NMR (DMSO-d₆) |
|---|---|---|---|---|---|
| A-29 | i-Pr | H | 2-CF₃-phenyl | R | 0.82(d, J=6.6Hz, 3H), 0.85(d, J=6.6Hz, 3H), 1.96(m, 1H), 3.58(m, 1H), 7.48(s, 1H), 7.72-8.01(m, 6H), 8.13(d, J=8.7Hz, 2H), 8.24(d, J=9.9Hz, 1H), 12.61(br s, 1H) |
| A-30 | i-Pr | H | 3-CF₃-phenyl | R | 0.82(d, J=6.9Hz, 3H), 0.85(d, J=6.6Hz, 3H), 1.97(m, 1H), 3.59(m, 1H), 7.83(m, 1H), 7.91-8.01(m, 4H), 8.10(d, J=8.4Hz, 2H), 8.19-8.30(m, 3H), 12.66(br s, 1H) |

TABLE 4

| Example No. | R² | R²' | R⁶ | * | 1H-NMR (DMSO-d₆) |
|---|---|---|---|---|---|
| A-31 | i-Pr | H | 4-HO-phenyl | R | 0.81(d, J=6.9Hz, 3H), 0.85(d, J=6.9Hz, 3H), 1.97(m, 1H), 3.58(m, 1H), 6.92(d, J=8.7Hz, 2H), 7.67(s, 1H), 7.76(d, J=8.7Hz, 2H), 7.94(d, J=8.7Hz, 2H), 8.06(d, J=8.7Hz, 2H), 8.22(d, J=9.3Hz, 1H), 10.00(br s, 1H), 12.64(br s, 1H) |
| A-32 | i-Pr | H | 4-CF₃S-phenyl | R | 0.81(d, J=6.9Hz, 3H), 0.85(d, J=6.9Hz, 3H), 1.97(m, 1H), 3.59(t, J=6.3Hz, 1H), 7.88-7.99(m, 5H), 8.06-8.13(m, 4H), 8.24(d, J=8.7Hz, 1H), 12.61(br s, 1H) |
| A-33 | i-Pr | H | 5-Me-thiophen-2-yl | R | 0.81(d, J=6.6Hz, 3H), 0.85(d, J=6.6Hz, 3H), 1.97(m, 1H), 2.52(s, 3H), 3.59(dd, J=5.4, 9.0Hz, 1H), 6.96(dd, J=1.2, 3.6Hz, 1H), 7.54(d, J=3.6Hz, 1H), 7.68(s, 1H), 7.94(d, J=8.4Hz, 2H), 8.06(d, J=8.4Hz, 2H), 8.24(d, J=9.0Hz, 1H), 12.65(br s, 1H) |
| A-34 | i-Pr | H | 2,4-diF-phenyl | R | 0.80-0.85(m, 6H), 1.96(m, 1H), 3.58(m, 1H), 7.45-7.60(m, 2H), 7.70(s, 1H), 7.78(m, 1H), 7.95(d, J=8.7Hz, 2H), 8.15(d, J=8.7Hz, 2H), 8.23(m, 1H) |
| A-35 | i-Pr | H | 2,4-diF-phenyl | S | 0.80-0.85(m, 6H), 1.96(m, 1H), 3.58(m, 1H), 7.45-7.60(m, 2H), 7.70(s, 1H), 7.78(m, 1H), 7.95(d, J=8.7Hz, 2H), 8.15(d, J=8.7Hz, 2H), 8.23(m, 1H) |
| A-36 | i-Pr | H | 3,4-diF-phenyl | R | 0.81(d, J=6.6Hz, 3H), 0.85(d, J=6.9Hz, 3H), 1.98(m, 1H), 3.59(dd, J=6.5, 8.9Hz, 1H), 7.67(m, 1H), 7.82(brm, 1H), 7.84(s, 1H), 7.96(d, J=8.7Hz, 2H), 8.01(dd, J=2.3, 3.8Hz, 1H), 8.06(d, J=8.7Hz, 2H), 8.23(d, J=9.0Hz, 1H) |
| A-37 | i-Pr | H | 3,4-diF-phenyl | S | 0.81(d, J=6.9Hz, 3H), 0.85(d, J=6.9Hz, 3H), 1.97(m, 1H), 3.59(brm, 1H), 7.67(m, 1H), 7.81(brm, 1H), 7.84(s, 1H), 7.96(d, J=8.4Hz, 2H), 8.01(dd, J=2.1, 3.6Hz, 1H), 8.07(d, J=8.4Hz, 2H), 8.23(d, J=9.3Hz, 1H) |

TABLE 4-continued

| Example No. | $R^2$ | $R^{2'}$ | $R^6$ | * | 1H-NMR (DMSO-$d_6$) |
|---|---|---|---|---|---|
| A-38 | i-Pr | H | 3-F-4-MeO-phenyl | R | 0.81(d, J=6.9Hz, 3H), 0.85(d, J=6.9Hz, 3H), 1.97(m, 1H), 3.58(brm, 1H), 3.93(s, 3H), 7.36(t, J=9.0Hz, 1H), 7.72-7.79(m, 3H), 7.95(d, J=8.7Hz, 2H), 8.06(d, J=8.7Hz, 2H), 8.22(brd, J=8.7Hz, 1H) |
| A-39 | i-Pr | H | 3-F-4-MeO-phenyl | S | 0.81(d, J=6.9Hz, 3H), 0.85(d, J=6.9Hz, 3H), 1.97(m, 1H), 3.58(brm, 1H), 3.93(s, 3H), 7.37(t, J=8.9Hz, 1H), 7.73-7.80(m, 3H), 7.95(d, J=8.4Hz, 2H), 8.06(d, J=8.7Hz, 2H), 8.22(brd, J=8.4Hz, 1H) |
| A-40 | i-Pr | H | 3-F-4-Cl-phenyl | R | 0.81(d, J=6.9Hz, 3H), 0.85(d, J=6.9Hz, 3H), 1.97(m, 1H), 3.58(brm, 1H), 7.81-7.83(m, 2H), 7.87(s, 1H), 7.94-7.99(m, 3H), 8.06(d, J=8.7Hz, 2H), 8.2(brd, J=8.1Hz, 1H) |

TABLE 5

| Example No. | $R^2$ | $R^{2'}$ | $R^6$ | * | 1H-NMR (DMSO-$d_6$) |
|---|---|---|---|---|---|
| A-41 | i-Pr | H | 3-F-4-Cl-phenyl | S | 0.81(d, J=6.6Hz, 3H), 0.85(d, J=6.6Hz, 3H), 1.97(m, 1H), 3.58(brm, 1H), 7.81-7.83(m, 2H), 7.88(s, 1H), 7.94-8.00(m, 3H), 8.07(d, J=8.7Hz, 2H), 8.23(brd, J=8.1Hz, 1H) |
| A-42 | i-Pr | H | 3-F-4-Me-phenyl | R | 0.81(d, J=6.6Hz, 3H), 0.85(d, J=6.6Hz, 3H), 1.97(m, 1H), 2.32(d, J=1.5Hz, 3H), 3.59(brm, 1H), 7.49(t, J=7.8Hz, 1H), 7.69(d, J=9.3Hz, 2H), 7.82(s, 1H), 7.96(d, J=8.7Hz, 2H), 8.07(d, J=8.7Hz, 2H), 8.22(brd, J=7.2Hz, 1H) |
| A-43 | i-Pr | H | 3-Cl-4-Cl-phenyl | R | 0.81(d, J=6.9Hz, 3H), 0.85(d, J=6.9Hz, 3H), 1.97(m, 1H), 3.59(m, 1H), 7.86(d, J=8.4Hz, 1H), 7.91(s, 1H), 7.94(dd, J=1.8, 8.4Hz, 1H), 7.96(d, J=8.1Hz, 2H), 8.07(d, J=8.7Hz, 2H), 8.19(d, J=2.1Hz, 1H), 8.22(m, 1H), 12.60(br s, 1H) |
| A-44 | i-Pr | H | 3-MeO-4-MeO-phenyl | R | 0.81(d, J=6.9Hz, 3H), 0.85(d, J=6.9Hz, 3H), 1.97(m, 1H), 3.58(m, 1H), 3.84(s, 3H), 3.86(s, 3H), 7.13(d, J=8.4Hz, 1H), 7.44-7.54(m, 2H), 7.78(s, 1H), 7.95(d, J=8.4Hz, 2H), 8.07(d, J=8.4Hz, 2H), 8.23(m, 1H), 12.60(br s, 1H) |
| A-45 | i-Pr | H | 3,5-di-F-phenyl | R | 0.81(d, J=6.9Hz, 3H), 0.85(d, J=6.9Hz, 3H), 1.97(m, 1H), 3.59(m, 1H), 7.49(m, 1H), 7.63-7.73(m, 2H), 7.89(s, 1H), 7.97(d, J=8.7Hz, 2H), 8.06(d, J=8.7Hz, 2H), 8.24(d, J=9.9Hz, 1H), 12.67(br s, 1H) |
| A-46 | i-Pr | H | 2-F-4-MeO-phenyl | R | 0.81(d, J=6.9Hz, 3H), 0.85(d, J=6.9Hz, 3H), 1.97(m, 1H), 3.58(m, 1H), 3.86(s, 3H), 6.98(m, 1H), 7.08(m, 1H), 7.59(d, J=2.7Hz, 1H), 7.88(t, J=8.7Hz, 1H), 7.93(d, J=8.7Hz, 2H), 8.13(d, J=8.7Hz, 2H), 8.23(m, 1H), 12.65(br s, 1H) |

TABLE 5-continued

| Example No. | R² | R²' | R⁶ | * | 1H-NMR (DMSO-d₆) |
|---|---|---|---|---|---|
| A-47 | i-Pr | H | 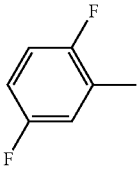 | R | 0.81(d, J=6.9Hz, 3H), 0.85(d, J=6.6Hz, 3H), 1.97(m, 1H), 3.58(m, 1H), 7.45-7.59(m, 2H), 7.70(s, J=2.7Hz, 1H), 7.78(m, 1H), 7.94(d, J=8.7Hz, 2H), 8.14(d, J=8.7Hz, 2H), 8.22(d, J=9.0Hz, 1H), 12.67(br s, 1H) |
| A-48 | i-Pr | H | 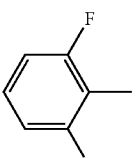 | R | 0.81(d, J=6.6Hz, 3H), 0.84(d, J=6.9Hz, 3H), 1.96(m, 1H), 3.57(m, 1H), 7.32-7.42(m, 2H), 7.59(s, 1H), 7.69(m, 1H), 7.94(d, J=8.7Hz, 2H), 8.15(d, J=8.4Hz, 2H), 8.23(d, J=6.9Hz, 1H), 12.65(br s, 1H) |
| A-49 | i-Pr | H |  | R | 0.81(d, J=6.9Hz, 3H), 0.85(d, J=6.9Hz, 3H), 1.97(m, 1H), 3.59(m, 1H), 3.84(s, 3H), 7.16(m, 1H), 7.35-7.46(m, 2H), 7.67(d, J=2.7Hz, 1H), 7.94(d, J=8.4Hz, 2H), 8.14(d, J=8.4Hz, 2H), 8.24(d, J=9.9Hz, 1H), 12.63(br s, 1H) |

TABLE 6

| Example No. | R² | R²' | R⁶ | * | 1H-NMR (DMSO-d₆) |
|---|---|---|---|---|---|
| A-50 | i-Pr | H | 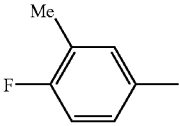 | R | 0.81(d, J=6.9Hz, 3H), 0.85(d, J=6.6Hz, 3H), 1.97(m, 1H), 2.34(s, 3H), 3.59(t, J=6.0Hz, 1H), 7.34(t, J=8.7Hz, 1H), 7.78(s, 1H), 7.81(m, 1H), 7.89(dd, J=1.8, 7.5Hz, 1H), 7.95(d, J=8.4Hz, 2H), 8.07(d, J=8.4Hz, 2H), 8.22(d, J=8.7Hz, 1H), 12.63(br s, 1H) |
| A-51 | i-Pr | H | 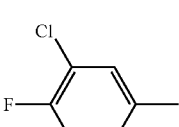 | R | 0.81(d, J=6.6Hz, 3H), 0.85(d, J=6.6Hz, 3H), 1.97(m, 1H), 3.59(m, 1H), 7.65(m, 1H), 7.88(s, 1H), 7.94-8.01(m, 3H), 8.06(d, J=8.4Hz, 2H), 8.16(m, 1H), 8.23(br s, 1H), 12.62(br s, 1H) |
| A-52 | i-Pr | H | 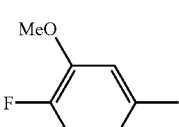 | R | 0.82(d, J=6.6Hz, 3H), 0.85(d, J=6.9Hz, 3H), 1.97(m, 1H), 3.59(m, 1H), 3.96(s, 3H), 7.42(dd, J=8.4, 11.4Hz, 1H), 7.53(ddd, J=2.1, 4.5, 8.4Hz, 1H), 7.68(dd, J=2.1, 8.4Hz, 1H), 7.96(d, J=8.4Hz, 2H), 8.08(d, J=8.4Hz, 2H), 8.23(d, J=9.3Hz, 1H), 12.64(br s, 1H) |
| A-53 | i-Pr | H | 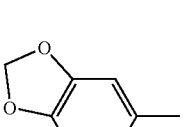 | S | 0.81(d, J=6.9Hz, 3H), 0.85(d, J=6.6Hz, 3H), 1.97(m, 1H), 3.58(m, 1H), 6.13(s, 2H), 7.11(d, J=8.7Hz, 1H), 7.43-7.49(m, 2H), 7.74(s, 1H), 7.94(d, J=8.7Hz, 2H), 8.05(d, J=8.7Hz, 2H), 8.22(d, J=9.6Hz, 1H), 12.67(br s, 1H) |
| A-54 | i-Pr | H | 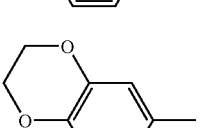 | S | 0.81(d, J=6.6Hz, 3H), 0.85(d, J=6.9Hz, 3H), 1.97(m, 1H), 3.60(m, 1H), 4.32(s, 4H), 7.03(d, J=9.0Hz, 1H), 7.39-7.44(m, 2H), 7.73(s, 1H), 7.94(d, J=8.4Hz, 2H), 8.05(d, J=8.7Hz, 2H), 8.22(d, J=8.4Hz, 1H), 12.63(br s, 1H) |
| A-55 | i-Pr | H | 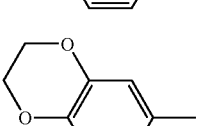 | R | 0.81(d, J=6.9Hz, 3H), 0.85(d, J=6.6Hz, 3H), 1.96(m, 1H), 3.58(m, 1H), 4.32(s, 4H), 7.03(d, J=9.0Hz, 1H), 7.38-7.45(m, 2H), 7.73(s, 1H), 7.94(d, J=8.7Hz, 2H), 8.05(d, J=8.4Hz, 2H), 8.22(d, J=9.3Hz, 1H), 12.63(br s, 1H) |

TABLE 6-continued

| Example No. | R² | R²' | R⁶ | * | 1H-NMR (DMSO-d₆) |
|---|---|---|---|---|---|
| A-56 | i-Pr | H | 3-Cl-4-MeO-phenyl | R | 0.81(d, J=6.6Hz, 3H), 0.85(d, J=6.9Hz, 3H), 1.97(m, 1H), 3.58(m, 1H), 3.95(s, 3H), 7.35(d, J=8.7Hz, 1H), 7.83(s, 1H), 7.90(dd, J=2.1, 8.7Hz, 1H), 7.95(d, J=8.7Hz, 2H), 7.99(d, J=2.4Hz, 1H), 8.06(d, J=8.7Hz, 2H), 8.23(d, J=9.3Hz, 1H), 12.64(br s, 1H) |
| A-57 | i-Pr | H | 3-Br-4-MeO-phenyl | R | 0.81(d, J=6.9Hz, 3H), 0.85(d, J=6.9Hz, 3H), 1.97(m, 1H), 3.59(m, 1H), 3.94(s, 3H), 7.31(d, J=8.7Hz, 1H), 7.89(s, 1H), 7.92-7.98(m, 3H), 8.06(d, J=8.4Hz, 2H), 8.14(d, J=2.1Hz, 1H), 8.24(d, J=9.3Hz, 1H), 12.64(br s, 1H) |

TABLE 7

| Example No. | R² | R²' | R⁶ | * | 1H-NMR (DMSO-d₆) |
|---|---|---|---|---|---|
| A-58 | i-Bu | H | phenyl | R | 0.74(d, J=6.3Hz, 3H), 0.83(d, J=6.6Hz, 3H), 1.34-1.51(m, 2H), 1.61(m, 1H), 3.73(m, 1H), 7.55-7.60(m, 3H), 7.81(s, 1H), 7.92-7.96(m, 4H), 8.10(d, J=8.4Hz, 2H), 8.35(d, J=9.0Hz, 1H), 12.63(br s, 1H) |
| A-59 | i-Bu | H | phenyl | S | 0.74(d, J=6.6Hz, 3H), 0.83(d, J=6.6Hz, 3H), 1.33-1.51(m, 2H), 1.61(m, 1H), 3.73(m, 1H), 7.51-7.62(m, 3H), 7.82(s, 1H), 7.90-7.98(m, 4H), 8.10(d, J=8.4Hz, 2H), 8.35(d, J=7.5Hz, 1H), 12.65(br s, 1H) |
| A-60 | i-Bu | H | 4-Me-phenyl | R | 0.74(d, J=6.6Hz, 3H), 0.83(d, J=6.6Hz, 3H), 1.39-1.57(m, 2H), 1.61(m, 1H), 3.73(m, 1H), 7.38(d, J=8.1Hz, 2H), 7.78(s, 1H), 7.83(d, J=8.1Hz, 2H), 7.94(d, J=8.4Hz, 2H), 8.10(d, J=8.7Hz, 1H), 8.36(d, J=8.1Hz, 1H), 12.70(br s, 1H) |
| A-61 | i-Bu | H | 4-Me-phenyl | S | 0.73(d, J=6.6Hz, 3H), 0.83(d, J=6.6Hz, 3H), 1.33-1.50(m, 2H), 1.61(m, 1H), 2.39(s, 3H), 3.72(m, 1H), 7.38(d, J=8.4Hz, 2H), 7.77(s, 1H), 7.83(d, J=8.1Hz, 2H), 7.94(d, J=8.1Hz, 2H), 8.09(d, J=8.7Hz, 2H), 8.35(d, J=7.8Hz, 1H), 12.64(br s, 1H) |
| A-62 | i-Bu | H | 4-CF₃-phenyl | R | 0.74(d, J=6.3Hz, 3H), 0.83(d, J=6.6Hz, 3H), 1.33-1.52(m, 2H), 1.61(m, 1H), 3.73(m, 1H), 7.93(s, 1H), 7.93-7.99(m, 4H), 8.12(d, J=8.7Hz, 2H), 8.32(d, J=8.1Hz, 2H), 8.35(d, J=7.2Hz, 1H), 12.65(br s, 1H) |
| A-63 | i-Bu | H | 4-CF₃-phenyl | S | 0.74(d, J=6.6Hz, 3H), 0.83(d, J=6.9Hz, 3H), 1.33-1.51(m, 2H), 1.61(m, 1H), 3.72(m, 1H), 7.92-8.00(m, 5H), 8.12(d, J=8.1Hz, 2H), 8.17(d, J=8.1Hz, 2H), 8.36(m, 1H), 12.67(br s, 1H) |
| A-64 | i-Bu | H | 4-Cl-phenyl | R | 0.73(d, J=6.6Hz, 3H), 0.83(d, J=6.6Hz, 3H), 1.33-1.50(m, 2H), 1.62(m, 1H), 3.72(m, 1H), 7.66(d, J=8.4Hz, 2H), 7.84(s, 1H), 7.95(d, J=8.7Hz, 2H), 7.97(d, J=8.4Hz, 2H), 8.09(d, J=8.4Hz, 2H), 8.35(m, 1H) |
| A-65 | i-Bu | H | 4-Cl-phenyl | S | 0.73(d, J=6.3Hz, 3H), 0.83(d, J=6.6Hz, 3H), 1.33-1.51(m, 2H), 1.60(m, 1H), 3.73(m, 1H), 7.65(d, J=8.7Hz, 2H), 7.84(s, 1H), 7.95(d, J=8.7Hz, 2H), 7.96(d, J=8.7Hz, 2H), 8.09(d, J=8.7Hz, 2H), 8.36(d, J=9.0Hz, 1H), 12.66(br s, 1H) |

TABLE 7-continued

| Example No. | R² | R²' | R⁶ | * | 1H-NMR (DMSO-d₆) |
|---|---|---|---|---|---|
| A-66 | i-Bu | H | 4-Br-phenyl | S | 0.73(d, J=6.3Hz, 3H), 0.83(d, J=6.6Hz, 3H), 1.33-1.50(m, 2H), 1.61(m, 1H), 3.71(m, 1H), 7.79(d, J=8.4Hz, 2H), 7.84(s, 1H), 7.89(d, J=8.7Hz, 2H), 7.94(d, J=8.4Hz, 2H), 8.09(d, J=8.4Hz, 2H), 8.35(d, J=8.7Hz, 1H), 12.65(br s, 1H) |

TABLE 8

| Example No. | R² | R²' | R⁶ | * | 1H-NMR (DMSO-d₆) |
|---|---|---|---|---|---|
| A-67 | i-Bu | H | 4-Br-phenyl | R | 0.73(d, J=6.6Hz, 3H), 0.83(d, J=6.6Hz, 3H), 1.33-1.50(m, 2H), 1.61(m, 1H), 3.72(m, 1H), 7.79(d, J=8.4Hz, 2H), 7.84(s, 1H), 7.89(d, J=8.7Hz, 2H), 7.94(d, J=8.4Hz, 2H), 8.09(d, J=8.4Hz, 2H), 8.35(m, 1H), 12.62(br s, 1H) |
| A-68 | i-Bu | H | 4-F-phenyl | S | 0.74(d, J=6.6Hz, 3H), 0.83(d, J=6.6Hz, 3H), 1.33-1.51(m, 2H), 1.61(m, 1H), 3.73(m, 1H), 7.38-7.48(m, 2H), 7.82(s, 1H), 7.95(d, J=8.7Hz, 2H), 7.96-78.04(m, 2H), 8.09(d, J=8.4Hz, 2H), 8.36(d, J=8.4Hz, 1H), 12.65(br s, 1H) |
| A-69 | i-Bu | H | 4-F-phenyl | R | 0.74(d, J=6.6Hz, 3H), 0.83(d, J=6.6Hz, 3H), 1.33-1.51(m, 2H), 1.61(m, 1H), 3.73(m, 1H), 7.37-7.48(m, 2H), 7.81(s, 1H), 7.95(d, J=8.7Hz, 2H), 7.96-8.04(m, 2H), 8.09(d, J=8.4Hz, 2H), 8.34(d, J=7.8Hz, 1H), 12.63(br s, 1H) |
| A-70 | i-Bu | H | 2-F-phenyl | R | 0.74(d, J=6.6Hz, 3H), 0.83(d, J=6.3Hz, 3H), 1.33-1.51(m, 2H), 1.61(m, 1H), 3.73(m, 1H), 7.37-7.52(m, 2H), 7.58-7.69(m, 2H), 7.90-8.01(m, 3H), 8.16(d, J=8.7Hz, 2H), 8.36(d, J=8.1Hz, 1H), 12.63(br s, 1H) |
| A-71 | i-Bu | H | 3-F-phenyl | R | 0.74(d, J=6.6Hz, 3H), 0.83(d, J=6.6Hz, 3H), 1.33-1.51(m, 2H), 1.61(m, 1H), 3.73(m, 1H), 7.41(m, 1H), 7.63(m, 1H), 7.73-7.83(m, 2H), 7.86(s, 1H), 7.95(d, J=8.4Hz, 2H), 8.09(d, J=8.7Hz, 2H), 8.35(m, 1H), 12.63(br s, 1H) |
| A-72 | i-Bu | H | 2-CF₃-phenyl | R | 0.75(d, J=6.3Hz, 3H), 0.84(d, J=6.6Hz, 3H), 1.33-1.50(m, 2H), 1.62(m, 1H), 3.73(m, 1H), 7.48(s, 1H), 7.73-.01(m, 4H), 7.93(d, J=8.7Hz, 2H), 8.14(d, J=8.7Hz, 2H), 8.35(d, J=7.5Hz, 1H), 12.66(br s, 1H) |
| A-73 | i-Bu | H | 4-CF₃S-phenyl | R | 0.74(d, J=6.3Hz, 3H), 0.84(d, J=6.6Hz, 3H), 1.34-1.51(m, 2H), 1.61(m, 1H), 3.73(m, 1H), 7.89-7.99(m, 5H), 8.07-8.14(m, 4H), 8.37(d, J=7.5Hz, 1H), 12.66(br s, 1H) |
| A-74 | i-Bu | H | 4-Et-phenyl | R | 0.74(d, J=6.6Hz, 3H), 0.83(d, J=6.3Hz, 3H), 1.23(t, J=7.5Hz, 3H), 1.33-1.50(m, 2H), 1.61(m, 1H), 2.69(q, J=7.5Hz, 2H), 3.72(m, 1H), 7.41(d, J=8.1Hz, 2H), 7.78(s, 1H), 7.85(d, J=8.4Hz, 2H), 7.94(d, J=8.7Hz, 2H), 8.09(d, J=8.7Hz, 2H), 8.34(d, J=7.5Hz, 1H), 12.64(br s, 1H) |
| A-75 | i-Bu | H | 2,4-diF-phenyl | R | 0.74(d, J=6.6Hz, 3H), 0.83(d, J=6.6Hz, 3H), 1.38-1.45(m, 2H), 1.60(m, 1H), 3.72(m, 1H), 7.44-7.60(m, 2H), 7.70(d, J=2.4Hz, 1H), 7.79(m, 1H), 7.94(d, J=8.4Hz, 2H), 8.16(d, J=8.4Hz, 2H), 8.34(br s, 1H), 12.65(br s, 1H) |

TABLE 9

| Example No. | R² | R²' | R⁶ | * | 1H-NMR (DMSO-d₆) |
|---|---|---|---|---|---|
| A-76 | i-Bu | H | 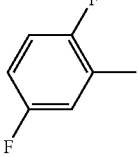 | S | 0.74(d, J=6.6Hz, 3H), 0.83(d, J=6.6Hz, 3H), 1.33-1.50(m, 2H), 1.61(m, 1H), 3.72(m, 1H), 7.44-7.60(m, 2H), 7.71(d, J=2.4Hz, 1H), 7.79(m, 1H), 7.94(d, J=8.7Hz, 2H), 8.16(d, J=8.7Hz, 2H), 8.36(d, J=8.4Hz, 1H), 12.65(br s, 1H) |
| A-77 | i-Bu | H | 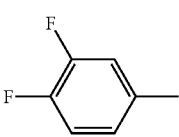 | R | 0.74(d, J=6.6Hz, 3H), 0.83(d, J=6.6Hz, 3H), 1.33-1.50(m, 2H), 1.60(m, 1H), 3.72(m, 1H), 7.69(m, 1H), 7.80-7.85(m, 2H), 7.95(d, J=9.0Hz, 2H), 8.01(m, 1H), 8.07(d, J=8.7Hz, 2H), 8.34(d, J=8.4Hz, 1H), 12.65(br s, 1H) |
| A-78 | i-Bu | H | 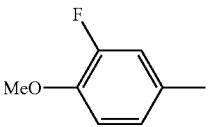 | R | 0.73(d, J=6.3Hz, 3H), 0.83(d, J=6.3Hz, 3H), 1.41(m, 2H), 1.60(m, 1H), 3.71(brm, 1H), 3.92(s, 3H), 7.37(t, J=9.0Hz, 1H), 7.75-7.79(m, 3H), 7.94(d, J=8.7Hz, 2H), 8.06(d, J=9.0Hz, 2H), 8.33(brd, J=7.2Hz, 1H) |
| A-79 | i-Bu | H | 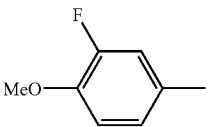 | S | 0.73(d, J=6.6Hz, 3H), 0.83(d, J=6.6Hz, 3H), 1.33-1.50(m, 2H), 1.61(m, 1H), 3.71(m, 1H), 3.93(s, 3H), 7.37(m, 1H), 7.72-7.78(m, 2H), 7.79(s, 1H), 7.94(d, J=8.4Hz, 2H), 8.07(d, J=8.4Hz, 2H), 8.35(m, 1H), 12.63(br s, 1H) |
| A-80 | i-Bu | H | 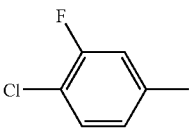 | R | 0.73(d, J=6.6Hz, 3H), 0.83(d, J=6.6Hz, 3H), 1.33-1.50(m, 2H), 1.61(m, 1H), 3.72(m, 1H), 7.81-7.84(m, 2H), 7.88(s, 1H), 7.97(t, J=8.4Hz, 3H), 8.07(d, J=9.0Hz, 2H), 8.35(m, 1H) |
| A-81 | i-Bu | H | 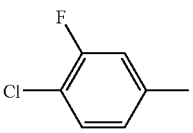 | S | 0.73(d, J=6.3Hz, 3H), 0.83(d, J=6.6Hz, 3H), 1.33-1.50(m, 2H), 1.60(m, 1H), 3.72(m, 1H), 7.79-7.88(m, 2H), 7.88(s, 1H), 7.92-8.01(m, 3H), 8.07(d, J=8.7Hz, 2H), 8.36(d, J=7.5Hz, 1H), 12.65(br s, 1H) |
| A-82 | i-Bu | H | 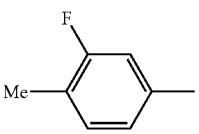 | R | 0.73(d, J=6.3Hz, 3H), 0.83(d, J=6.6Hz, 3H), 1.42(m, 2H), 1.59(m, 1H), 2.32(d, J=1.5Hz, 3H), 3.72(brm, 1H), 7.49(t, J=7.8Hz, 1H), 7.70(d, J=9.3Hz, 2H), 7.82(s, 1H), 7.95(d, J=8.7Hz, 2H), 8.08(d, J=8.4Hz, 2H), 8.34(brd, J=7.8Hz, 1H) |
| A-83 | i-Bu | H | 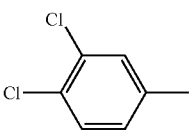 | R | 0.73(d, J=6.6Hz, 3H), 0.83(d, J=6.6Hz, 3H), 1.33-1.51(m, 2H), 1.60(m, 1H), 3.73(m, 1H), 7.86(d, J=8.4Hz, 1H), 7.91(s, 1H), 7.94(dd, J=2.1, 8.4Hz, 1H), 7.96(d, J=8.7Hz, 2H), 8.08(d, J=8.7Hz, 2H), 8.19(d, J=1.8Hz, 1H), 8.35(m, 1H) |

TABLE 10

| Example No. | R² | R²' | R⁶ | * | 1H-NMR (DMSO-d₆) |
|---|---|---|---|---|---|
| A-84 | i-Bu | H | 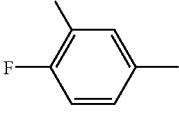 | S | 0.74(d, J=6.6Hz, 3H), 0.83(d, J=6.6Hz, 3H), 1.33-1.51(m, 2H), 1.61(m, 1H), 3.72(m, 1H), 7.32-7.42(m, 2H), 7.59(s, 1H), 7.69(m, 1H), 7.93(d, J=8.4Hz, 2H), 8.15(d, J=8.7Hz, 2H), 8.35(d, J=6.6Hz, 1H), 12.66(br s, 1H) |
| A-85 | i-Bu | H | 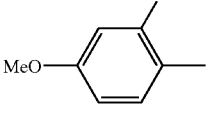 | R | 0.73(d, J=6.3Hz, 3H), 0.83(d, J=6.6Hz, 3H), 1.33-1.50(m, 2H), 1.61(m, 1H), 3.72(m, 1H), 3.86(s, 3H), 6.98(m, 1H), 7.08(m, 1H), 7.59(d, J=2.7Hz, 1H), 7.84-7.96(m, 3H), 8.14(d, J=8.7Hz, 2H), 8.35(m, 1H), 12.61(br s, 1H) |

TABLE 10-continued

| Example No. | R² | R²' | R⁶ | * | 1H-NMR (DMSO-d₆) |
|---|---|---|---|---|---|
| A-86 | i-Bu | H | 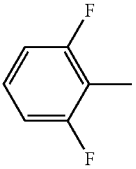 | R | 0.74(d, J=6.6Hz, 3H), 0.83(d, J=6.6Hz, 3H), 1.33-1.51(m, 2H), 1.61(m, 1H), 3.72(m, 1H), 7.32-7.42(m, 2H), 7.59(s, 1H), 7.69(m, 1H), 7.93(d, J=8.4Hz, 2H), 8.15(d, J=8.7Hz, 2H), 8.35(d, J=6.6Hz, 1H), 12.66(br s, 1H) |
| A-87 | i-Bu | H | 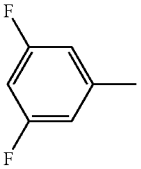 | R | 0.74(d, J=6.3Hz, 3H), 0.83(d, J=6.3Hz, 3H), 1.33-1.50(m, 2H), 1.61(m, 1H), 3.72(m, 1H), 7.49(m, 1H), 7.63-7.74(m, 2H), 7.90(s, 1H), 7.96(d, J=8.7Hz, 2H), 8.07(d, J=8.7Hz, 2H), 8.35(m, 1H), 12.60(br s, 1H) |
| A-88 | i-Bu | H | 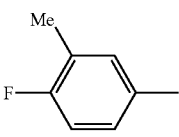 | R | 0.74(d, J=6.6Hz, 3H), 0.83(d, J=6.6Hz, 3H), 1.34-1.50(m, 2H), 1.61(m, 1H), 2.33(s, 3H), 3.73(m, 1H), 7.34(t, J=8.7Hz, 1H), 7.79(s, 1H), 7.80(m, 1H), 7.89(d, J=7.5Hz, 1H), 7.95(d, J=8.4Hz, 2H), 8.08(d, J=8.4Hz, 2H), 8.34(d, J=7.8Hz, 1H), 12.62(br s, 1H) |
| A-89 | i-Bu | H | 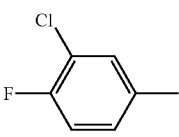 | R | 0.74(d, J=6.6Hz, 3H), 0.83(d, J=6.6Hz, 3H), 1.34-1.50(m, 2H), 1.61(m, 1H), 3.72(m, 1H), 7.64(m, 1H), 7.88(s, 1H), 7.93-8.01(m, 3H), 8.07(d, J=8.1Hz, 2H), 8.16(m, 1H), 8.34(br s, 1H), 12.83(br s, 1H) |
| A-90 | i-Bu | H | 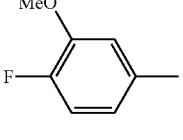 | R | 0.74(d, J=6.6Hz, 3H), 0.84(d, J=6.6Hz, 3H), 1.35-1.51(m, 2H), 1.61(m, 1H), 3.73(m, 1H), 3.96(s, 3H), 7.42(dd, J=8.4, 11.1Hz, 1H), 7.53(ddd, J=2.1, 4.5, 8.4Hz, 1H), 7.68(dd, J=2.1, 8.4Hz, 1H), 7.96(d, J=8.4Hz, 2H), 8.09(d, J=8.4Hz, 2H), 8.36(d, J=8.4Hz, 1H), 12.65(br s, 1H) |
| A-91 | i-Bu | H | 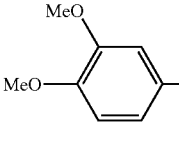 | R | 0.73(d, J=6.6Hz, 3H), 0.83(d, J=6.6Hz, 3H), 1.33-1.50(m, 2H), 1.60(m, 1H), 3.73(m, 1H), 3.84(s, 3H), 3.87(s, 3H), 7.13(d, J=8.7Hz, 1H), 7.46-7.53(m, 2H), 7.79(s, 1H), 7.94(d, J=8.7Hz, 2H), 8.08(d, J=8.7Hz, 2H), 8.35(m, 1H), 12.63(br s, 1H) |

TABLE 11

| Example No. | R² | R²' | R⁶ | * | 1H-NMR (DMSO-d₆) |
|---|---|---|---|---|---|
| A-92 | i-Bu | H | 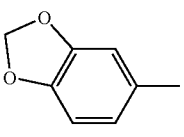 | R | 0.73(d, J=6.6Hz, 3H), 0.83(d, J=6.6Hz, 3H), 1.33-1.50(m, 2H), 1.60(m, 1H), 3.73(m, 1H), 6.14(s, 2H), 7.11(d, J=8.7Hz, 1H), 7.44-7.50(m, 2H), 7.74(s, 1H), 7.94(d, J=8.7Hz, 2H), 8.06(d, J=8.4Hz, 2H), 8.35(d, J=8.1Hz, 1H), 12.64(br s, 1H) |
| A-93 | i-Bu | H | 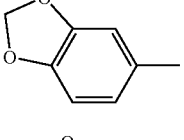 | S | 0.73(d, J=6.6Hz, 3H), 0.83(d, J=6.6Hz, 3H), 1.33-1.50(m, 2H), 1.60(m, 1H), 3.73(m, 1H), 6.13(s, 2H), 7.11(d, J=8.7Hz, 1H), 7.44-7.49(m, 2H), 7.74(s, 1H), 7.94(d, J=8.7Hz, 2H), 8.06(d, J=8.4Hz, 2H), 8.34(d, J=9.9Hz, 1H), 12.61(br s, 1H) |
| A-94 | i-Bu | H | 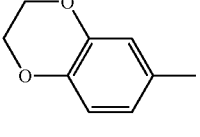 | R | 0.73(d, J=6.6Hz, 3H), 0.83(d, J=6.3Hz, 3H), 1.33-1.50(m, 2H), 1.60(m, 1H), 3.73(m, 1H), 4.32(s, 4H), 7.03(d, J=8.7Hz, 1H), 7.39-7.45(m, 2H), 7.74(s, 1H), 7.93(d, J=8.7Hz, 2H), 8.06(d, J=8.7Hz, 2H), 8.34(d, J=7.5Hz, 1H), 12.63(br s, 1H) |

TABLE 11-continued

| Example No. | R² | R²' | R⁶ | * | 1H-NMR (DMSO-d₆) |
|---|---|---|---|---|---|
| A-95 | i-Bu | H | 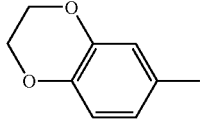 | S | 0.73(d, J=6.3Hz, 3H), 0.83(d, J=6.6Hz, 3H), 1.33-1.50(m, 2H), 1.61(m, 1H), 3.72(m, 1H), 4.32(s, 4H), 7.03(d, J=9.0Hz, 1H), 7.39-7.44(m, 2H), 7.74(s, 1H), 7.93(d, J=8.7Hz, 2H), 8.07(d, J=8.7Hz, 2H), 8.35(d, J=9.3Hz, 1H), 12.64(br s, 1H) |
| A-96 | i-Bu | H | 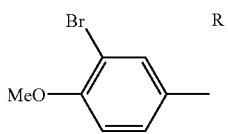 | R | 0.73(d, J=6.3Hz, 3H), 0.83(d, J=6.3Hz, 3H), 1.33-1.50(m, 2H), 1.61(m, 1H), 3.71(m, 1H), 3.94(s, 3H), 7.31(d, J=8.7Hz, 1H), 7.84(s, 2H), 7.91-7.98(m, 3H), 8.07(d, J=8.4Hz, 2H), 8.14(d, J=2.4Hz, 1H), 8.34(d, J=7.8Hz, 1H), 12.64(br s, 1H) |
| A-97 | i-Bu | H | 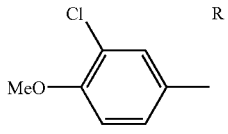 | R | 0.73(d, J=6.3Hz, 3H), 0.83(d, J=6.6Hz, 3H), 1.33-1.50(m, 2H), 1.61(m, 1H), 3.73(m, 1H), 3.95(s, 3H), 7.35(d, J=8.7Hz, 1H), 7.83(s, 1H), 7.90(dd, J=2.1, 8.7Hz, 1H), 7.94(d, J=8.7Hz, 2H), 7.99(d, J=2.1Hz, 1H), 8.07(d, J=8.7Hz, 2H), 8.34(d, J=8.1Hz, 1H), 12.67(br s, 1H) |
| A-98 | s-Bu | H | 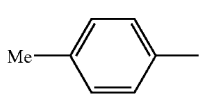 | S | 0.75-0.84(m, 6H), 1.12(m, 1H), 1.38(m, 1H), 1.70(m, 1H), 2.39(s, 3H), 3.62(m, 1H), 7.38(d, J=8.1Hz, 2H), 7.77(s, 1H), 7.83(d, J=8.1Hz, 2H), 7.95(d, J=8.7Hz, 2H), 8.09(d, J=8.4Hz, 2H), 8.26(brs, 1H) |
| A-99 | s-Bu | H | 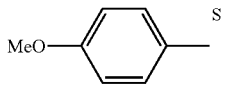 | S | 0.75-0.84(m, 6H), 1.12(m, 1H), 1.38(m, 1H), 1.72(m, 1H), 3.62(m, 1H), 3.84(s, 1H), 7.12(d, J=9.0Hz, 2H), 7.74(s, 1H), 7.88(d, J=8.7Hz, 2H), 7.94(d, J=8.7Hz, 2H), 8.08(d, J=8.4Hz, 2H), 8.25(d, J=9.3Hz, 1H) |

TABLE 12

| Example No. | R² | R²' | R⁶ | * | 1H-NMR (DMSO-d₆) |
|---|---|---|---|---|---|
| A-100 | s-Bu | H | 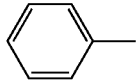 | S | 0.75-0.90(m, 6H), 1.12(m, 1H), 1.38(m, 1H), 1.70(m, 1H), 3.62(m, 1H), 7.51-7.62(m, 3H), 7.81(s, 1H), 7.89-8.00(m, 4H), 8.10(d, J=8.4Hz, 2H), 8.25(d, J=8.4Hz, 1H), 12.63(br s, 1H) |
| A-101 | s-Bu | H | 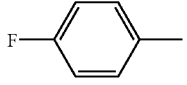 | S | 0.74-0.87(m, 6H), 1.12(m, 1H), 1.37(m, 1H), 1.71(m, 1H), 3.62(m, 1H), 7.38-7.48(m, 2H), 7.81(s, 1H), 7.95(d, J=8.7Hz, 2H), 7.96-8.04(m, 2H), 8.08(d, J=8.7Hz, 2H), 8.25(m, 1H), 12.65(br s, 1H) |
| A-102 | s-Bu | H | 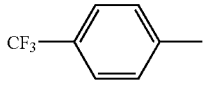 | S | 0.78(t, J=7.8Hz, 3H), 0.82(d, J=6.9Hz, 3H), 1.12(m, 1H), 1.37(m, 1H), 1.71(m, 1H), 3.62(m, 1H), 7.90-8.01(m, 5H), 8.11(d, J=8.7Hz, 2H), 8.17(d, J=8.1Hz, 2H), 8.26(m, 1H), 12.66(br s, 1H) |
| A-103 | s-Bu | H | 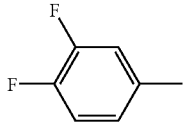 | S | 0.79(t, J=7.5Hz, 3H), 0.83(d, J=6.9Hz, 3H), 1.12(m, 1H), 1.39(m, 1H), 1.70(m, 1H), 3.60(m, 1H), 7.80-7.85(m, 2H), 7.88(s, 1H), 7.93-8.02(m, 3H), 8.07(d, J=8.7Hz, 2H), 8.27(d, J=9.6Hz, 1H), 12.65(br s, 1H) |
| A-104 | s-Bu | H | 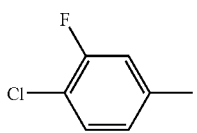 | S | 0.78(t, J=7.5Hz, 3H), 0.82(d, J=6.9Hz, 3H), 1.12(m, 1H), 1.37(m, 1H), 1.70(m, 1H), 3.62(m, 1H), 7.80-7.85(m, 2H), 7.88(s, 1H), 7.93-8.02(m, 3H), 8.07(d, J=8.7Hz, 2H), 8.27(d, J=9.6Hz, 1H), 12.65(br s, 1H) |

TABLE 12-continued

| Example No. | R² | R²' | R⁶ | * | 1H-NMR (DMSO-d₆) |
|---|---|---|---|---|---|
| A-105 | —CH₂CH₂—SMe | H | phenyl | R | 1.71-1.89(m, 2H), 1.94(s, 3H), 2.29-2.45(m, 2H), 3.91(brs, 1H), 7.55-7.61(m, 3H), 7.81(s, 1H), 7.92-7.96(m, 4H), 8.10(d, J=8.1Hz, 2H), 8.37(brs, 1H), 12.79(brs, 1H) |
| A-106 | —CH₂CH₂—SMe | H | 4-Me-phenyl | R | 1.68-2.00(m, 2H), 1.94(s, 3H), 2.26-2.50(m, 2H), 2.39(s, 3H), 3.93(m, 1H), 7.38(d, J=8.4Hz, 2H), 7.78(s, 1H), 7.83(d, J=8.1Hz, 2H), 7.95(d, J=8.4Hz, 2H), 8.10(d, J=8.4Hz, 2H), 8.40(d, J=8.4Hz, 1H), 12.8(br s, 1H) |
| A-107 | —CH₂CH₂—SMe | H | 4-i-Pr-phenyl | R | 1.25(d, J=6.9Hz, 6H), 1.80(m, 1H), 1.94(s, 3H), 2.38(m, 1H), 2.97(quint, J=6.9Hz, 1H), 3.92(d, J=3.9Hz, 1H), 7.44(d, J=8.4Hz, 2H), 7.78(s, 1H), 7.86(d, J=8.7Hz, 2H), 7.95(d, J=8.4Hz, 2H), 8.10(d, J=8.7Hz, 2H), 8.23(d, J=7.8Hz, 1H), 12.67(brs, 1H) |
| A-108 | —CH₂CH₂—SMe | H | 4-CF₃O-phenyl | R | 1.70-1.91(m, 2H), 1.94(s, 3H), 2.28-2.47(m, 2H), 3.93(m, 1H), 7.59(d, J=7.8Hz, 2H), 7.87(s, 1H), 7.96(d, J=8.4Hz, 2H), 8.09(t, J=9.0Hz, 4H), 8.41(br s, 1H), 12.8(br s, 1H) |
| A-109 | 3-(1H-indolyl)methyl | H | phenyl | R | 2.88(dd, J=8, 14.1Hz, 1H), 3.09(dd, J=6, 14.1Hz, 1H), 3.95(brs, 1H), 6.87-6.98(m, 2H), 7.08(d, J=2.4Hz, 1H), 7.19(d, J=7.2Hz, 1H), 7.33(d, J=7.5Hz, 1H), 7.55-7.62(m, 3H), 7.65(d, J=8.4Hz, 2H), 7.72(s, 1H), 7.83(d, J=8.4Hz, 2H), 7.79-7.97(m, 2H), 8.39(brs, 1H), 10.76(s, 1H), 12.72(brs, 1H) |

TABLE 13

| Example No. | R² | R²' | R⁶ | * | 1H-NMR (DMSO-d₆) |
|---|---|---|---|---|---|
| A-110 | 3-(1H-indolyl)methyl | H | 4-Me-phenyl | R | 2.40(s, 3H), 2.88(dd, J=8.4, 14.4Hz, 1H), 3.09(dd, J=5.7, 14.4Hz, 1H), 3.94(brs, 1H), 6.87-6.98(m, 2H), 7.07(d, J=2.1Hz, 1H), 7.19(d, J=7.5Hz, 1H), 7.33(d, J=7.5Hz, 1H), 7.39(d, J=8.4Hz, 2H), 7.65(d, J=8.4Hz, 2H), 7.68(s, 1H), 7.83(t-like, J=8Hz, 4H), 8.38(brs, 1H), 12.75(brs, 1H) |
| A-111 | 3-(1H-indolyl)methyl | H | 4-i-Pr-phenyl | R | 1.25(d, J=6.9Hz, 6H), 2.84-3.12(m, 3H), 3.95(d, J=5.1Hz, 1H), 6.87-6.98(m, 2H), 7.08(d, J=2.4Hz, 1H), 7.18(d, J=7.2Hz, 1H), 7.32(d, J=7.2Hz, 1H), 7.45(d, J=.4Hz, 2H), 7.65(d, J=8.7Hz, 2H), 7.69(s, 1H), 7.82(d, J=8.4Hz, 2H), 7.87(d, J=8.7Hz, 2H), 8.44(d, J=8.1Hz, 1H), 10.77(s, 1H) 12.73(brs, 1H) |
| A-112 | 3-(1H-indolyl)methyl | H | 4-MeO-phenyl | R | 2.09(s, 3H), 2.87(m, 1H), 3.08(m, 1H), 3.95(m, 1H), 6.87-6.95(m, 2H), 7.07-7.20(4H, m), 7.32(d, J=7.8Hz, 1H), 7.62-7.67(m, 3H), 7.81(d, J=8.7Hz, 2H), 7.89(d, J=8.7Hz, 2H), 8.44(d, J=8.1Hz, 1H), 10.77(s, 1H) 12.74(br s, 1H) |
| A-113 | —CH₂CO₂H | H | 4-Me-phenyl | R | 2.40-2.68(m, 2H), 4.14(br s, 1H), 7.38(d, J=8.4Hz, 2H), 7.77(s, 1H), 7.83(d, J=7.8Hz, 2H) 7.96(d, J=8.4Hz, 2H), 8.09(d, J=8.4Hz, 2H), 8.42(br s, 1H), 12.66(br s, 1H) |
| A-114 | —CH₂CH₂—CO₂H | H | 4-F-phenyl | R | 1.69(m, 1H), 1.88(m, 1H), 2.24(t, J=7.5Hz, 2H), 3.85(br s, 1H), 7.43(t, J=9.0Hz, 2H), 7.81(s, 1H), 7.93-8.02(m, 4H), 8.37(br s, 1H), 12.44(br s, 2H) |

TABLE 13-continued

| Example No. | R² | R²' | R⁶ | * | 1H-NMR (DMSO-d₆) |
|---|---|---|---|---|---|
| A-115 | —CH₂CH₂—CO₂H | H | 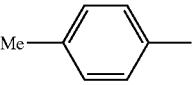 Me— | R | 1.69(m, 1H), 1.88(m, 1H), 2.24(t, J=7.5Hz, 2H), 2.39(s, 3H), 3.84(br s, 1H), 7.38(d, J=8.4Hz, 2H), 7.77(s, 1H), 7.83(d, J=8.1Hz, 2H), 7.93(d, J=8.1Hz, 2H), 8.09(d, J=8.7Hz, 2H), 8.37(m, 1H), 12.4(brs, 2H) |
| A-116 | Ph | H | 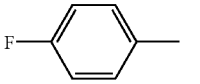 F— | R | 5.97(d, J=9.3Hz, 1H), 7.23-7.32(5H), 7.42(t, J=9.0Hz, 2H), 7.78(s, 1H), 7.89(d, J=7.8Hz, 2H), 7.95-8.03(m, 4H), 8.94(d, J=9.0Hz, 1H), 13.01(br s, 1H) |
| A-117 | i-Pr | H | 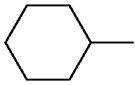 | R | 0.80(d, J=6.9Hz, 3H), 0.83(d, J=6.9Hz, 3H), 1.20-1.55(m, 5H), 1.65-1.85(m, 3H), 1.85-2.00(m, 3H), 2.77(m, 1H), 3.55(m, 1H), 7.18(s, 1H), 7.89(d, J=8.4Hz, 2H), 8.00(d, J=8.7Hz, 2H), 8.19(d, J=9.0Hz, 1H), 12.59(br s, 1H) |

TABLE 14

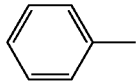

| Example No. | R² | R⁶ | * | 1H-NMR (DMSO-d₆) |
|---|---|---|---|---|
| B-1 | i-Pr | 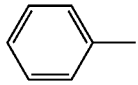 | R | 0.83(d, J=6.6Hz, 3H), 0.88(d, J=6.6Hz, 3H), 2.02(m, 1H), 3.65(d, J=6.0Hz, 1H), 7.55-7.57(m, 3H), 7.66(d, J=4.2Hz, 1H), 7.68(s, 1H), 7.73(d, J=4.2Hz, 1H), 7.90-7.94(m, 2H), 8.55(brs, 1H), 12.84(brs, 1H) |
| B-2 | i-Pr | 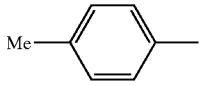 | S | 0.83(d, J=6.6Hz, 3H), 0.88(d, J=6.6Hz, 3H), 2.02(m, 1H), 3.66(d, J=5.7Hz, 1H), 7.55-7.61(m, 3H), 7.66(d, J=3.9Hz, 1H), 7.68(s, 1H), 7.73(d, J=3.9Hz, 1H), 7.89-7.94(m, 2H), 8.57(brs, 1H), 12.84(brs, 1H) |
| B-3 | i-Pr | Me— 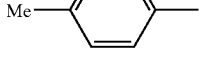 | R | 0.82-0.89(m, 6H), 2.02(m, 1H), 3.67(br s, 1H), 7.37-7.66(d, J=8.4Hz, 1H), 7.63-7.66(m, 3H), 7.72(s, 1H), 7.81(d, J=8.1Hz, 1H) |
| B-4 | i-Pr | Me— 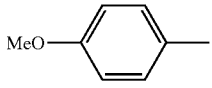 | S | 0.83(d, J=6.6Hz, 3H), 0.88(d, J=6.9Hz, 3H), 2.02(m, 1H), 2.38(s, 3H), 3.65(d, J=5.7Hz, 1H), 7.37(d, J=8.4Hz, 2H), 7.64(s, 1H), 7.65(d, J=3.9Hz, 1H), 7.71(d, J=3.9Hz, 1H), 7.81(d, J=8.4Hz, 2H), 8.58(brs, 1H), 12.75(brs, 1H) |
| B-5 | i-Pr | MeO— 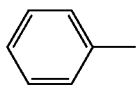 | S | 0.83(d, J=6.6Hz, 3H), 0.88(d, J=6.6Hz, 3H), 2.03(m, 1H), 3.65(d, J=5.7Hz, 1H), 3.84(s, 3H), 7.11(d, J=8.7Hz, 2H), 7.61(s, 1H), 7.65(d, J=3.9Hz, 1H), 7.70(d, J=3.9Hz, 1H), 7.85(d, J=9.0Hz, 2H), 8.57(br s, 1H) |
| B-6 | i-Bu | 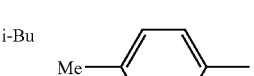 | R | 0.79(d, J=6.6Hz, 3H), 0.86(d, J=6.6Hz, 3H), 1.43-1.48(m, 2H), 1.65(m, 1H), 3.79(t-like, J=7Hz, 1H), 7.54-7.58(m, 3H), 7.66(d, J=3.9Hz, 1H), 7.68(s, 1H), 7.73(d, J=3.9Hz, 1H), 7.90-7.93(m, 2H), 8.68(brs, 1H), 12.81(brs, 1H) |
| B-7 | i-Bu | Me— | R | 0.79(d, J=6.3Hz, 3H), 0.86(d, J=6.6Hz, 3H), 1.40-1.55(m, 2H), 1.64(m, 1H), 2.38(s, 3H), 3.83(m, 1H), 7.37(d, J=8.1Hz, 2H), 7.63-7.67(m, 2H), 7.71(d, J=3.9Hz 1H), 7.81(d, J=8.1Hz, 2H), 8.68(brs, 1H), 12.81(brs, 1H) |

TABLE 14-continued

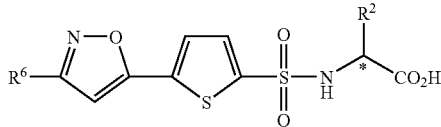

| Example No. | R² | R⁶ | * | 1H-NMR (DMSO-d₆) |
|---|---|---|---|---|
| B-8 | s-Bu | 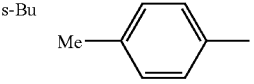 Me— | S | 0.77-0.87(m, 6H), 1.15(m, 1H), 1.38(m, 1H), 2.38(s, 3H), 3.70(m, 1H), 7.37(d, J=8.1Hz, 2H), 7.63(s, 1H), 7.65(d, J=3.9Hz, 1H), 7.71(d, J=3.9Hz, 1H), 7.81(d, J=8.4Hz, 2H), 8.60(br s, 1H), 12.77(br s, 1H) |
| B-9 | s-Bu | 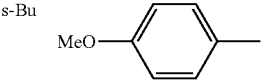 MeO— | S | 0.76-0.88(m, 6H), 1.15(m, 1H), 1.38(m, 1H), 1.74(br s, 1H), 3.71(br s, 1H), 3.84(s, 3H), 7.01(d, J=9.0Hz, 2H), 7.60(s, 1H), 7.65(d, J=3.9Hz, 1H), 7.70(d, J=3.9Hz, 1H), 7.80(d, J=8.7Hz, 2H), 8.60(br s, 1H) |

TABLE 15

| Example No. | R² | R⁶ | * | 1H-NMR (DMSO-d₆) |
|---|---|---|---|---|
| B-10 | s-Bu | 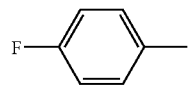 F— | S | 0.76-0.88(m, 6H), 1.15(m, 1H), 1.37(m, 1H), 3.70(br s, 1H), 7.42(t, J=9.0Hz, 2H), 7.67(s, 1H), 7.72(d, J=4.2Hz, 1H), 7.98(dd, J=5.4, 8.7Hz, 2H), 8.62(d, J=8.4Hz, 1H), 12.8(br s, 1H) |
| B-11 | —CH₂CH₂SMe | 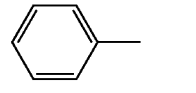 | R | 1.72-2.00(m, 2H), 1.98(s, 3H), 2.34-2.56(m, 2H), 4.01(m, 1H), 7.54-7.60(m, 3H), 7.68(d, J=5.4Hz, 1H), 7.74(d, J=4.4Hz, 1H), 7.86-7.96(m, 2H), 8.76(d, J=9.0Hz, 1H), 12.92(br s, 1H) |
| B-12 | —CH₂CH₂SMe | 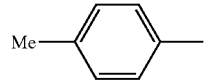 Me— | R | 1.73-1.96(m, 2H), 1.97(s, 3H), 2.35-2.53(m, 2H), 2.38(s, 3H), 4.00(m, 1H), 7.37(d, J=8.1Hz, 2H), 7.64-7.68(m, 2H), 7.72(s, 1H), 7.81(d, J=8.1Hz, 1H), 8.76(d, J=9.0Hz, 1H), 12.9(br s, 1H) |
| B-13 | 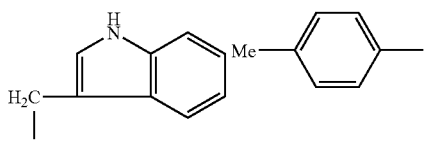 | 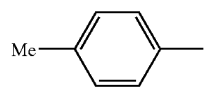 Me— | R | 2.39(s, 3H), 2.91(dd, J=8.4, 14.4Hz, 1H), 3.13(dd, J=5.4, 14.4Hz, 1H), 4.00(brs, 1H), 6.88-6.97(m, 2H), 7.10(d, J=1.8Hz, 1H), 7.17(d, J=7.2Hz, 1H), 7.37-7.39(m, 4H), 7.50(s, 1H), 7.82(d, J=8.4Hz, 2H), 8.71(brs, 1H), 10.80(s, 1H) 12.86(brs, 1H) |
| B-14 | —CH₂OH | 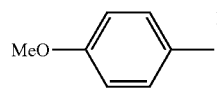 Me— | R | 2.37(d, J=5.4Hz, 2H), 3.69(1H, m), 6.88(d, J=9.0Hz, 2H), 7.38(s, 1H), 7.45(d, J=4.2Hz, 1H), 7.48(d, J=3.9Hz, 1H), 7.63(d, J=8.7Hz, 1H), 8.38(d, J=8.7Hz, 1H) |
| B-15 | 4-OH—Bn | 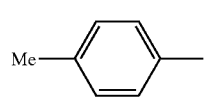 MeO— | R | 2.66(dd, J=9, 15Hz, 1H), 2.89(dd, J=5.4, 12Hz, 1H), 3.84(s, 3H), 3.91(m, 1H), 6.59(d, J=8.1Hz, 2H), 6.96(d, J=8.4Hz, 2H), 7.11(d, J=9Hz, 2H), 7.40(d, J=3.9Hz, 1H), 7.52(s, 1H), 7.57(d, J=3.9Hz, 1H), 7.86(d, J=9Hz, 2H), 8.77(d, J=9Hz, 1H), 9.19(s, 1H), 12.84(br s, 1H) |
| B-16 | 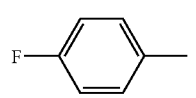 | Me— | R | 2.39(S, 1H), 4.98(d, J=9.3Hz, 1H), 7.20-7.31(5H), 7.37(d, J=8.1Hz, 2H), 7.74(s, 1H), 7.82(d, J=8.1Hz, 2H), 7.88(d, J=8.7Hz, 2H), 7.98(d, J=8.7Hz, 2H), 8.93(d, J=9.3Hz, 1H) |
| B-17 | i-Pr | F— | S | 0.83(d, J=6.9Hz, 3H), 0.88(d, J=6.9Hz, 3H), 2.04(m, 1H), 3.65(d, J=5.4Hz, 1H), 7.42(t, J=8.9Hz, 2H), 7.66(d, J=3.9Hz, 1H), 7.67(s, 1H), 7.71(d, J=3.9Hz, 1H), 7.98(m, 2H) |

TABLE 15-continued

| Example No. | R² | R⁶ | * | 1H-NMR (DMSO-d₆) |
|---|---|---|---|---|
| B-18 | i-Pr | 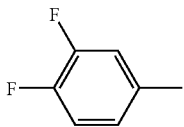 | S | 0.81(d, J=6.9Hz, 3H), 0.86(d, J=6.9Hz, 3H), 2.02(m, 1H), 3.64(d, J=6.0Hz, 1H), 7.60-7.69(m, 4H), 7.78(brm, 1H), 7.98(m, 1H), 8.55(brs, 1H) |
| B-19 | i-Pr | 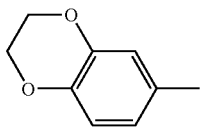 | S | 0.83(d, J=6.9Hz, 3H), 0.87(d, J=6.6Hz, 3H), 2.01(m, 1H), 3.65(d, J=5.4Hz, 1H), 4.31(s, 4H), 7.02(d, J=9.0Hz, 1H), 7.39(m, 2H), 7.59(s, 1H), 7.64(d, J=4.2Hz, 1H), 7.68(d, J=3.9Hz, 1H), 8.57(brs, 1H) |

TABLE 16

| Example No. | R² | R⁶ | * | 1H-NMR (DMSO-d₆) |
|---|---|---|---|---|
| B-20 | i-Pr | 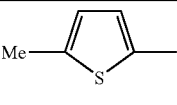 | S | 0.82(d, J=6.9Hz, 3H), 0.86(d, J=6.6Hz, 3H), 2.01(m, 1H), 3.64(d, J=5.4Hz, 1H), 6.94(dd, J=1.1Hz, 3.6Hz, 1H), 7.53(d, J=4.2Hz, 1H), 7.54(s, 1H), 7.63(d, J=3.9Hz, 1H), 7.69(d, J=3.9Hz, 1H), 8.56(brs, 1H) |

Example 2

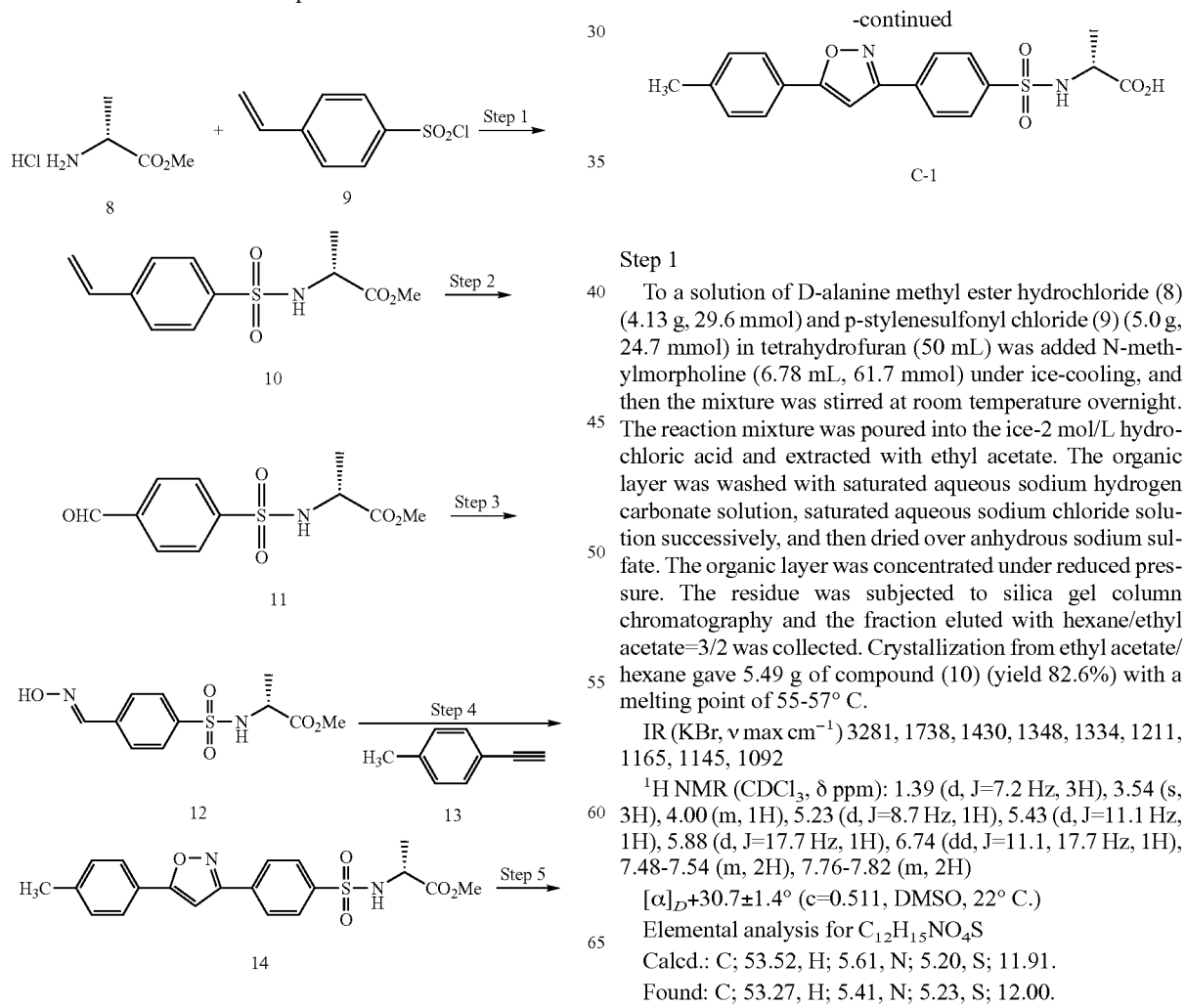

Step 1

To a solution of D-alanine methyl ester hydrochloride (8) (4.13 g, 29.6 mmol) and p-stylenesulfonyl chloride (9) (5.0 g, 24.7 mmol) in tetrahydrofuran (50 mL) was added N-methylmorpholine (6.78 mL, 61.7 mmol) under ice-cooling, and then the mixture was stirred at room temperature overnight. The reaction mixture was poured into the ice-2 mol/L hydrochloric acid and extracted with ethyl acetate. The organic layer was washed with saturated aqueous sodium hydrogen carbonate solution, saturated aqueous sodium chloride solution successively, and then dried over anhydrous sodium sulfate. The organic layer was concentrated under reduced pressure. The residue was subjected to silica gel column chromatography and the fraction eluted with hexane/ethyl acetate=3/2 was collected. Crystallization from ethyl acetate/hexane gave 5.49 g of compound (10) (yield 82.6%) with a melting point of 55-57° C.

IR (KBr, ν max cm⁻¹) 3281, 1738, 1430, 1348, 1334, 1211, 1165, 1145, 1092

$^{1}$H NMR (CDCl₃, δ ppm): 1.39 (d, J=7.2 Hz, 3H), 3.54 (s, 3H), 4.00 (m, 1H), 5.23 (d, J=8.7 Hz, 1H), 5.43 (d, J=11.1 Hz, 1H), 5.88 (d, J=17.7 Hz, 1H), 6.74 (dd, J=11.1, 17.7 Hz, 1H), 7.48-7.54 (m, 2H), 7.76-7.82 (m, 2H)

$[\alpha]_D$ +30.7±1.4° (c=0.511, DMSO, 22° C.)

Elemental analysis for $C_{12}H_{15}NO_4S$

Calcd.: C; 53.52, H; 5.61, N; 5.20, S; 11.91.

Found: C; 53.27, H; 5.41, N; 5.23, S; 12.00.

Step 2

A solution of compound (10) (5.43 g, 20.2 mmol) in methylene chloride (80 mL) was cooled to −78° C. and stirred for 50 min with bubbling an ozone gas. To the mixture was added methyl sulfide (7.4 mL, 100.8 mmol) and stirred at the same temperature for 30 min, moreover stirred at room temperature for 1 h. The reaction mixture was concentrated under reduced pressure, and the obtained compound (11) was used for next step without any purification.

$^1$H NMR (CDCl$_3$, δ ppm): 1.42 (d, J=7.2 Hz, 3H), 3.56 (s, 3H), 4.07 (m, 1H), 5.42 (d, J=8.4 Hz, 1H), 8.02 (s, 4H), 10.10 (s, 1H)

Step 3

To a solution of the above mentioned unpurified compound (11) and hydroxylamine hydrochloride (1.68 g, 24.2 mmol) in a mixed solvent of tetrahydrofuran (50 mL) and water (50 mL) was added sodium hydrogen carbonate (2.54 g, 30.2 mmol) and the mixture was stirred at room temperature overnight. The reaction mixture was poured into ice water, and extracted with ethyl acetate. The organic layer was washed with saturated aqueous sodium chloride solution. The organic layer was dried over anhydrous sodium sulfate, and then concentrated under reduced pressure. The residue was subjected to silica gel column chromatography and the fraction eluted with hexane/ethyl acetate=1/1 to 2/3 was collected. Crystallization from ethyl acetate/hexane gave 3.04 g of compound (12) (yield through 2 steps 52.7%) with a melting point of 98-100° C.

IR (KBr, ν max cm$^{-1}$) 3518, 3384, 3300, 1754, 1738, 1722, 1444, 1347, 1273, 1217, 1166, 1144, 1092

$^1$H NMR (DMSO-d$_6$, δ ppm): 1.17 (d, J=7.2 Hz, 3H), 3.42 (s, 3H), 3.90 (m, 1H), 7.77 (s, 4H), 8.23 (s, 1H), 8.38 (br s, 1H), 11.62 (br s, 1H)

[α]$_D$+26.7±1.3° (c=0.514, DMSO, 21° C.)

Elemental analysis for C$_{12}$H$_{14}$N$_2$O$_5$S

Calcd.: C; 46.15, H; 4.93, N; 9.78, S; 11.20.

Found: C; 46.13, H; 4.74, N; 9.69, S; 10.99.

Step 4

A solution of compound (12) (501 mg, 1.75 mmol) and N-chlorosuccinimide (257 mg, 1.93 mmol) in dimethylformamide (3 mL) was stirred at 60° C. for 30 min. After the reaction mixture was cooled to 0° C., to the mixture was added the solution of 4-ethynyltoluene (13) (305 mg, 2.63 mmol) and N-methylmorpholine (0.29 mL, 2.63 mmol) in dimethylformamide (2 mL), and the mixture was stirred at the same temperature for 10 min, moreover stirred at room temperature overnight. The reaction mixture was poured into ice-2 mol/L hydrochloric acid, and extracted with ethyl acetate. The organic layer was washed with saturated aqueous sodium hydrogen carbonate solution and saturated aqueous sodium chloride solution successively. The organic layer was dried over anhydrous sodium sulfate, and then concentrated under reduced pressure. The residue was subjected to silica gel column chromatography and the fraction eluted with chloroform/ethyl acetate=6/1 was collected. Crystallization from acetone/hexane gave 467 mg of compound (14) (yield 66.6%) with a melting point of 187-189° C.

IR (KBr, ν max cm$^{-1}$) 3285, 1740, 1721, 1450, 1434, 1340, 1285, 1170, 1137, 1097

$^1$H NMR (CDCl$_3$, δ ppm): 1.42 (d, J=7.5 Hz, 3H), 2.43 (s, 3H), 3.56 (s, 3H), 4.05 (m, 1H), 5.30 (d, J=8.4 Hz, 1H), 6.82 (s, 1H), 7.31 (d, J=8.1 Hz, 2H), 7.71-7.76 (m, 2H), 7.93-8.04 (m, 4H)

[α]$_D$+19.0±1.2° (c=0.512, DMSO, 21° C.)

Elemental analysis for C$_{20}$H$_{20}$N$_2$O$_5$S

Calcd.: C; 59.99, H; 5.03, N; 7.00, S; 8.01.

Found: C; 59.90, H; 4.95, N; 6.99, S; 7.71.

Step 5

To a solution of compound (14) (410 mg, 1.02 mmol) in dimethylsulfoxide (9.2 mL) was added 1 mol/L aqueous sodium hydroxide solution (3.06 mL) at room temperature, and the mixture was stirred overnight. The precipitated sodium salt was filtered, washed with ethyl acetate. The sodium salt was added into ice-2 mol/L hydrochloric acid, and extracted with ethyl acetate. The organic layer was washed with saturated aqueous sodium chloride solution. The organic layer was dried over anhydrous sodium sulfate, and then concentrated under reduced pressure. Crystallization of the residue from acetone/hexane gave 377 mg of the compound (C-1) (yield 95.6%) with a melting point of 218-221° C.

IR (KBr, ν max cm$^{-1}$) 3391, 1749, 1450, 1434, 1328, 1168, 1112, 1093

$^1$H NMR (DMSO-d$_6$, δ ppm): 1.19 (d, J=7.2 Hz, 3H), 2.39 (s, 3H), 3.85 (m, 1H), 7.40 (d, J=7.8 Hz, 2H), 7.65 (s, 1H), 7.82 (d, J=7.8 Hz, 2H), 7.95 (d, J=8.4 Hz, 2H), 8.10 (d, J=8.4 Hz, 2H), 8.32 (d, J=8.7 Hz, 1H), 12.70 (br s, 1H)

[α]$_D$+3.0±0.9° (c=0.502, DMSO, 22° C.)

Elemental analysis for C$_{19}$H$_{18}$N$_2$O$_5$S

Calcd.: C; 59.06, H; 4.70, N; 7.25, S; 8.30.

Found: C; 58.85, H; 4.82, N; 7.17, S; 8.34.

According to Example 2 and above mentioned Method B, the following compound (C-1) to compound (C-124) were synthesized. Their structures and the results of their physical data were shown in Table 17 to 35. The mark * shows an asymmetric carbon.

TABLE 17

[Structure: R$^6$—[isoxazole O—N]—[phenyl]—S(=O)$_2$—NH—*CH(R$^2$)—CO$_2$H]

| Example No. | R$^2$ | R$^6$ | * | 1H-NMR (DMSO-d$_6$) |
|---|---|---|---|---|
| C-1 | Me | 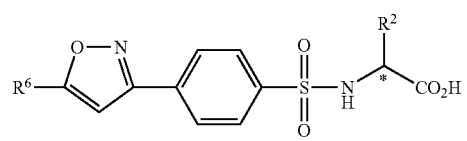 | R | 1.19(d, J=7.2Hz, 3H), 2.39(s, 3H), 3.85(m, 1H), 7.11-7.17(m, 2H), 7.57(s, 1H), 7.84-7.90(m, 2H), 7.90-7.96(m, 2H), 8.05-8.11(m, 2H), 8.19(d, J=8.7Hz, 1H), 12.65(br s, 1H) |

TABLE 17-continued

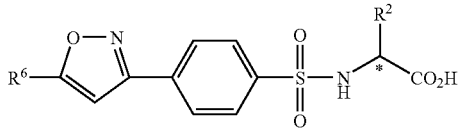

| Example No. | R² | R⁶ | * | 1H-NMR (DMSO-d₆) |
|---|---|---|---|---|
| C-2 | Me | 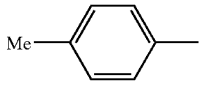 | S | 1.19(d, J=7.2Hz, 3H), 2.39(s, 3H), 3.85(m, 1H), 7.40(d, J=7.8Hz, 2H), 7.65(s, 1H), 7.82(d, J=8.1H, 2H), 7.95(d, J=8.4Hz, 2H), 8.10(d, J=8.1Hz, 2H), 8.32(d, J=7.5Hz, 1H), 12.68(br s, 1H) |
| C-3 | Me | 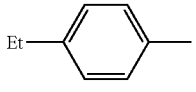 | S | 1.19(d, J=6.9Hz, 3H), 1.23(t, J=7.5Hz, 3H), 2.69(q, J=7.5Hz, 2H), 3.85(m, 1H), 7.43(d, J=8.1Hz, 2H), 7.66(s, 1H), 7.85(d, J=8.1Hz, 2H), 7.95(d, J=8.1Hz, 2H), 8.10(d, J=8.4Hz, 2H), 8.32(d, J=8.4Hz, 1H), 12.65(br s, 1H) |
| C-4 | Me | 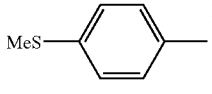 | R | 1.19(d, J=7.2Hz, 3H), 2.56(s, 3H), 3.85(m, 1H), 7.42-7.48(m, 2H), 7.68(s, 1H), 7.82-7.88(m, 2H), 7.92-7.98(m, 2H), 8.07-8.13(m, 2H), 8.33(d, J=7.8Hz, 1H), 12.70(br s, 1H) |
| C-5 | Me | 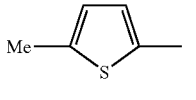 | S | 1.19(d, J=7.2Hz, 3H), 2.55(s, 3H), 3.84(m, 1H), 6.99(dd, J=0.6, 4.2Hz, 1H), 7.44(s, 1H), 7.55(d, J=3.9Hz, 1H), 7.93(d, J=8.7Hz, 2H), 8.09(d, J=8.7Hz, 2H), 8.32(d, J=9.0Hz, 1H), 12.70(br s, 1H) |
| C-6 | i-Pr | 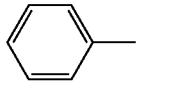 | R | 0.82(d, J=6.6Hz, 3H), 0.85(d, J=6.9Hz, 3H), 1.97(m, 1H), 3.58(m, 1H), 7.52-7.64(m, 3H), 7.73(s, 1H), 7.90-7.98(m, 4H), 8.10(d, J=8.4Hz, 2H), 8.20(d, J=8.7Hz, 1H), 12.64(br s, 1H) |
| C-7 | i-Pr | 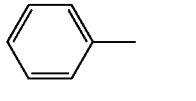 | S | 0.81(d, J=6.9Hz, 3H), 0.85(d, J=6.9Hz, 3H), 1.97(m, 1H), 3.58(m, 1H), 7.52-7.63(m, 3H), 7.73(s, 1H), 7.91-7.97(m, 4H), 8.10(d, J=8.4Hz, 2H), 8.20(d, J=8.7Hz, 1H), 12.66(br s, 1H) |
| C-8 | i-Pr | 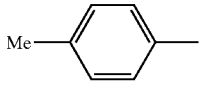 | R | 0.81(d, J=6.6Hz, 3H), 0.85(d, J=6.9Hz, 3H), 1.97(m, 1H), 2.39(s, 3H), 3.58(m, 1H), 7.40(d, J=8.1Hz, 2H), 7.65(s, 1H), 7.82(d, J=8.1Hz, 2H), 7.93(d, J=8.7Hz, 2H), 8.09(d, J=8.7Hz, 2H), 8.19(d, J=8.7Hz, 1H), 12.57(br s, 1H) |

TABLE 18

| Example No. | R² | R⁶ | * | 1H-NMR (DMSO-d₆) |
|---|---|---|---|---|
| C-9 | i-Pr | 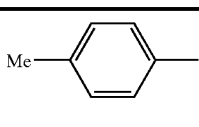 | S | 0.81(d, J=6.9Hz, 3H), 0.85(d, J=6.6Hz, 3H), 1.97(m, 1H), 2.39(s, 3H), 3.58(m, 1H), 7.40(d, J=8.1Hz, 2H), 7.65(s, 1H), 7.82(d, J=8.1Hz, 2H), 7.93(d, J=8.4Hz, 2H), 8.09(d, J=8.4Hz, 2H), 8.19(d, J=8.4Hz, 1H), 12.64(br s, 1H) |
| C-10 | i-Pr | 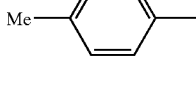 | R | 0.81(d, J=6.9Hz, 3H), 0.85(d, J=6.9Hz, 3H), 1.97(m, 1H), 2.56(s, 3H), 3.58(m, 1H), 7.45(d, J=8.4Hz, 2H), 7.67(s, 1H), 7.85(d, J=8.4Hz, 2H), 7.93(d, J=8.4Hz, 2H), 8.08(d, J=8.4Hz, 2H), 8.19(d, J=8.1Hz, 1H), 12.62(br s, 1H) |
| C-11 | i-Pr | 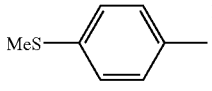 | S | 0.81(d, J=6.9Hz, 3H), 0.85(d, J=6.6Hz, 3H), 1.97(m, 1H), 2.56(s, 3H), 3.58(m, 1H), 7.42-7.48(m, 2H), 7.67(s, 1H), 7.83-7.88(m, 2H), 7.91-7.96(m, 2H), 8.06-8.11(m, 2H), 8.18(d, J=9.0Hz, 1H), 12.63(br s, 1H) |

TABLE 18-continued

| Example No. | R² | R⁶ | * | 1H-NMR (DMSO-d₆) |
|---|---|---|---|---|
| C-12 | i-Pr | Et—C₆H₄— | R | 0.82(d, J=7.2Hz, 3H), 0.85(d, J=6.6Hz, 3H), 1.23(t, J=7.2Hz, 3H), 1.97(m, 1H), 2.69(q, J=7.2Hz, 2H), 3.59(m, 1H), 7.43(d, J=8.1Hz, 2H), 7.66(s, 1H), 7.85(d, J=8.1Hz, 2H), 7.94(d, J=8.4Hz, 2H), 8.09(d, J=8.4Hz, 2H), 8.19(d, J=9.0Hz, 1H), 12.63(br s, 1H) |
| C-13 | i-Pr | Et—C₆H₄— | S | 0.81(d, J=6.9Hz, 3H), 0.85(d, J=6.6Hz, 3H), 1.23(t, J=7.5Hz, 3H), 1.97(m, 1H), 2.69(q, J=7.5Hz, 2H), 3.58(dd, J=6.0, 8.4Hz, 1H), 7.43(d, J=8.4Hz, 2H), 7.66(s, 1H), 7.85(d, J=8.4Hz, 2H), 7.94(d, J=8.4Hz, 2H), 8.09(d, J=8.4Hz, 2H), 8.20(d, J=8.4Hz, 1H), 12.65(br s, 1H) |
| C-14 | i-Pr | n-Pr—C₆H₄— | R | 0.81(d, J=6.9Hz, 3H), 0.85(d, J=6.6Hz, 3H), 0.92(t, J=7.5Hz, 3H), 1.56-1.72(m, 2H), 1.97(m, 1H), 2.64(t, J=7.2Hz, 1H), 3.58(m, 1H), 7.41(d, J=8.1Hz, 2H), 7.66(s, 1H), 7.84(d, J=8.1Hz, 2H), 7.94(d, J=8.4Hz, 2H), 8.09(d, J=8.4Hz, 2H), 8.20(d, J=9.3Hz, 1H), 12.62(br s, 1H) |

TABLE 19

| Example No. | R² | R⁶ | * | 1H-NMR (DMSO-d₆) |
|---|---|---|---|---|
| C-15 | i-Pr | i-Pr—C₆H₄— | R | 0.81(d, J=6.6Hz, 3H), 0.85(d, J=6.6Hz, 3H), 1.25(d, J=7.2Hz, 6H), 1.97(m, 1H), 2.98(m, 1H), 3.58(d, J=6.3, 9.0Hz, 1H), 7.47(d, J=8.1Hz, 2H), 7.67(s, 1H), 7.85(d, J=8.1Hz, 2H), 7.94(d, J=8.4Hz, 2H), 8.10(d, J=8.4Hz, 2H), 8.20(d, J=9.0Hz, 1H), 12.65(br s, 1H) |
| C-16 | i-Pr | i-Pr—C₆H₄— | S | 0.82(d, J=6.6Hz, 3H), 0.85(d, J=6.9Hz, 3H), 1.25(d, J=7.2Hz, 6H), 1.97(m, 1H), 2.98(m, 1H), 3.58(br t, J=6.9Hz, 1H), 7.47(d, J=8.1Hz, 2H), 7.66(s, 1H), 7.86(d, J=8.1Hz, 2H), 7.94(d, J=8.4Hz, 2H), 8.10(d, J=8.4Hz, 2H), 8.20(d, J=8.7Hz, 1H), 12.65(br s, 1H) |
| C-17 | i-Pr | n-Bu—C₆H₄— | R | 0.81(d, J=6.9Hz, 3H), 0.85(d, J=6.9Hz, 3H), 0.91(t, J=7.5Hz, 3H), 1.36-1.40(m, 2H), 1.54-1.66(m, 2H), 1.97(m, 1H), 2.66(t, J=7.8Hz, 2H), 3.58(m, 1H), 7.41(d, J=8.1Hz, 2H), 7.66(s, 1H), 7.84(d, J=8.1Hz, 2H), 7.93(d, J=8.4Hz, 2H), 8.09(d, J=8.1Hz, 2H), 8.20(d, J=9.3Hz, 1H), 12.64(br s, 1H) |
| C-18 | i-Pr | MeO—C₆H₄— | R | 0.81(d, J=6.9Hz, 3H), 0.85(d, J=6.9Hz, 3H), 1.97(m, 1H), 3.58(dd, J=5.7, 8.7Hz, 1H), 3.85(s, 3H), 7.40(d, J=8.1Hz, 2H), 7.65(s, 1H), 7.82(d, J=8.1Hz, 2H), 7.93(d, J=8.7Hz, 2H), 8.09(d, J=8.7Hz, 2H), 8.19(d, J=8.7Hz, 1H), 12.57(br s, 1H) |
| C-19 | i-Pr | MeO—C₆H₄— | S | 0.82(d, J=6.6Hz, 3H), 0.85(d, J=6.9Hz, 3H), 1.97(m, 1H), 3.59(dd, J=5.7, 8.7Hz, 1H), 3.85(s, 3H), 7.11-7.18(m, 2H), 7.57(s, 1H), 7.84-7.91(m, 2H), 7.91-7.96(m, 2H), 8.05-8.11(m, 2H), 8.20(d, J=8.7Hz, 1H), 12.65(br s, 1H) |
| C-20 | i-Pr | Cl—C₆H₄— | R | 0.81(d, J=6.6Hz, 3H), 0.85(d, J=6.6Hz, 3H), 1.97(m, 1H), 3.59(dd, J=6.0, 9.6Hz, 1H), 7.68(d, J=8.4Hz, 2H), 7.78(s, 1H), 7.91-7.99(m, 4H), 8.09(d, J=8.4Hz, 2H), 8.20(d, J=9.6Hz, 1H), 12.64(br s, 1H) |

TABLE 20

| Example No. | R² | R⁶ | * | 1H-NMR (DMSO-d₆) |
|---|---|---|---|---|
| C-21 | i-Pr | 4-Cl-C₆H₄- | S | 0.81(d, J=6.9Hz, 3H), 0.85(d, J=6.9Hz, 3H), 1.97(m, 1H), 3.58(m, 1H), 7.68(d, J=8.7Hz, 2H), 7.78(s, 1H), 7.94(d, J=8.7Hz, 2H), 7.96(d, J=9.0Hz, 2H), 8.09(d, J=8.7Hz, 2H), 8.19(d, J=8.7Hz, 1H), 12.63(br s, 1H) |
| C-22 | i-Pr | 4-Br-C₆H₄- | R | 0.81(d, J=6.9Hz, 3H), 0.85(d, J=6.9Hz, 3H), 1.97(m, 1H), 3.59(m, 1H), 7.78(s, 1H), 7.78-7.84(m, 2H), 7.86-7.91(m, 2H), 7.92-7.97(m, 2H), 8.06-8.11(m, 2H), 8.19(d, J=8.7Hz, 1H), 12.67(br s, 1H) |
| C-23 | i-Pr | 4-Br-C₆H₄- | S | 0.81(d, J=6.9Hz, 3H), 0.85(d, J=6.9Hz, 3H), 1.97(m, 1H), 3.58(m, 1H), 7.79(s, 1H), 7.81(d, J=8.7Hz, 2H), 7.89(d, J=8.7Hz, 2H), 7.94(d, J=8.7Hz, 2H), 8.09(d, J=8.7Hz, 2H), 8.19(m, 1H), 12.57(br s, 1H) |
| C-24 | i-Pr | 4-F-C₆H₄- | S | 0.82(d, J=6.9Hz, 3H), 0.85(d, J=6.9Hz, 3H), 1.97(m, 1H), 3.59(m, 1H), 7.41-7.50(m, 2H), 7.71(s, 1H), 7.94(d, J=8.7Hz, 2H), 7.96-8.40(m, 2H), 8.09(d, J=8.7Hz, 2H), 8.20(d, J=8.1Hz, 1H), 12.60(br s, 1H) |
| C-25 | i-Pr | 4-F₃CO-C₆H₄- | R | 0.82(d, J=6.6Hz, 3H), 0.85(d, J=6.9Hz, 3H), 1.96(m, 1H), 3.59(m, 1H), 7.61(d, J=8.4Hz, 2H), 7.80(s, 1H), 7.92-7.98(m, 2H), 8.04-8.13(m, 4H), 8.21(d, J=9.0Hz, 1H), 12.65(br s, 1H) |
| C-26 | i-Pr | 4-F₃CO-C₆H₄- | S | 0.82(d, J=6.6Hz, 3H), 0.85(d, J=6.9Hz, 3H), 1.97(m, 1H), 3.59(t, J=6.9Hz, 1H), 7.61(d, J=8.1Hz, 2H), 7.80(s, 1H), 7.95(d, J=8.7Hz, 2H), 8.05-8.13(m, 4H), 8.20(d, J=9.0Hz, 1H), 12.65(br s, 1H) |
| C-27 | i-Pr | 4-F₃C-C₆H₄- | R | 0.82(d, J=6.9Hz, 3H), 0.85(d, J=6.6Hz, 3H), 1.97(m, 1H), 3.59(m, 1H), 7.92-8.02(m, 5H), 8.11(d, J=8.7Hz, 2H), 8.16(d, J=8.1Hz, 2H), 8.20(m, 1H), 12.63(br s, 1H) |
| C-28 | i-Pr | 4-F₃C-C₆H₄- | S | 0.81(d, J=6.9Hz, 3H), 0.85(d, J=6.9Hz, 3H), 1.97(m, 1H), 3.59(m, 1H), 7.91-8.02(m, 5H), 8.11(d, J=8.7Hz, 2H), 8.16(d, J=7.8Hz, 2H), 8.22(d, J=9.6Hz, 1H), 12.65(br s, 1H) |

TABLE 21

| Example No. | R² | R⁶ | * | 1H-NMR (DMSO-d₆) |
|---|---|---|---|---|
| C-29 | i-Pr | 5-Me-thiophen-2-yl | R | 0.81(d, J=6.6Hz, 3H), 0.85(d, J=6.6Hz, 3H), 1.96(m, 1H), 2.54(s, 3H), 3.57(m, 1H), 6.99(dd, J=0.9, 3.6Hz, 1H), 7.44(s, 1H), 7.55(d, J=3.6Hz, 1H), 7.89-7.95(m, 2H), 8.04-8.10(m, 2H), 8.19(d, J=9.3Hz, 1H), 12.63(br s, 1H) |
| C-30 | i-Pr | 5-Me-thiophen-2-yl | S | 0.81(d, J=6.9Hz, 3H), 0.85(d, J=6.6Hz, 3H), 1.97(m, 1H), 2.55(s, 3H), 3.58(dd, J=6.0, 9.3Hz, 1H), 7.00(m, 1H), 7.45(s, 1H), 7.56(d, J=3.6Hz, 1H), 7.92(d, J=8.7Hz, 2H), 8.08(d, J=8.7Hz, 2H), 8.21(d, J=9.3Hz, 1H), 12.66(br s, 1H) |
| C-31 | i-Pr | 5-Et-thiophen-2-yl | R | 0.81(d, J=6.6Hz, 3H), 0.85(d, J=6.6Hz, 3H), 1.29(t, J=7.5Hz, 3H), 1.94(m, 1H), 2.91(q, J=7.5Hz, 2H), 3.58(dd, J=6.3, 9.3Hz, 1H), 7.03(d, J=3.6Hz, 1H), 7.46(s, 1H), 7.57(d, J=3.6Hz, 1H), 7.89-7.95(m, 2H), 8.04-8.11(m, 2H), 8.20(d, J=9.3Hz, 1H), 12.65(br s, 1H) |

TABLE 21-continued

| Example No. | R² | R⁶ | * | 1H-NMR (DMSO-d₆) |
|---|---|---|---|---|
| C-32 | i-Pr | 5-ethylthien-2-yl | R | 0.81(d, J=6.6Hz, 3H), 0.85(d, J=6.6Hz, 3H), 1.30(t, J=7.5Hz, 3H), 1.97(m, 1H), 2.91(q, J=7.5Hz, 2H), 3.58(dd, J=6.6, 9.3Hz, 1H), 7.03(m, 1H), 7.46(s, 1H), 7.57(d, J=3.9Hz, 1H), 7.92(d, J=8.4Hz, 2H), 8.08(d, J=8.4Hz, 2H), 8.20(d, J=9.3Hz, 1H), 12.65(br s, 1H) |
| C-33 | i-Pr | 5-chlorothien-2-yl | R | 0.81(d, J=6.6Hz, 3H), 0.85(d, J=6.6Hz, 3H), 1.97(m, 1H), 3.58(m, 1H), 7.36(d, J=3.9Hz, 1H), 7.59(s, 1H), 7.65(d, J=3.9Hz, 1H), 7.90-7.96(m, 2H), 8.04-8.10(m, 2H), 8.20(d, J=8.7Hz, 1H), 12.56(br s, 1H) |
| C-34 | i-Pr | 5-chlorothien-2-yl | S | 0.81(d, J=6.9Hz, 3H), 0.85(d, J=6.9Hz, 3H), 1.97(m, 1H), 3.58(t, J=6.0Hz, 1H), 7.35(d, J=3.9Hz, 1H), 7.59(s, 1H), 7.65(d, J=3.9Hz, 1H), 7.91-7.96(m, 2H), 8.04-8.09(m, 2H), 8.19(d, J=9.6Hz, 1H), 12.62(br s, 1H) |

TABLE 22

| Example No. | R² | R⁶ | * | 1H-NMR (DMSO-d₆) |
|---|---|---|---|---|
| C-35 | i-Pr | 4-fluorophenyl | R | 0.81(d, J=6.6Hz, 3H), 0.85(d, J=6.9Hz, 3H), 1.97(m, 1H), 3.58(dd, J=6.0, 8.7Hz, 1H), 7.45(t, J=8.7Hz, 2H), 7.71(s, 1H), 7.94(d, J=8.4Hz, 2H), 7.96-8.03(m, 2H), 8.08(d, J=8.4Hz, 2H), 8.20(d, J=8.7Hz, 1H), 12.65(br s, 1H) |
| C-36 | i-Pr | 3-fluoro-4-chlorophenyl | R | 0.81(d, J=6.9Hz, 3H), 0.85(d, J=6.9Hz, 3H), 1.97(m, 1H), 3.58(m, 1H), 7.77-7.89(m, 2H), 7.85(s, 1H), 7.95(d, J=8.4Hz, 2H), 8.01(m, 1H), 8.05(d, J=8.1Hz, 2H), 8.21(d, J=8.1Hz, 1H), 12.63(br s, 1H) |
| C-37 | i-Pr | 3-fluoro-4-chlorophenyl | S | 0.81(d, J=6.9Hz, 3H), 0.85(d, J=6.9Hz, 3H), 1.97(m, 1H), 3.59(m, 1H), 7.78-7.88(m, 2H), 7.84(s, 1H), 7.95(d, J=8.7Hz, 2H), 8.01(m, 1H), 8.07(d, J=8.4Hz, 2H), 8.20(d, J=8.7Hz, 1H), 12.68(br s, 1H) |
| C-38 | i-Pr | 3-fluoro-4-methylphenyl | R | 0.81(d, J=6.9Hz, 3H), 0.85(d, J=6.6Hz, 3H), 1.97(m, 1H), 2.32(s, 3H), 3.58(m, 1H), 7.52(m, 1H), 7.65-7.76(m, 2H), 7.75(s, 1H), 7.94(d, J=8.4Hz, 2H), 8.07(d, J=8.4Hz, 2H), 8.20(d, J=9.0Hz, 1H), 12.65(br s, 1H) |
| C-39 | i-Pr | 3-fluoro-4-methylphenyl | S | 0.81(d, J=6.9Hz, 3H), 0.85(d, J=6.9Hz, 3H), 1.97(m, 1H), 2.32(d, J=1.2Hz, 3H), 3.58(m, 1H), 7.52(m, 1H), 7.65-7.76(m, 3H), 7.94(d, J=8.7Hz, 2H), 8.07(d, J=8.7Hz, 2H), 8.19(m, 1H), 12.56(br s, 1H) |
| C-40 | i-Pr | 3,4-dichlorophenyl | R | 0.81(d, J=6.9Hz, 3H), 0.85(d, J=6.9Hz, 3H), 1.97(m, 1H), 3.59(m, 1H), 7.86-7.93(m, 2H), 7.89(s, 1H), 7.95(d, J=8.1Hz, 2H), 8.07(d, J=8.4Hz, 2H), 8.18-8.27(m, 2H), 12.66(br s, 1H) |
| C-41 | i-Pr | 3,4-dichlorophenyl | S | 0.81(d, J=6.9Hz, 3H), 0.85(d, J=6.9Hz, 3H), 1.97(m, 1H), 3.58(m, 1H), 7.85-7.92(m, 3H), 7.95(d, J=8.7Hz, 2H), 8.07(d, J=8.7Hz, 2H), 8.14-8.25(m, 2H), 12.63(br s, 1H) |

TABLE 23

| Example No. | R² | R⁶ | * | 1H-NMR (DMSO-d₆) |
|---|---|---|---|---|
| C-42 | i-Pr | 3,5-dimethoxyphenyl (MeO, MeO) | R | 0.81(d, J=6.9Hz, 3H), 0.85(d, J=6.9Hz, 3H), 1.97(m, 2H), 3.59(m, 1H), 3.85(s, 6H), 6.68(m, 1H), 7.08(d, J=2.4Hz, 2H), 7.77(s, 1H), 7.94(d, J=8.4Hz, 2H), 8.08(d, J=8.7Hz, 2H), 8.20(d, J=9.6Hz, 1H), 12.65(br s, 1H) |
| C-43 | i-Pr | 2-naphthyl | R | 0.82(d, J=6.6Hz, 3H), 0.86(d, J=6.9Hz, 3H), 1.98(m, 1H), 3.60(m, 1H), 7.61-7.68(m, 2H), 7.86(s, 1H), 7.96(d, J=8.4Hz, 2H), 7.98-8.14(m, 4H), 8.13(d, J=8.4Hz, 2H), 8.21(d, J=9.3Hz, 1H), 8.56(d, 0.3Hz, 1H), 12.66(br s, 1H) |
| C-44 | i-Pr | 1,3-benzodioxol-5-yl | R | 0.81(d, J=6.9Hz, 3H), 0.85(d, J=6.6Hz, 3H), 1.97(m, 1H), 3.58(m, 1H), 6.15(s, 2H), 7.13(d, J=8.4Hz, 1H), 7.44-7.50(m, 2H), 7.58(s, 1H), 7.93(d, J=8.1Hz, 2H), 8.07(d, J=8.7Hz, 2H), 8.20(d, J=9.3Hz, 1H), 12.65(br s, 1H) |
| C-45 | i-Pr | 1,3-benzodioxol-5-yl | S | 0.82(d, J=6.9Hz, 3H), 0.85(d, J=6.9Hz, 3H), 1.97(m, 1H), 3.59(dd, J=5.7, 8.7Hz, 1H), 6.15(s, 2H), 7.13(d, J=8.7Hz, 1H), 7.45-7.50(m, 2H), 7.58(s, 1H), 7.94(d, J=8.4Hz, 2H), 8.06(d, J=8.4Hz, 2H), 8.20(d, J=8.7Hz, 1H), 12.64(br s, 1H) |
| C-46 | i-Pr | 2,3-dihydro-1,4-benzodioxin-6-yl | R | 0.81(d, J=6.9Hz, 3H), 0.85(d, J=6.9Hz, 3H), 1.97(m, 1H), 3.58(t, J=6.3Hz, 1H), 4.33(s, 4H), 7.06(d, J=8.7Hz, 1H), 7.38-7.44(m, 2H), 7.57(s, 1H), 7.93(d, J=8.7Hz, 2H), 8.06(d, J=8.7Hz, 2H), 8.18(d, J=8.7Hz, 1H), 12.63(br s, 1H) |
| C-47 | i-Pr | 2,3-dihydrobenzofuran-5-yl | R | 0.81(d, J=6.6Hz, 3H), 0.85(d, J=6.9Hz, 3H), 1.96(m, 1H), 3.28(t, J=8.7Hz, 1H), 3.58(dd, J=6.3, 9.3Hz, 1H), 4.64(t, J=8.7Hz, 2H), 6.96(d, J=8.4Hz, 1H), 7.51(s, 1H), 7.69(dd, J=1.2, 8.4Hz, 1H), 7.80(d, J=1.2Hz, 1H), 7.93(d, J=8.4Hz, 2H), 8.07(d, J=8.4Hz, 2H), 8.18(d, J=9.3Hz, 1H), 12.64(br s, 1H) |

TABLE 24

| Example No. | R² | R⁶ | * | 1H-NMR (DMSO-d₆) |
|---|---|---|---|---|
| C-48 | i-Pr | 2,3-dihydrobenzofuran-5-yl | S | 0.82(d, J=6.6Hz, 3H), 0.85(d, J=6.9Hz, 3H), 1.97(m, 1H), 3.29(t, J=8.7Hz, 1H), 3.58(t, J=6.0Hz, 1H), 4.64(t, J=8.7Hz, 2H), 6.96(d, J=8.4Hz, 1H), 7.51(s, 1H), 7.69(d, J=8.7Hz, 1H), 7.81(s, 1H), 7.93(d, J=8.4Hz, 2H), 8.07(d, J=8.4Hz, 2H), 8.19(d, J=8.4Hz, 1H), 12.64(br s, 1H) |
| C-49 | i-Pr | 3,4-difluorophenyl | R | 0.82(d, J=6.9Hz, 3H), 0.85(d, J=6.9Hz, 3H), 1.97(m, 1H), 3.59(m, 1H), 7.69(m, 1H), 7.78(s, 1H), 7.81(m, 1H), 7.95(d, J=8.4Hz, 2H), 8.01-8.10(m, 3H), 8.20(d, J=8.4Hz, 1H), 12.66(br s, 1H) |
| C-50 | i-Pr | 3,4-difluorophenyl | S | 0.82(d, J=6.6Hz, 3H), 0.85(d, J=6.9Hz, 3H), 1.98(m, 1H), 3.59(m, 1H), 7.69(m, 1H), 7.79(s, 1H), 7.80(m, 1H), 7.95(d, J=8.7Hz, 2H), 8.01-8.10(m, 3H), 8.20(d, J=8.4Hz, 1H), 12.61(br s, 1H) |

TABLE 24-continued

| Example No. | R² | R⁶ | * | 1H-NMR (DMSO-d₆) |
|---|---|---|---|---|
| C-51 | i-Pr | 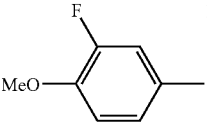 | R | 0.81(d, J=6.9Hz, 3H), 0.85(d, J=6.9Hz, 3H), 1.97(m, 1), 3.58(m, 1H), 3.94(s, 3H), 7.39(m, 1H), 7.65(s, 1H), 7.71-7.85(m, 2H), 7.94(d, J=8.1Hz, 2H), 8.06(d, J=8.1Hz, 2H), 8.20(d, J=9.3Hz, 1H), 12.66(br s, 1H) |
| C-52 | i-Bu | 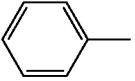 | R | 0.73(d, J=6.6Hz, 3H), 0.83(d, J=6.6Hz, 3H), 1.34-1.52(m, 2H), 1.61(m, 1H), 3.73(m, 1H), 7.52-7.64(m, 3H), 7.74(s, 1H), 7.90-7.98(m, 4H), 8.14(d, J=8.4Hz, 2H), 8.33(d, J=8.7Hz, 1H), 12.65(br s, 1H) |
| C-53 | i-Bu | 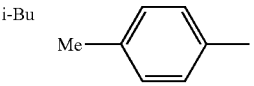 | R | 0.73(d, J=6.3Hz, 3H), 0.83(d, J=6.9Hz, 3H), 1.33-1.50(m, 2H), 1.61(m, 1H), 2.39(s, 3H), 3.72(m, 1H), 7.40(d, J=8.1Hz, 2H), 7.65(s, 1H), 7.83(d, J=8.1Hz, 2H), 7.93(d, J=8.4Hz, 2H), 8.10(d, J=8.4Hz, 2H), 8.30(d, J=8.4Hz, 1H), 12.63(br s, 1H) |
| C-54 | i-Bu | 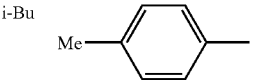 | S | 0.73(d, J=6.6Hz, 3H), 0.83(d, J=6.6Hz, 3H), 1.33-1.52(m, 2H), 1.61(m, 1H), 2.39(s, 3H), 3.72(m, 1H), 7.40(d, J=8.4Hz, 2H), 7.66(s, 1H), 7.83(d, J=8.1Hz, 2H), 7.93(d, J=8.7Hz, 2H), 8.10(d, J=8.7Hz, 2H), 8.31(d, J=9.3Hz, 1H), 12.63(br s, 1H) |

TABLE 25

| Example No. | R² | R⁶ | * | 1H-NMR (DMSO-d₆) |
|---|---|---|---|---|
| C-55 | i-Bu | 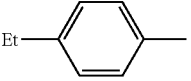 | R | 0.73(d, J=6.6Hz, 3H), 0.83(d, J=6.3Hz, 3H), 1.25(t, J=7.5Hz, 3H), 1.30-1.50(m, 2H), 1.61(m, 1H), 2.69(q, J=7.5Hz, 2H), 3.72(m, 1H), 7.43(d, J=8.1Hz, 2H), 7.66(s, 1H), 7.85(d, J=8.1Hz, 2H), 7.92(d, J=8.4Hz, 2H), 8.10(d, J=8.4Hz, 2H), 8.32(d, J=8.4Hz, 1H), 12.65(br s, 1H) |
| C-56 | i-Bu | 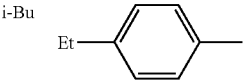 | S | 0.74(d, J=6.6Hz, 3H), 0.84(d, J=6.6Hz, 3H), 1.23(t, J=7.5Hz, 3H), 1.32-1.52(m, 2H), 1.61(m, 1H), 2.70(q, J=7.5Hz, 2H), 3.73(m, 1H), 7.44(d, J=8.1Hz, 2H), 7.67(s, 1H), 7.86(d, J=8.1Hz, 2H), 7.90-7.96(m, 2H), 8.08-8.14(m, 2H), 8.31(d, J=9.0Hz, 1H), 12.63(br s, 1H) |
| C-57 | i-Bu | 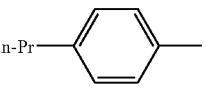 | R | 0.73(d, J=6.6Hz, 3H), 0.83(d, J=6.6Hz, 3H), 0.92(t, J=7.5Hz, 3H), 1.32-1.50(m, 2H), 1.55-1.72(m, 3H), 2.64(t, J=7.5Hz, 2H), 3.72(m, 1H), 7.41(d, J=8.4Hz, 2H), 7.66(s, 1H), 7.84(d, J=8.4Hz, 2H), 7.92(d, J=8.4Hz, 2H), 8.10(d, J=8.7Hz, 2H), 8.31(d, J=8.1Hz, 1H), 12.66(br s, 1H) |
| C-58 | i-Bu | 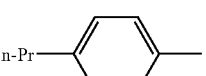 | S | 0.73(d, J=6.6Hz, 3H), 0.83(d, J=6.6Hz, 3H), 0.92(t, J=7.5Hz, 3H), 1.33-1.50(m, 2H), 1.53-1.72(m, 3H), 2.64(t, J=7.8Hz, 2H), 3.73(m, 1H), 7.41(d, J=8.4Hz, 2H), 7.66(s, 1H), 7.84(d, J=8.4Hz, 2H), 7.93(d, J=8.7Hz, 2H), 8.10(d, J=8.7Hz, 2H), 8.31(d, J=9.0Hz, 1H), 12.63(br s, 1H) |
| C-59 | i-Bu | 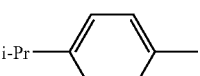 | R | 0.73(d, J=6.6Hz, 3H), 0.83(d, J=6.9Hz, 3H), 1.25(d, J=6.9Hz, 6H), 1.33-1.51(m, 2H), 1.61(m, 1H), 2.98(m, 1H), 3.73(m, 1H), 7.47(d, J=8.4Hz, 2H), 7.66(s, 1H), 7.86(d, J=8.4Hz, 2H), 7.93(d, J=8.4Hz, 2H), 8.11(d, J=8.4Hz, 2H), 8.31(d, J=8.7Hz, 1H), 12.64(br s, 1H) |

TABLE 26

| Example No. | R² | R⁶ | * | 1H-NMR (DMSO-d₆) |
|---|---|---|---|---|
| C-60 | i-Bu | 4-(i-Pr)-C₆H₄- | S | 0.73(d, J=6.3Hz, 3H), 0.83(d, J=6.3Hz, 3H), 1.25(d, J=6.9Hz, 6H), 1.32-1.50(m, 2H), 1.61(m, 1H), 2.98(m, 1H), 3.73(m, 1H), 7.46(d, J=8.4Hz, 2H), 7.66(s, 1H), 7.85(d, J=8.4Hz, 2H), 7.93(d, J=8.4Hz, 2H), 8.10(d, J=8.4Hz, 2H), 8.32(d, J=8.4Hz, 1H), 12.65(br s, 1H) |
| C-61 | i-Bu | 4-(MeS)-C₆H₄- | R | 0.73(d, J=6.3Hz, 3H), 0.83(d, J=6.6Hz, 3H), 1.33-1.50(m, 2H), 1.61(m, 1H), 2.56(s, 3H), 3.72(m, 1H), 7.42-7.48(m, 2H), 7.67(s, 1H), 7.83-7.88(m, 2H), 7.90-7.96(m, 2H), 8.07-8.12(m, 2H), 8.30(br d, J=7.2Hz, 1H), 12.65(br s, 1H) |
| C-62 | i-Bu | 4-(MeS)-C₆H₄- | S | 0.73(d, J=6.3Hz, 3H), 0.83(d, J=6.9Hz, 3H), 1.33-1.51(m, 2H), 1.61(m, 1H), 2.56(s, 3H), 3.73(m, 1H), 7.45(d, J=8.4Hz, 2H), 7.68(s, 1H), 7.86(d, J=8.4Hz, 2H), 7.93(d, J=8.4Hz, 2H), 8.10(d, J=8.4Hz, 2H), 8.32(d, J=7.2Hz, 1H), 12.65(br s, 1H) |
| C-63 | i-Bu | 4-(MeO)-C₆H₄- | R | 0.73(d, J=6.3Hz, 3H), 0.83(d, J=6.6Hz, 3H), 1.33-1.50(m, 2H), 1.61(m, 1H), 3.72(m, 1H), 3.85(s, 3H), 7.11-7.17(m, 2H), 7.57(s, 1H), 7.84-7.90(m, 2H), 7.90-7.95(m, 2H), 8.06-8.11(m, 2H), 8.31(d, J=9.0Hz, 1H), 12.65(br s, 1H) |
| C-64 | i-Bu | 4-(MeO)-C₆H₄- | S | 0.73(d, J=6.6Hz, 3H), 0.83(d, J=6.6Hz, 3H), 1.33-1.50(m, 2H), 1.61(m, 1H), 3.72(m, 1H), 3.85(s, 3H), 7.14(d, J=9.0Hz, 2H), 7.57(s, 1H), 7.88(d, J=9.0Hz, 2H), 7.92(d, J=8.7Hz, 2H), 8.09(d, J=8.7Hz, 2H), 8.31(m, 1H), 12.68(br s, 1H) |
| C-65 | i-Bu | 4-Br-C₆H₄- | R | 0.73(d, J=6.6Hz, 3H), 0.83(d, J=6.6Hz, 3H), 1.34-1.50(m, 2H), 1.61(m, 1H), 3.73(m, 1H), 7.77-7.84(m, 3H), 7.85-7.91(m, 2H), 7.91-7.97(m, 2H), 8.07-8.12(m, 2H), 8.31(d, J=8.7Hz, 1H), 12.63(br s, 1H) |

TABLE 27

| Example No. | R² | R⁶ | * | 1H-NMR (DMSO-d₆) |
|---|---|---|---|---|
| C-66 | i-Bu | 4-Br-C₆H₄- | S | 0.73(d, J=6.3Hz, 3H), 0.83(d, J=6.9Hz, 3H), 1.33-1.45(m, 2H), 1.60(m, 1H), 3.72(m, 1H), 7.79(s, 1H), 7.81(d, J=8.7Hz, 2H), 7.89(d, J=8.7Hz, 2H), 7.94(d, J=8.7Hz, 2H), 8.10(d, J=8.4Hz, 2H), 8.31(m, 1H), 12.55(br s, 1H) |
| C-67 | i-Bu | 4-Cl-C₆H₄- | R | 0.73(d, J=6.6Hz, 3H), 0.83(d, J=6.6Hz, 3H), 1.33-1.50(m, 2H), 1.61(m, 1H), 3.72(m, 1H), 7.68(d, J=9.0Hz, 2H), 7.78(s, 1H), 7.94(d, J=8.7Hz, 2H), 7.96(d, J=9.0Hz, 2H), 8.10(d, J=8.7Hz, 2H), 8.32(m, 1H), 12.57(br s, 1H) |
| C-68 | i-Bu | 4-Cl-C₆H₄- | S | 0.73(d, J=6.6Hz, 3H), 0.83(d, J=6.6Hz, 3H), 1.33-1.50(m, 2H), 1.61(m, 1H), 3.72(m, 1H), 7.68(d, J=8.7Hz, 2H), 7.78(s, 1H), 7.94(d, J=8.7Hz, 2H), 7.96(d, J=8.7Hz, 2H), 8.10(d, J=8.7Hz, 2H), 8.32(m, 1H), 12.63(br s, 1H) |
| C-69 | i-Bu | 4-F-C₆H₄- | S | 0.73(d, J=6.6Hz, 3H), 0.83(d, J=6.6Hz, 3H), 1.32-1.50(m, 2H), 1.60(m, 1H), 3.73(m, 1H), 7.41-7.50(m, 2H), 7.71(s, 1H), 7.93(d, J'28.7Hz, 2H), 7.96-8.40(m, 2H), 8.10(d, J=8.7Hz, 2H), 8.33(m, 1H), 12.60(br s, 1H) |

TABLE 27-continued

| Example No. | R² | R⁶ | * | 1H-NMR (DMSO-d₆) |
|---|---|---|---|---|
| C-70 | i-Bu | 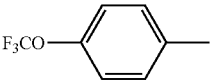 F₃CO— | R | 0.74(d, J=6.6Hz, 3H), 0.83(d, J=6.6Hz, 3H), 1.38-1.51(m, 2H), 1.61(m, 1H), 3.74(m, 1H), 7.61(d, J=8.4Hz, 2H), 7.81(s, 1H), 7.94(d, J=8.4Hz, 2H), 8.04-8.14(m, 4H), 8.33(d, J=9.0Hz, 1H), 12.64(br s, 1H) |
| C-71 | i-Bu | 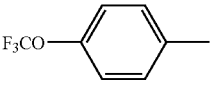 F₃CO— | S | 0.74(d, J=6.6Hz, 3H), 0.83(d, J=6.6Hz, 3H), 1.34-1.50(m, 2H), 1.61(m, 1H), 3.73(m, 1H), 7.61(d, J=8.1Hz, 2H), 7.81(s, 1H), 7.92-7.97(m, 2H), 8.05-8.13(m, 4H), 8.32(d, J=9.3Hz, 1H), 12.63(br s, 1H) |
| C-72 | i-Bu |  F₃C— | R | 0.73(d, J=6.6Hz, 3H), 0.83(d, J=6.6Hz, 3H), 1.33-1.52(m, 2H), 1.60(m, 1H), 3.73(m, 1H), 7.95(d, J=8.7Hz, 2H), 7.95(s, 1H), 7.95-8.02(m, 2H), 8.12(d, J=8.7Hz, 2H), 8.16(d, J=8.1Hz, 2H), 8.34(d, J=8.4Hz, 1H), 12.65(br s, 1H) |

TABLE 28

| Example No. | R² | R⁶ | * | 1H-NMR (DMSO-d₆) |
|---|---|---|---|---|
| C-73 | i-Bu |  F₃C— | S | 0.73(d, J=6.6Hz, 3H), 0.83(d, J=6.3Hz, 3H), 1.32-1.50(m, 2H), 1.60(m, 1H), 3.73(m, 1H), 7.92-8.02(m, 5H), 8.12(d, J=8.7Hz, 2H), 8.16(d, J=8.1Hz, 2H), 8.34(m, 1H), 12.64(br s, 1H) |
| C-74 | i-Bu | 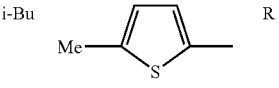 Me— (thiophene) | R | 0.73(d, J=6.6Hz, 3H), 0.83(d, J=6.6Hz, 3H), 1.33-1.50(m, 2H), 1.60(m, 1H), 2.55(s, 3H), 3.72(m, 1H), 6.99(dd, J=1.2, 3.6Hz, 1H), 7.44(s, 1H), 7.55(d, J=3.6Hz, 1H), 7.88-7.94(m, 2H), 8.05-8.11(m, 2H), 8.31(d, J=6.9Hz, 1H), 12.63(br s, 1H) |
| C-75 | i-Bu | 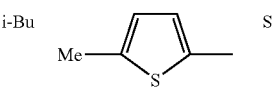 Me— (thiophene) | S | 0.73(d, J=6.6Hz, 3H), 0.83(d, J=6.6Hz, 3H), 1.33-1.50(m, 2H), 1.60(m, 1H), 2.55(s, 3H), 3.72(m, 1H), 7.00(dt, J=3.6, 0.9Hz, 1H), 7.45(s, 1H), 7.56(d, J=3.6Hz, 1H), 7.89-7.94(m, 2H), 8.06-8.12(m, 2H), 8.32(d, J=8.7Hz, 1H), 12.64(br s, 1H) |
| C-76 | i-Bu | 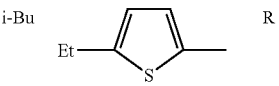 Et— (thiophene) | R | 0.73(d, J=6.3Hz, 3H), 0.83(d, J=6.6Hz, 3H), 1.30(t, J=7.5Hz, 3H), 1.33-1.50(m, 2H), 1.60(m, 1H), 2.91(q, J=7.5Hz, 2H), 3.72(m, 1H), 7.03(d, J=3.6Hz, 1H), 7.46(s, 1H), 7.58(d, J=3.6Hz, 1H), 7.91(d, J=8.4Hz, 2H), 8.09(d, J=8.4Hz, 2H), 8.32(d, J=8.4Hz, 1H), 12.64(br s, 1H) |
| C-77 | i-Bu | 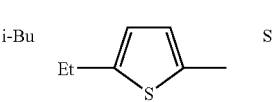 Et— (thiophene) | S | 0.73(d, J=6.6Hz, 3H), 0.83(d, J=6.6Hz, 3H), 1.29(t, J=7.5Hz, 3H), 1.33-1.51(m, 2H), 1.60(m, 1H), 2.90(q, J=7.5Hz, 2H), 3.72(m, 1H), 7.03(d, J=3.6Hz, 1H), 7.45(s, 1H), 7.57(d, J=3.6Hz, 1H), 7.88-7.94(m, 2H), 8.05-8.11(m, 2H), 8.31(d, J=8.7Hz, 1H), 12.63(br s, 1H) |
| C-78 | i-Bu | 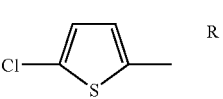 Cl— (thiophene) | R | 0.73(d, J=6.6Hz, 3H), 0.83(d, J=6.6Hz, 3H), 1.33-1.50(m, 2H), 1.60(m, 1H), 3.72(m, 1H), 7.36(d, J=3.6Hz, 1H), 7.59(s, 1H), 7.65(d, J=3.6Hz, 1H), 7.89-7.96(m, 2H), 8.04-8.11(m, 2H), 8.32(d, J=8.4Hz, 1H), 12.64(br s, 1H) |

TABLE 29

| Example No. | R² | R⁶ | * | 1H-NMR (DMSO-d₆) |
|---|---|---|---|---|
| C-79 | i-Bu | 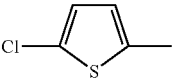 5-chlorothiophen-2-yl | S | 0.73(d, J=6.6Hz, 3H), 0.83(d, J=6.6Hz, 3H), 1.34-1.50(m, 2H), 1.60(m, 1H), 3.72(m, 1H), 7.35(d, J=3.9Hz, 1H), 7.59(m, 1H), 7.65(d, J=3.9Hz, 1H), 7.90-7.95(m, 2H), 8.05-8.11(m, 2H), 8.32(d, J=7.8Hz, 1H), 12.65(br s, 1H) |
| C-80 | i-Bu | 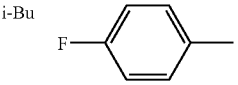 4-fluorophenyl | R | 0.74(d, J=6.6Hz, 3H), 0.84(d, J=6.6Hz, 3H), 1.34-1.51(m, 2H), 1.61(m, 1H), 3.73(m, 1H), 7.46(t, J=8.7Hz, 2H), 7.72(s, 1H), 7.94(d, J=8.4Hz, 2H), 7.96-8.05(m, 2H), 8.10(d, J=8.4Hz, 2H), 8.32(d, J=8.7Hz, 1H), 12.65(br s, 1H) |
| C-81 | i-Bu | 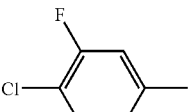 4-chloro-3-fluorophenyl | R | 0.73(d, J=6.3Hz, 3H), 0.83(d, J=6.6Hz, 3H), 1.30-1.50(m, 2H), 1.60(m, 1H), 3.72(m, 1H), 7.78-7.88(m, 3H), 7.94(d, J=8.7Hz, 2H), 8.01(dd, J=1.8, 10.2Hz, 1H), 8.08(d, J=8.4Hz, 2H), 8.33(d, J=7.8Hz, 1H), 12.66(br s, 1H) |
| C-82 | i-Bu | 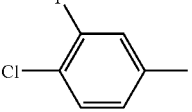 4-chloro-3-fluorophenyl | S | 0.73(d, J=6.6Hz, 3H), 0.83(d, J=6.9Hz, 3H), 1.32-1.52(m, 2H), 1.61(m, 1H), 3.73(m, 1H), 7.78-7.89(m, 3H), 7.95(d, J=8.4Hz, 2H), 8.02(dd, J=1.8, 10.2Hz, 1H), 8.08(d, J=8.7Hz, 2H), 8.33(d, J=8.4Hz, 1H), 12.64(br s, 1H) |
| C-83 | i-Bu | 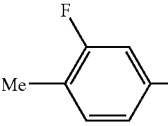 3-fluoro-4-methylphenyl | R | 0.73(d, J=6.6Hz, 3H), 0.83(d, J=6.9Hz, 3H), 1.32-1.50(m, 2H), 1.60(m, 1H), 2.32(d, J=1.5Hz, 3H), 3.73(m, 1H), 7.52(m, 1H), 7.65-7.78(m, 2H), 7.75(s, 1H), 7.94(d, J=8.7Hz, 2H), 8.08(d, J=8.7Hz, 2H), 8.33(d, J=8.4Hz, 1H), 12.60(br s, 1H) |
| C-84 | i-Bu | 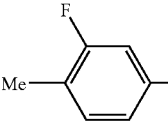 3-fluoro-4-methylphenyl | S | 0.73(d, J=6.6Hz, 3H), 0.83(d, J=6.6Hz, 3H), 1.32-1.50(m, 2H), 1.61(m, 1H), 2.32(d, J=1.2Hz, 3H), 3.72(m, 1H), 7.52(m, 1H), 7.65-7.77(m, 2H), 7.75(s, 1H), 7.94(d, J=8.7Hz, 2H), 8.08(d, J=8.7Hz, 2H), 8.32(m, 1H), 12.60(br s, 1H) |

TABLE 30

| Example No. | R² | R⁶ | * | 1H-NMR (DMSO-d₆) |
|---|---|---|---|---|
| C-85 | i-Bu | 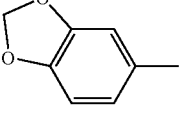 benzo[1,3]dioxol-5-yl | R | 0.73(d, J=6.6Hz, 3H), 0.83(d, J=6.6Hz, 3H), 1.32-1.50(m, 2H), 1.60(m, 1H), 3.72(m, 1H), 6.15(s, 2H), 7.13(d, J=8.4Hz, 2H), 7.44-7.50(m, 2H), 7.58(s, 1H), 7.93(d, J=8.7Hz, 2H), 8.07(d, J=8.4Hz, 2H), 8.32(d, J=8.1Hz, 1H), 12.64(br s, 1H) |
| C-86 | i-Bu | 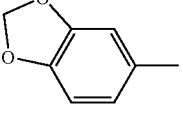 benzo[1,3]dioxol-5-yl | S | 0.73(d, J=6.6Hz, 3H), 0.83(d, J=6.6Hz, 3H), 1.34-1.50(m, 2H), 1.60(m, 1H), 3.72(m, 1H), 6.15(s, 2H), 7.13(d, J=8.4Hz, 2H), 7.45-7.50(m, 2H), 7.58(s, 1H), 7.93(d, J=8.4Hz, 2H), 8.07(d, J=8.4Hz, 2H), 8.31(d, J=9.0Hz, 1H), 12.63(br s, 1H) |
| C-87 | i-Bu | 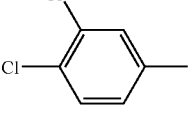 3,4-dichlorophenyl | R | 0.73(d, J=6.6Hz, 3H), 0.83(d, J=6.6Hz, 3H), 1.33-1.50(m, 2H), 1.60(m, 1H), 3.72(m, 1H), 7.85-7.93(m, 2H), 7.89(s, 1H), 7.95(d, J=8.4Hz, 2H), 8.08(d, J=8.7Hz, 2H), 8.23(d, J=1.8Hz, 1H), 8.32(d, J=7.8Hz, 1H), 12.64(br s, 1H) |
| C-88 | i-Bu | 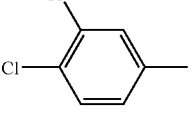 3,4-dichlorophenyl | S | 0.73(d, J=6.3Hz, 3H), 0.83(d, J=6.9Hz, 3H), 1.33-1.60(m, 2H), 1.61(m, 1H), 3.72(m, 1H), 7.85-7.98(m, 3H), 7.95(d, J=8.4Hz, 2H), 8.08(d, J=8.4Hz, 2H), 8.22(d, J=1.8Hz, 1H), 8.31(m, 1H), 12.60(br s, 1H) |

TABLE 30-continued

| Example No. | R² | R⁶ | * | 1H-NMR (DMSO-d₆) |
|---|---|---|---|---|
| C-89 | i-Bu | 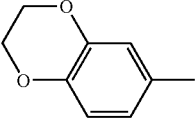 | R | 0.73(d, J=6.6Hz, 3H), 0.83(d, J=6.9Hz, 3H), 1.34-1.50(m, 2H), 1.60(m, 1H), 3.72(m, 1H), 4.33(s, 4H), 7.06(d, J=8.7Hz, 1H), 7.39-7.44(m, 2H), 7.58(s, 1H), 7.92(d, J=8.4Hz, 2H), 8.07(d, J=8.4Hz, 2H), 8.30(d, J=6.0Hz, 1H), 12.63(br s, 1H) |
| C-90 | i-Bu | 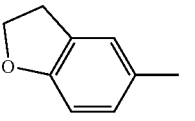 | R | 0.73(d, J=6.3Hz, 3H), 0.83(d, J=6.3Hz, 3H), 1.34-1.50(m, 2H), 1.61(m, 1H), 3.29(t, J=8.7Hz, 1H), 3.72(m, 1H), 4.64(t, J=8.7Hz, 2H), 6.96(d, J=8.4Hz, 1H), 7.51(s, 1H), 7.69(dd, J=1.2, 8.4Hz, 1H), 7.80(d, J=1.2Hz, 1H), 7.92(d, J=8.4Hz, 2H), 8.07(d, J=8.4Hz, 2H), 8.30(d, J=9.0Hz, 1H), 12.64(br s, 1H) |

TABLE 31

| Example No. | R² | R⁶ | * | 1H-NMR (DMSO-d₆) |
|---|---|---|---|---|
| C-91 | i-Bu | 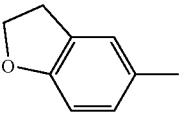 | S | 0.73(d, J=6.3Hz, 3H), 0.83(d, J=6.6Hz, 3H), 1.34-1.50(m, 2H), 1.60(m, 1H), 3.29(t, J=8.7Hz, 1H), 3.72(m, 1H), 4.64(t, J=8.7Hz, 2H), 6.96(d, J=8.4Hz, 1H), 7.51(s, 1H), 7.69(d, J=8.4Hz, 1H), 7.81(s, 1H), 7.92(d, J=8.7Hz, 2H), 8.07(d, J=8.7Hz, 2H), 8.28(br s, 1H), 12.64(br s, 1H) |
| C-92 | i-Bu | 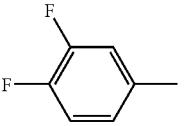 | R | 0.72(d, J=6.6Hz, 3H), 0.83(d, J=6.3Hz, 3H), 1.34-1.50(m, 2H), 1.61(m, 1H), 3.73(m, 1H), 7.63-7.86(m, 3H), 7.94(d, J=8.7Hz, 2H), 8.00-8.12(m, 3H), 8.33(br s, 1H), 12.65(br s, 1H) |
| C-93 | i-Bu | 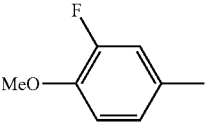 | R | 0.73(d, J=6.6Hz, 3H), 0.83(d, J=6.6Hz, 3H), 1.33-1.50(m, 2H), 1.61(m, 1H), 3.72(m, 1H), 3.94(s, 3H), 7.39(m, 1H), 7.65(s, 1H), 7.72-7.85(m, 2H), 7.93(d, J=8.4Hz, 2H), 8.07(d, J=8.4Hz, 2H), 8.32(d, J=8.7Hz, 1H), 12.62(br s, 1H) |
| C-94 | s-Bu | 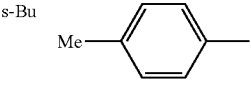 | S | 0.78(t, J=7.2Hz, 3H), 0.82(d, J=6.6Hz, 3H), 1.12(m, 1H), 1.37(m, 1H), 1.69(m, 1H), 2.39(s, 3H), 3.62(m, 1H), 7.40(d, J=8.1Hz, 2H), 7.66(s, 1H), 7.83(d, J=8.1Hz, 2H), 7.93(d, J=8.4Hz, 2H), 8.09(d, J=8.4Hz, 2H), 8.23(d, J=9.3Hz, 1H), 12.65(br s, 1H) |
| C-95 | s-Bu | 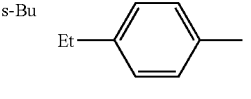 | S | 0.78(t, J=7.5Hz, 3H), 0.82(d, J=6.9Hz, 3H), 1.12(m, 1H), 1.22(t, J=7.5Hz, 3H), 1.37(m, 1H), 1.70(m, 1H), 2.69(q, J=7.5Hz, 2H), 3.62(t, J=7.2Hz, 1H), 7.43(d, J=7.8Hz, 2H), 7.66(s, 1H), 7.85(d, J=7.8Hz, 2H), 7.93(d, J=8.4Hz, 2H), 8.09(d, J=8.4Hz, 2H), 8.22(d, J=9.0Hz, 1H), 12.64(br s, 1H) |
| C-96 | s-Bu | 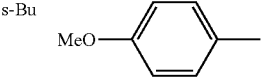 | S | 0.78(t, J=7.5Hz, 3H), 0.82(d, J=6.9Hz, 3H), 1.12(m, 1H), 1.38(m, 1H), 1.70(m, 1H), 3.62(t, J=6.9Hz, 1H), 3.85(s, 3H), 7.11-7.17(m, 2H), 7.57(s, 1H), 7.84-7.90(m, 2H), 7.90-7.96(m, 2H), 8.05-8.11(m, 2H), 8.20(d, J=9.0Hz, 1H), 12.64(br s, 1H) |

TABLE 32

| Example No. | R² | R⁶ | * | 1H-NMR (DMSO-d₆) |
|---|---|---|---|---|
| C-97 | s-Bu | 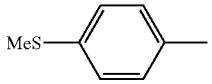 | S | 0.78(t, J=7.5Hz, 3H), 0.82(d, J=6.6Hz, 3H), 1.11(m, 1H), 1.38(m, 1H), 1.70(m, 1H), 2.56(s, 3H), 3.62(dd, J=6.0, 9.3Hz, 1H), 7.45(d, J=8.4Hz, 2H), 7.67(s, 1H), 7.85(d, J=8.4Hz, 2H), 7.93(d, J=8.4Hz, 2H), 8.09(d, J=8.4Hz, 2H), 8.22(d, J=9.3Hz, 1H), 12.62(br s, 1H) |
| C-98 | s-Bu | 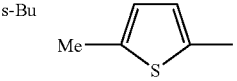 | S | 0.77(t, J=7.5Hz, 3H), 0.82(d, J=6.6Hz, 3H), 1.12(m, 1H), 1.37(m, 1H), 1.70(m, 1H), 2.55(s, 3H), 3.61(dd, J=6.3, 9.0Hz, 1H), 6.99(dd, J=0.9, 3.6Hz, 1H), 7.44(s, 1H), 7.55(d, J=3.6Hz, 1H), 7.89-7.94(m, 2H), 8.05-8.10(m, 2H), 8.22(d, J=9.0Hz, 1H), 12.63(br s, 1H) |
| C-99 | s-Bu | 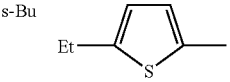 | S | 0.78(t, J=7.2Hz, 3H), 0.82(d, J=6.9Hz, 3H), 1.12(m, 1H), 1.30(t, J=7.5Hz, 3H), 1.35(m, 1H), 1.70(m, 1H), 2.91(q, J=7.5Hz, 2H), 3.62(m, 1H), 7.03(m, 1H), 7.45(s, 1H), 7.57(d, J=3.6Hz, 1H), 7.92(d, J=8.4Hz, 2H), 8.08(d, J=8.4Hz, 2H), 8.21(d, J=9.0Hz, 1H), 12.63(br s, 1h) |
| C-100 | s-Bu | 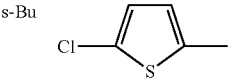 | S | 0.77(t, J=7.5Hz, 3H), 0.81(d, J=6.9Hz, 3H), 1.12(m, 1H), 1.37(m, 1H), 1.70(m, 1H), 3.61(m, 1H), 7.36(d, J=3.9Hz, 1H), 7.59(s, 1H), 7.65(d, J=3.9Hz, 1H), 7.90-7.97(m, 2H), 8.04-8.11(m, 2H), 8.23(d, J=9.0Hz, 1H), 12.62(br s, 1H) |
| C-101 | s-Bu | 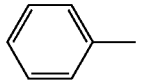 | S | 0.78(t, J=7.5Hz, 3H), 0.82(d, J=6.9Hz, 3H), 1.12(m, 1H), 1.38(m, 1H), 1.71(m, 1H), 3.63(m, 1H), 7.552-7.64(m, 3H), 7.73(s, 1H), 7.91-7.97(m, 4H), 8.11(d, J=8.4Hz, 2H), 8.22(d, J=9.3Hz, 1H), 12.64(br s, 1H) |
| C-102 | s-Bu | 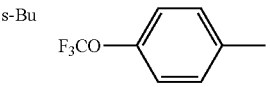 | S | 0.78(t, J=7.5Hz, 3H), 0.82(d, J=6.9Hz, 3H), 1.12(m, 1H), 1.38(m, 1H), 1.70(m, 1H), 3.62(dd, J=6.3, 8.4Hz, 1H), 7.61(d, J=8.7Hz, 2H), 7.80(s, 2H), 7.95(d, J=8.4Hz, 2H), 8.04-8.13(m, 4H), 8.23(d, J=8.4Hz, 1H), 12.63(br s, 1H) |

TABLE 33

| Example No. | R² | R⁶ | * | 1H-NMR (DMSO-d₆) |
|---|---|---|---|---|
| C-103 | s-Bu | 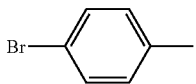 | S | 0.78(t, J=7.5Hz, 3H), 0.82(d, J=6.9Hz, 3H), 1.12(m, 1H), 1.38(m, 1H), 1.70(m, 1H), 3.62(t, J=7.2Hz, 1H), 7.79(s, 1H), 7.81(d, J=8.4Hz, 2H), 7.89(d, J=8.4Hz, 2H), 7.94(d, J=8.4Hz, 2H), 8.09(d, J=8.4Hz, 2H), 8.23(d, J=9.6Hz, 1H), 12.65(br s, 1H) |
| C-104 | s-Bu | 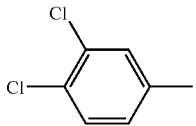 | S | 0.78(t, J=7.5Hz, 3H), 0.82(d, J=6.9Hz, 3H), 1.16(m, 1H), 1.36(m, 1H), 1.70(m, 1H), 3.62(m, 1H), 7.85-7.92(m, 3H), 7.95(d, J=8.4Hz, 2H), 8.07(d, J=8.7Hz, 2H), 8.23(m, 1H), 12.60(br s, 1H) |
| C-105 | s-Bu | 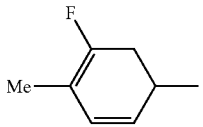 | S | 0.78(t, J=7.5Hz, 3H), 0.82(d, J=6.9Hz, 3H), 1.12(m, 1H), 1.38(m, 1H), 1.69(m, 1H), 2.32(d, J=1.5Hz, 3H), 3.62(m, 1H), 7.52(m, 1H), 7.66-7.76(m, 3H), 7.94(d, J=8.7Hz, 2H), 8.07(d, J=8.7Hz, 2H), 8.23(m, 1H), 12.60(br s, 1H) |

TABLE 33-continued

| Example No. | R² | R⁶ | * | 1H-NMR (DMSO-d₆) |
|---|---|---|---|---|
| C-106 | s-Bu | 4-F-C₆H₄- | S | 0.78(t, J=7.5Hz, 3H), 0.82(d, J=6.9Hz, 3H), 1.12(m, 1H), 1.37(m, 1H), 1.69(m, 1H), 3.62(m, 1H), 7.40-7.50(m, 2H), 7.71(s, 1H), 7.94(d, J=8.7Hz, 2H), 7.96-8.40(m, 2H), 8.09(d, J=8.7Hz, 2H), 8.21(m, 1H), 12.60(br s, 1H) |
| C-107 | s-Bu | 4-Cl-C₆H₄- | S | 0.78(t, J=7.5Hz, 3H), 0.82(d, J=6.9Hz, 3H), 1.12(m, 1H), 1.38(m, 1H), 1.70(m, 1H), 3.61(m, 1H), 7.68(d, J=8.7Hz, 2H), 7.78(s, 1H), 7.94(d, J=8.7Hz, 2H), 7.96(d, J=8.7Hz, 2H), 8.09(d, J=8.7Hz, 2H), 8.21(m, 1H), 12.60(br s, 1H) |
| C-108 | s-Bu | 3,4-diF-C₆H₃- | S | 0.78(t, J=7.5Hz, 3H), 0.82(d, J=6.9Hz, 3H), 1.12(m, 1H), 1.38(m, 1H), 1.70(m, 1H), 3.62(m, 1H), 7.69(m, 1H), 7.78(s, 1H), 7.80(m, 1H), 7.95(d, J=8.7Hz, 2H), 8.01-8.10(m, 3H), 8.22(br s, 1H), 12.66(br s, 1H) |
| C-109 | t-Bu | 4-Me-C₆H₄- | R | 0.91(s, 9H), 2.39(s, 3H), 3.48(d, J=7.2Hz, 1H), 7.40(d, J=8.1Hz, 2H), 7.66(s, 1H), 7.83(d, J=8.1Hz, 2H), 7.94(d, J=8.4Hz, 2H), 8.06-8.18(m, 3H), 12.58(br s, 1H) |

TABLE 34

| Example No. | R² | R⁶ | * | 1H-NMR (DMSO-d₆) |
|---|---|---|---|---|
| C-110 | t-Bu | 5-Me-thiophen-2-yl | R | 0.91(s, 9H), 2.55(s, 3H), 3.48(d, J=6.3Hz, 1H), 6.99(m, 1H), 7.44(s, 1H), 7.55(d, J=3.6Hz, 1H), 7.92(d, J=8.4Hz, 2H), 8.04-8.18(m, 3H), 12.66(br s, 1H) |
| C-111 | HOOC—CH₂— | 4-Me-C₆H₄- | R | 2.39(s, 3H), 2.47(m, 1H), 2.64(dd, J=6.3, 16.2Hz, 1H), 4.13(m, 1H), 7.40(d, J=7.8Hz, 2H), 7.66(s, 1H), 7.82(d, J=8.1Hz, 2H), 7.94(d, J=9.0Hz, 2H), 8.09(d, J=8.7Hz, 2H), 8.38(m, 1H), 12.10-13.10(m, 2H) |
| C-112 | HOOC—CH₂— | 4-Me-C₆H₄- | S | 2.39(s, 3H), 2.47(dd, J=6.9, 16.2Hz, 1H), 2.64(dd, J=6.0, 16.2Hz, 1H), 4.13(m, 1H), 7.40(d, J=8.1Hz, 2H), 7.66(s, 1H), 7.83(d, J=8.1Hz, 2H), 7.94(d, J=8.7Hz, 2H), 8.09(d, J=8.7Hz, 2H), 8.39(br s, 1H), 12.65(br s, 2H) |
| C-113 | HOOC—CH₂— | 4-Et-C₆H₄- | R | 1.23(t, J=7.5Hz, 3H), 2.47(m, 1H), 2.64(m, 1H), 2.69(q, J=7.5Hz, 2H), 4.13(m, 1H), 7.43(d, J=8.4Hz, 2H), 7.66(s, 1H), 7.85(d, J=8.1Hz, 2H), 7.94(d, J=8.7Hz, 2H), 8.09(d, J=8.4Hz, 2H), 8.38(m, 1H), 12.20-13.10(m, 2H) |
| C-114 | HOOC—CH₂— | 4-n-Pr-C₆H₄- | R | 0.92(t, J=7.5Hz, 3H), 1.56-1.71(m, 2H), 2.47(m, 1H), 2.58-2.68(m, 3H), 4.13(m, 1H), 7.41(d, J=8.1Hz, 2H), 7.66(s, 1H), 7.84(d, J=8.4Hz, 2H), 7.94(d, J=8.7Hz, 2H), 8.09(d, J=8.7Hz, 2H), 8.38(m, 1H), 12.20-13.00(m, 2H) |
| C-115 | HOOC—CH₂— | 4-CF₃-C₆H₄- | R | 2.47(m, 1H), 2.64(dd, J=6.6, 16.5Hz, 1H), 4.13(m, 1H), 7.92-8.03(m, 5H), 8.12(d, J=8.4Hz, 2H), 8.16(d, J=8.1Hz, 2H), 8.40(m, 1H), 12.30-13.00(m, 2H) |
| C-116 | HOOC—CH₂— | 5-Me-thiophen-2-yl | R | 2.46(m, 1H), 2.55(s, 3H), 2.63(dd, J=6.3, 16.2Hz, 1H), 4.13(m, 1H), 6.99(dd, J=1.2, 3.6Hz, 1H), 7.41(s, 1H), 7.55(d, J=3.6Hz, 1H), 7.93(d, J=8.4Hz, 2H), 8.08(d, J=9.0Hz, 2H), 8.37(m, 1H), 12.20-13.10(m, 2H) |

TABLE 34-continued

| Example No. | R² | R⁶ | * | 1H-NMR (DMSO-d₆) |
|---|---|---|---|---|
| C-117 | HOOC—CH₂— | 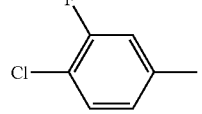 (2-F, 4-Cl-phenyl) | R | 2.49(m, 1H), 2.64(dd, J=6.3, 16.2Hz, 1H), 4.13(m, 1H), 7.76-7.90(m, 2H), 7.85(s, 1H), 7.96(d, J=8.7Hz, 2H), 8.01(m, 1H), 8.07(d, J=8.4Hz, 2H), 8.39(m, 1H), 12.20-13.10(m, 2H) |

TABLE 35

| Example No. | R² | R⁶ | * | 1H-NMR (DMSO-d₆) |
|---|---|---|---|---|
| C-118 | HOOC—CH₂— | 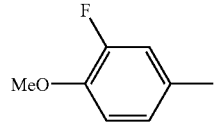 (2-F, 4-MeO-phenyl) | R | 2.47(m, 1H), 2.64(dd, J=6.3, 16.5Hz, 1H), 3.94(s, 3H), 4.13(m, 1H), 7.39(m, 1H), 7.66(s, 1H), 7.75(m, 1H), 7.81(dd, J=2.1, 12.4Hz, 1H), 7.95(d, J=8.4Hz, 2H), 8.06(d, J=8.1Hz, 2H), 8.39(m, 1H), 12.33-12.88(m, 2H) |
| C-119 | HOOC—CH₂— | 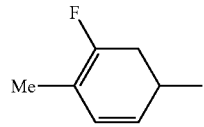 (2-F, 4-Me-phenyl) | R | 2.32(s, 3H), 2.48(m, 1H), 2.64(dd, J=6.6, 16.5Hz, 1H), 4.14(m, 1H), 7.52(m, 1H), 7.66-7.76(m, 2H), 7.75(s, 1H), 7.95(d, J=8.7Hz, 2H), 8.08(d, J=8.7Hz, 2H), 8.38(m, 1H), 12.20-13.00(m, 2H) |
| C-120 | Ph | 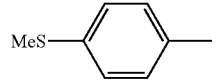 (4-MeS-phenyl) | R | 2.56(s, 3H), 4.97(d, J=8.7Hz, 1H), 7.19-7.33(m, 5H), 7.40-7.48(m, 2H), 7.64(s, 1H), 7.82-7.91(m, 4H), 7.96-8.03(m, 2H), 8.89(d, J=8.7Hz, 2H), 13.00(br s, 1H) |
| C-121 | Ph | 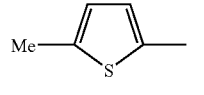 (5-Me-thiophene) | R | 2.54(s, 3H), 4.97(d, J=8.7Hz, 1H), 6.99(dd, J=1.2, 3.3Hz, 1H), 7.18-7.33(m, 5H), 7.41(s, 1H), 7.55(d, J=3.3Hz, 1H), 7.86(d, J=8.4Hz, 2H), 7.98(d, J=8.4Hz, 2H), 8.88(d, J=8.7Hz, 2H), 12.94(br s, 1H) |
| C-122 | Bn | 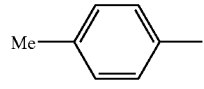 (4-Me-phenyl) | R | 2.40(s, 3H), 2.74(dd, J=9.0, 13.8Hz, 1H), 2.98(dd, J=5.4, 13.5Hz, 1H), 3.94(m, 1H), 7.10-7.26(m, 5H), 7.40(d, J=7.8Hz, 2H), 7.63(s, 1H), 7.70(d, J=8.4Hz, 2H), 7.83(d, J=7.8Hz, 2H), 7.94(d, J=8.1Hz, 2H), 8.45(d, J=8.7Hz, 1H), 12.80(br s, 1H) |
| C-123 | Bn | 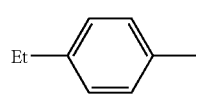 (4-Et-phenyl) | R | 1.23(t, J=7.5Hz, 3H), 2.69(q, J=7.5Hz, 2H), 2.74(m, 1H), 2.98(dd, J=5.4, 13.8Hz, 1H), 3.94(m, 1H), 7.10-7.23(m, 5H), 7.43(d, J=8.1Hz, 2H), 7.64(s, 1H), 7.70(d, J=8.4Hz, 2H), 7.86(d, J=8.4Hz, 2H), 7.95(d, J=8.4Hz, 2H), 8.45(d, J=8.7Hz, 1H), 12.80(br s, 1H) |
| C-124 | Bn | 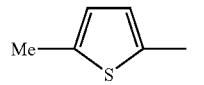 (5-Me-thiophene) | R | 2.55(s, 3H), 2.74(dd, J=9.0, 13.8Hz, 1H), 2.97(dd, J=5.4, 13.5Hz, 1H), 3.94(m, 1H), 6.99(d, J=3.6Hz, 1H), 7.10-7.23(m, 5H), 7.42(s, 1H), 7.56(d, J=3.6Hz, 1H), 7.68(d, J=8.7Hz, 2H), 7.93(d, J=8.4Hz, 2H), 8.45(d, J=8.4Hz, 1H), 12.80(br s, 1H) |

Test Example 1

Isolation and Purification of MMP

MMP-2 was purchased from Calbiochem-Novabiochem International, Inc.

In regard to MMP-8, catalytic domain ($^{99}$Phe~$^{262}$Gly) was amplified with PCR using commercial available Human Bone Marrow cDNA. This was cloned in *Escherichia. coli* expression vector pTrc99AHE inserted with His-tag sequence and enterokinase digestion-site, induced and expressed by IPTG (Isdpropyl-β-D-thiogalactopyranoside) and expressed in a insoluble fraction (Thau F. Ho, M. Walid Qoronfleh, Robert C. Wahl, Trica A. Pulvino, Karen J. Vavra, Joe Falvo, Tracey M. Banks, Patricia G. Brake and Richard B. Ciccarelli: Gene expression, purification and characterization of recombinant human neutrophil collagenase. Gene 146, (1994) 297-301, Prepared by the a improved method of this material). Isolation of MMP-8 from an insoluble fraction was carried out by dissolving in modifier (6M urea) by a usual method and purification with metal chelate chromatography. And then removing modifier (6M urea) with dialysis and refolding of the enzyme spontaneously gave activated MMP-8.

MMP-9 was isolated and purified by procedures described in as follows: Yasunori Okada, Yukio Gonoji, Katsumi Naka, Katsuro Tomita, Isao Nakanishi, Kazushi Iwata, Kyoko Yamashita, and Taro Hayakawa: Matrix metalloproteinase 9 (92-kDa gelatinase/type IV collagenase) from HT1080 human fibrosarcoma cells. Purification and activation of the precursor and enzymic properties J. Biol. Chem., 1992, 267 21712-21719, in combination with others: 1) Yasunori Okada, Tatsuhisa Morodomi, Jan J, Enghild, ko Suzuki, Atsushi Yasui, Isao Nakanishi, Guy Salvesen and Hideaki Nagase: Matrix metalloproteinase 2 from human rheumatoid synovial fibroblasts. Purification and activation of the precursor and enzymic properties. Eur. J. Biochem. 1990, 194 721-730; 2) Robin V Ward, Rosalind M Hembry; John J Reynolds and Gillian Murphy: The purification of tissue inhibitor of metalloproteinase-2 from its 72 kDa progelatinase complex. Biochem. J. 1991 278 179-187. In detail, human fibrosarcoma ATCC HT1080 cell line was cultured to confluent in Dulbecco's Modified Medium (DMEM) containing 10% fetal-calf serum at 37° C. for 48 hours. Subsequently, the medium of confluent culture was changed to serum-free DMEM medium. To obtain MMP-9, Phorbol-12-myristate-13-acetate (TPA) must be added to this serum-free DMEM medium at a concentration of 50 ng/ml. The TPA treated medium was centrifuged at 3000 rpm for 15 min and the supernatant was concentrated to 450 ml by a Toyo-Roshi UP-20 apparatus with an ultrafiltration membrane. Then, proMMP-9 in this concentrated solution was purified by using columns of Gelatin-Sepharose and Concanavalin A-Sepharose. The pool containing proMMP-9 was dialyzed, concentrated (Toyo-Roshi UP-20) and applied to columns of Sephacryl S-200 and Green A matrix for the separation from TIMPs. The obtained proMMP-9 fraction was activated by TPCK-Trypsin (Final conc. 3 µg/50 µl React Mix.).

In regard to MMP-12, catalytic domain($^{100}$Phe~$^{263}$Gly) was amplified with RT-PCR from Human Placenta Total RNA. This was cloned in *Escherichia. coli* expression vector pTrc99AHE inserted with His-tag sequence and enterokinase digestion-site, induced and expressed by IPTG (Isopropyl-β-D-thiogalactopyranoside) and expressed in a insoluble fraction. Isolation of MMP-12 from an insoluble fraction was carried out by dissolving in modifier (6M urea) by a usual method and purification with metal chelate chromatography (Ni Chelateing Sepharose). And then removing modifier (6M urea) with dialysis and refolding of the enzyme spontaneously gave activated MMP-12.

In regard to MMP-13, mRNA was prepared from carcinoma cell SW1353 derived from human cartilage stimulate by IL-1, TNF and catalytic domain ($^{104}$Tyr~$^{267}$Gly) was amplified with RT-PCR. This was cloned in *Escherichia. coli* expression vector pTrc99AHE inserted with His-tag sequence and enterokinase digestion-site, induced and expressed by IPTG (Isopropyl-β-D-thiogalactopyranoside) and expressed in a insoluble fraction. Isolation of MMP-13 from an insoluble fraction was carried out by dissolving in modifier (6M urea) by a usual method and purification with metal chelate chromatography (Ni Chelateing Sepharose). And then removing modifier (6M urea) with dialyze and refolding of the enzyme spontaneously gave activated MMP-13.

Test Example 2

Assay for Inhibitory Activities on Various Type of MMPs

The enzymatic activity on MMPs was analyzed by the method described in "C. Graham Knight, Frances Willenbrock and Gillian Murphy: A novel coumarin-labelled peptide for sensitive continuous assays of the matrix metalloproteinases: FEBS LETT., 296, (1992), 263-266". The substrate: MOCAc-Pro-Leu-Gly-Leu-A$_2$Pr(DNP)-Ala-Arg-NH$_2$ was purchased from Peptide Institute, Inc., Osaka, Japan. The measurement of the inhibitory activities (IC$_{50}$) was carried out by the following four methods;

(A) Reaction with substrate, enzyme (MMPs) and inhibitor
(B) Reaction with substrate and inhibitor, without enzyme
(C) Reaction with substrate and enzyme (MMPs), without inhibitor
(D) Reaction with substrate only IC$_{50}$ values were calculated by using the following formula and each fluorescence values of above four methods (A to D).

$$10\% \text{ inhibition} = \{1-(A-B)/(C-D)\} \times 100$$

IC$_{50}$ means the concentration required to inhibit 50% of the enzyme activity.

The value of inhibitory activity against MMP-2, MMP-8, MMP-9, MMP-12, and MMP-13 measured by above mentioned methods are shown in Table 36, 37, 38, 39, and 40 respectively.

TABLE 36

| Compound No. | MMP-2 (µM) |
| --- | --- |
| A-16 | 0.0000767 |
| A-18 | 0.0000674 |
| A-33 | 0.0000971 |
| C-4 | 0.0000934 |
| C-10 | 0.0000619 |
| C-12 | 0.0000832 |
| C-14 | 0.0000533 |
| C-15 | 0.000049 |
| C-29 | 0.0000449 |
| C-31 | 0.0000653 |
| C-124 | 0.0000926 |

TABLE 37

| Compound No. | MMP-8 (µM) |
| --- | --- |
| A-33 | 0.00291 |
| A-56 | 0.00397 |
| A-79 | 0.00111 |
| B-20 | 0.00413 |
| C-10 | 0.0039 |
| C-17 | 0.00421 |
| C-18 | 0.00419 |
| C-19 | 0.00397 |
| C-29 | 0.000567 |
| C-30 | 0.00124 |
| C-33 | 0.000781 |
| C-34 | 0.00177 |
| C-37 | 0.00433 |
| C-41 | 0.00379 |
| C-44 | 0.00359 |
| C-45 | 0.00366 |
| C-47 | 0.00107 |
| C-48 | 0.000892 |
| C-51 | 0.00263 |
| C-74 | 0.00416 |
| C-75 | 0.00198 |
| C-78 | 0.00463 |
| C-79 | 0.00286 |
| C-86 | 0.00478 |
| C-88 | 0.00437 |
| C-91 | 0.00108 |
| C-96 | 0.00229 |
| C-97 | 0.00421 |
| C-98 | 0.00103 |
| C-100 | 0.00111 |
| C-104 | 0.00489 |
| C-110 | 0.00252 |

TABLE 37-continued

| Compound No. | MMP-8 (μM) |
| --- | --- |
| C-116 | 0.00230 |
| C-124 | 0.00178 |

TABLE 38

| Compound No. | MMP-9 (μM) |
| --- | --- |
| A-18 | 0.00052 |
| A-32 | 0.000609 |
| C-12 | 0.000532 |
| C-20 | 0.000920 |
| C-22 | 0.000706 |
| C-25 | 0.000320 |
| C-29 | 0.000340 |
| C-31 | 0.000290 |
| C-33 | 0.000467 |
| C-36 | 0.000741 |
| C-124 | 0.000585 |

TABLE 39

| Compound No. | MMP-12 (μM) |
| --- | --- |
| A-6 | 0.000889 |
| A-16 | 0.000687 |
| A-18 | 0.000376 |
| A-19 | 0.000259 |
| A-20 | 0.000723 |
| A-21 | 0.000608 |
| A-23 | 0.000860 |
| A-24 | 0.000806 |
| A-25 | 0.000518 |
| A-32 | 0.000463 |
| A-38 | 0.000908 |
| A-39 | 0.000708 |
| A-40 | 0.000861 |
| A-41 | 0.000470 |
| A-56 | 0.000898 |
| A-61 | 0.000810 |
| A-63 | 0.000584 |
| A-65 | 0.000492 |
| A-66 | 0.000430 |
| A-79 | 0.000622 |
| A-81 | 0.000357 |
| A-84 | 0.000690 |
| A-102 | 0.000592 |
| A-104 | 0.000379 |
| A-108 | 0.000764 |
| A-112 | 0.000529 |
| C-1 | 0.000707 |
| C-2 | 0.000899 |
| C-3 | 0.000547 |
| C-4 | 0.000377 |
| C-8 | 0.000559 |
| C-9 | 0.000409 |
| C-10 | 0.000201 |
| C-11 | 0.000289 |
| C-12 | 0.000316 |
| C-13 | 0.000201 |
| C-14 | 0.000216 |
| C-15 | 0.000150 |
| C-16 | 0.000287 |
| C-17 | 0.000239 |
| C-18 | 0.000384 |
| C-19 | 0.000447 |
| C-20 | 0.000366 |
| C-21 | 0.000336 |
| C-22 | 0.000275 |
| C-23 | 0.000205 |
| C-25 | 0.000196 |
| C-26 | 0.000148 |
| C-27 | 0.000316 |

TABLE 39-continued

| Compound No. | MMP-12 (μM) |
| --- | --- |
| C-28 | 0.000209 |
| C-29 | 0.000368 |
| C-30 | 0.000758 |
| C-31 | 0.000566 |
| C-32 | 0.000574 |
| C-33 | 0.000535 |
| C-34 | 0.000866 |
| C-36 | 0.000245 |
| C-37 | 0.000172 |
| C-38 | 0.000245 |
| C-39 | 0.000238 |
| C-40 | 0.000575 |
| C-41 | 0.000294 |
| C-44 | 0.000649 |
| C-45 | 0.000641 |
| C-47 | 0.000264 |
| C-48 | 0.000200 |
| C-49 | 0.000834 |
| C-50 | 0.000754 |
| C-51 | 0.000266 |
| C-54 | 0.000343 |
| C-56 | 0.000289 |
| C-58 | 0.000216 |
| C-60 | 0.000335 |
| C-62 | 0.000290 |
| C-64 | 0.000432 |
| C-66 | 0.000218 |
| C-68 | 0.000295 |
| C-71 | 0.000203 |
| C-73 | 0.000251 |
| C-75 | 0.000677 |
| C-77 | 0.000676 |
| C-79 | 0.00080 |
| C-82 | 0.000233 |
| C-84 | 0.000245 |
| C-86 | 0.000545 |
| C-88 | 0.000184 |
| C-91 | 0.000184 |
| C-94 | 0.000256 |
| C-95 | 0.000172 |
| C-96 | 0.000228 |
| C-97 | 0.000239 |
| C-98 | 0.000629 |
| C-99 | 0.000649 |
| C-102 | 0.00014 |
| C-103 | 0.000177 |
| C-104 | 0.000281 |
| C-105 | 0.000174 |
| C-106 | 0.000781 |
| C-107 | 0.000257 |
| C-108 | 0.000525 |
| C-109 | 0.000951 |
| C-114 | 0.000578 |
| C-117 | 0.000967 |
| C-118 | 0.000904 |
| C-122 | 0.000877 |
| C-123 | 0.000760 |

TABLE 40

| Compound No. | MMP-13 (μM) |
| --- | --- |
| A-16 | 0.000328 |
| A-18 | 0.000263 |
| A-19 | 0.000796 |
| A-26 | 0.000943 |
| A-32 | 0.000193 |
| A-107 | 0.000658 |
| A-108 | 0.000635 |
| A-111 | 0.000465 |
| A-112 | 0.000828 |
| C-4 | 0.000404 |
| C-10 | 0.000282 |
| C-11 | 0.000739 |

TABLE 40-continued

| Compound No. | MMP-13 (μM) |
|---|---|
| C-12 | 0.000266 |
| C-13 | 0.000757 |
| C-14 | 0.000150 |
| C-15 | 0.000136 |
| C-16 | 0.000403 |
| C-17 | 0.000578 |
| C-18 | 0.000853 |
| C-25 | 0.000223 |
| C-26 | 0.000884 |
| C-27 | 0.000758 |
| C-29 | 0.000701 |
| C-31 | 0.000536 |
| C-51 | 0.000836 |
| C-59 | 0.000889 |
| C-60 | 0.000919 |
| C-95 | 0.000702 |
| C-97 | 0.000578 |
| C-99 | 0.000971 |
| C-102 | 0.000837 |
| C-113 | 0.000733 |
| C-114 | 0.000223 |
| C-115 | 0.000643 |
| C-124 | 0.000528 |

FORMULATION EXAMPLE

Formulation Example 1

Granules are prepared using the following ingredients.

| Ingredients | | |
|---|---|---|
| | Active ingredient | 10 mg |
| | Lactose | 700 mg |
| | Corn starch | 274 mg |
| | HPC-L | 16 mg |
| | | 1000 mg |

The active ingredient and lactose are made pass through a 60 mesh sieve. Corn starch is made pass through a 120 mesh sieve. They are mixed by a twin shell blender. An aqueous solution of HPC-L (low mucosity hydroxypropylcellulose) is added to the mixture and the resulting mixture is kneaded, granulated (by the extrusion with pore size 0.5 to 1 mm mesh), and dried. The dried granules thus obtained are sieved by a swing sieve (12/60 mesh) to yield the granules.

Formulation Example 2

Powders for filling capsules are prepared using the following ingredients.

| Ingredients | | |
|---|---|---|
| | Active ingredient | 10 mg |
| | Lactose | 79 mg |
| | Corn starch | 10 mg |
| | Magnesium stearate | 1 mg |
| | | 100 mg |

The active ingredient and lactose are made pass through a 60 mesh sieve. Corn starch is made pass through a 120 mesh sieve. These ingredients and magnesium stearate are mixed by a twin shell blender. 100 mg of the 10-fold trituration is filled into a No. 5 hard gelatin capsule.

Formulation Example 3

Granules for filling capsules are prepared using the following ingredients.

| Ingredients | | |
|---|---|---|
| | Active ingredient | 15 mg |
| | Lactose | 90 mg |
| | Corn starch | 42 mg |
| | HPC-L | 3 mg |
| | | 150 mg |

The active ingredient and lactose are made pass through a 60 mesh sieve. Corn starch is made pass through a 120 mesh sieve. After mixing them, an aqueous solution of HPC-L is added to the mixture and the resulting mixture is kneaded, granulated, and dried. After the dried granules are lubricated, 150 mg of that are filled into a No. 4 hard gelatin capsule.

Formulation Example 4

Hard gelatin capsules are prepared using of the following ingredients:

| | Dose (mg/capsule) |
|---|---|
| Active ingredient | 250 |
| Starch, dried | 200 |
| Magnesium stearate | 10 |
| Total | 460 |

Formulation Example 5

Capsules, each containing 80 mg of active ingredient, are made as follows.

| | |
|---|---|
| Active ingredient | 80 mg |
| Starch | 59 mg |
| Microcrystals cellulose | 59 mg |
| Magnesium stearate | 2 mg |
| Total | 200 mg |

The active ingredient, starch, cellulose, and magnesium stearate are blended, passed through a No. 45 mesh U.S. sieve, and filled into hard gelatin capsules in 200 mg quantities.

Formulation Example 6

Tablets are prepared using the following ingredients.

| Ingredients | | |
|---|---|---|
| | Active ingredient | 10 mg |
| | Lactose | 90 mg |
| | Microcrystal cellulose | 30 mg |
| | CMC-Na | 15 mg |
| | Magnesium stearate | 5 mg |
| | | 150 mg |

The active ingredient, lactose, microcrystal cellulose, and CMC-Na (carboxymethylcellulose sodium salt) are made pass through a 60 mesh sieve and then mixed. The resulting mixture is mixed with magnesium stearate to obtain the mixed powder for the tablet formulation. The mixed powder is compressed to yield tablets of 150 mg.

Formulation Example 7

A tablet is prepared using of the following ingredients:

|  | Dose (mg/tablet) |
| --- | --- |
| Active ingredient | 250 |
| Cellulose, microcrystals | 400 |
| Silicon dioxide, fumed | 10 |
| Stearic acid | 5 |
| Total | 665 |

The components are blended and compressed to form tablets each weighing 665 mg.

Formulation Example 8

Tablets, each containing 60 mg of active ingredient, are made as follows.

| Active ingredient | 60 mg |
| --- | --- |
| Starch | 45 mg |
| Microcrystals cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve, and the mixed thoroughly. The aqueous solution containing polyvinylpyrrolidone is mixed with the resultant powder, and the admixture then is passed through a No. 14 mesh U.S. sieve. The granules so produced are dried at 50° C. and passed through a No. 18 mesh U.S. sieve. The sodium carboxymethyl starch, magnesium stearate, and talc, previously passed through No. 60 mesh U.S. sieve, are then added to the granules which, after mixing, are compressed on a tablet machine to yield tablets each weighing 150 mg.

Formulation Example 9

An aerosol solution is prepared containing the following components:

|  | Weight |
| --- | --- |
| Active ingredient | 0.25 |
| Ethanol | 25.75 |
| Propellant 22 (chlorodifluoromethane) | 74.00 |
| Total | 100.00 |

The active compound is mixed with ethanol and the admixture added to a portion of the propellant 22, cooled to −30° C. and transferred to filling device. The required amount is then fed to stainless steel container and diluted with the reminder of the propellant. The valve units are then fitted to the container.

Formulation Example 10

Suppository, each containing 225 mg of active ingredient, are made as follows:

| Active ingredient | 225 mg |
| --- | --- |
| Saturated fatty acid glycerides | 2000 mg |
| Total | 2225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation Example 11

Suspensions, each containing 50 mg of active ingredient per 5 ml dose, are made as follows:

| Active ingredient | 50 mg |
| --- | --- |
| Sodium carboxymethyl cellulose | 50 mg |
| Syrup | 1.25 mL |
| Benzoic acid solution | 0.10 mL |
| Flavor | q.v. |
| Color | q.v. |
| Purified water to total | 5 mL |

The active ingredient is passed through a No. 45 U.S. sieve, and mixed with the sodium carboxymethyl cellulose and syrup to form a smooth paste. The benzoic acid solution, flavor and color are diluted with a portion of the water and added, with stirring. Sufficient water is then added to produce the required volume.

Formulation Example 12

An intravenous formulation may be prepared as follows:

| Active ingredient | 100 mg |
| --- | --- |
| Saline | 1000 mL |

The solution of the above ingredients generally is administered intravenously to a subject at a rate of 1 mL per minute.

Formulation Example 13

Composition of lyophilized preparations (in 1 vial) is made as follows:

| Active ingredient | 127 mg |
| --- | --- |
| Trisodium citrate dihydrate | 36 mg |
| Mannitol | 180 mg |

The above materials are dissolved in water for injection such that the concentration of Active ingredient is 10 mg/g. The primary freezing step is done for 3 hours at −40° C., the heat treating step for 10 hours at −10° C., and the re-freezing step for 3 hours at −40° C. Then, the primary drying step is performed for 60 hours at 0° C., 10 Pa and the secondary drying step for 5 hours at 60° C., 4 Pa. Thus the lyophilized preparation is obtained.

Formation Example 14

Ophthalmic solution (in 10 mL) is made as follows:

| Active ingredient | 1 mg |
| Concentrated glycerin | 250 mg |
| Polysorbate 80 | 200 mg |
| Sodium dihydrogenphosphate dihydrate | q.v. |
| 1 mol/L Sodium hydroxide | q.v. |
| 1 mol/L Hydrochloric acid | q.v. |
| Sterile purified water to total | 10 mL |

An ophthalmic solution containing 0.0001%, 0.001%, 0.005%, 0.05%, 0.1%, 0.5%, 1.0%, 3.0%, or 5.0% (w/v) of an active ingredient may be prepared by changing the amount of active ingredient and additive appropriately.

Formation Example 15

Nasals are prepared using the following ingredients.

| Active ingredient | 2 mg |
| Carboxyvinylpolymer | 5 mg |
| L-Arginine | 10 mg |
| Sodium chloride | 0.6 mg |
| Purified water | 82.4 mg |
| | 100 mg |

After the active ingredient is dissolved in carboxyvinylpolymer, L-arginine and sodium chloride is added to the solution. The solution's pH is adjusted and the mucosity is adjusted by adding purified water to yield the objective medical fluid.

Formation Example 16

Endermatic formulation is prepared using the following ingredients.

| Active ingredient | 10 mg |
| Isopropyl myristate | 990 mg |
| | 1000 mg |

After the active ingredient is dispersed in isopropyl myristate, the mixture is mixed with acrylic adhesive formulation (e.g. nikazole) and is attached plastered to a support to yield endermatic formulation.

Formulation Example 17

Ointment was prepared using the following ingredients.

| Active ingredient | 10 mg |
| Liquid paraffin | 75 mg |
| White petrolatum | 925 mg |
| | 1000 mg |

The active ingredient is dispersed in liquid paraffin and kneaded with white petrolatum to yield the ointment.

INDUSTRIAL APPLICABILITY

The sulfonamide derivatives having an isoxazole ring of the present invention have inhibitory activities against the matrix metalloproteinase, especially excellent inhibitory activities against plural MMPs and are useful for the treating or preventing agent for diseases caused by MMP.

The invention claimed is:

1. A compound represented by the general formula (I):

wherein W is a group represented by the formula:

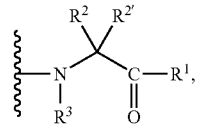

wherein $R^1$ is NHOH, hydroxy, or lower alkyloxy;

$R^2$ and $R^{2'}$ are each independently hydrogen atom, optionally substituted lower alkyl, optionally substituted aryl, optionally substituted aralkyl, optionally substituted heteroaryl, or optionally substituted heteroarylalkyl;

$R^3$ is hydrogen atom, optionally substituted lower alkyl, optionally substituted aryl, optionally substituted aralkyl, optionally substituted heteroaryl, or optionally substituted heteroarylalkyl;

$R^4$ is optionally substituted phenylene or optionally substituted thiophenylene;

$R^5$ is a group represented by the formula:

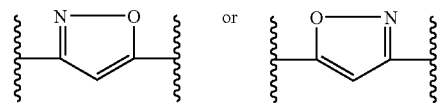

$R^6$ is optionally substituted phenyl, optionally substituted naphthyl, optionally substituted furanyl, thiophenyl, optionally substituted cyclohexyl, optionally substituted cyclohexenyl, optionally substituted benzoxolanyl, optionally substituted benzodioxolanyl, or optionally substituted benzodioxanyl;

its optically active substance, their pharmaceutically acceptable salt, or a solvate thereof.

2. A compound of claim 1, wherein W is a group represented by the formula:

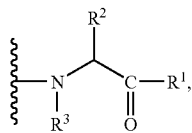

wherein $R^1$, $R^2$, and $R^3$ are as defined in claim 1, its optically active substance, their pharmaceutically acceptable salt, or a solvate thereof.

3. A compound of claim 1, wherein $R^6$ is a group represented by the formula:

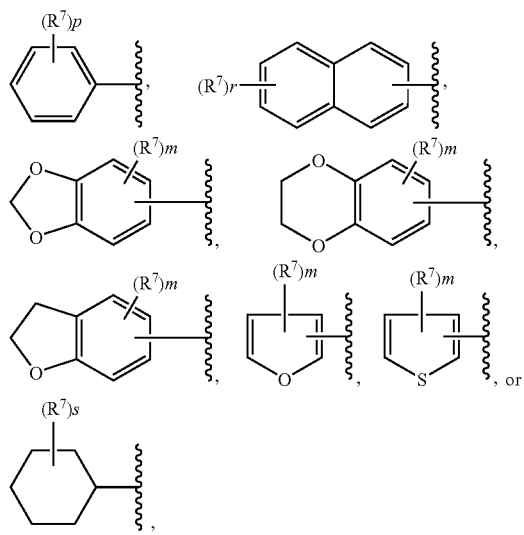

wherein $R^7$ is each independently halogen, lower alkyl, cycloalkyl, lower alkenyl, lower alkynyl, lower alkyloxy, lower alkenyloxy, lower alkylthio, halo(lower)alkyl, halo(lower)alkyloxy, halo(lower)alkylthio, hydroxy, hydroxy(lower)alkyl, carboxy, lower alkyloxycarbonyl, lower alkylsulfonyl, carbamoyl, acyl, acyloxy, nitro, cyano, optionally substituted amino, or optionally substituted aminocarbonyl; m is an integer from 0 to 3; n is an integer from 0 to 4; p is an integer from 0 to 5; q is an integer from 0 to 6; r is an integer from 0 to 7; s is an integer from 0 to 11, its optically active substance, their pharmaceutically acceptable salt, or a solvate thereof.

4. A compound of claim 1, wherein $R^1$ is hydroxy, its optically active substance, their pharmaceutically acceptable salt, or a solvate thereof.

5. A compound of claim 1, wherein $R^2$ is lower alkyl optionally substituted by halogen, hydroxy, carboxy, carbamoyl, mercapto, lower alkylthio, guanidino, amino, or cycloalkyl; aryl optionally substituted by hydroxy; aralkyl optionally substituted by halogen, hydroxy, or nitro; heteroaryl optionally substituted by hydroxy; heteroarylalkyl optionally substituted by hydroxy; or hydrogen atom, its optically active substance, their pharmaceutically acceptable salt, or a solvate thereof.

6. A compound of claim 5, wherein $R^2$ is hydrogen atom, methyl, isopropyl, s-butyl, isobutyl, t-butyl, hydroxymethyl, 1-hydroxyethyl, 2-hydroxyethyl, carboxymethyl, carboxyethyl, carbamoylmethyl, carbamoylethyl, mercaptomethyl, 2-methylthioethyl, cyclohexylmethyl, 3-guanidinopropyl, 4-aminobutyl, phenyl, 4-hydroxyphenyl, benzyl, 4-hydroxybenzyl, 4-fluorobenzyl, 4-chlorobenzyl, 4-bromobenzyl, 4-nitrobenzyl, phenylethyl, 1-naphthylmethyl, 2-naphthylmethyl, biphenylmethyl, indolyl, thienyl, indol-3-ylmethyl, (5-hydroxyindol-3-yl)methyl, thiophen-2-ylmethyl, imidazolylmethyl, benzoxazol-2-ylmethyl, benzthiazol-2-ylmethyl, or benzimidazol-2-ylmethyl, its optically active substance, their pharmaceutically acceptable salt, or a solvate thereof.

7. A compound of claim 1, wherein $R^3$ is hydrogen atom, its optically active substance, their pharmaceutically acceptable salt, or a solvate thereof.

8. A compound of claim 1, wherein $R^4$ is 1,4-phenylene or 2,5-thiophendiyl, its optically active substance, their pharmaceutically acceptable salt, or a solvate thereof.

9. A compound of claim 1, wherein $R^6$ is a group represented by the formula:

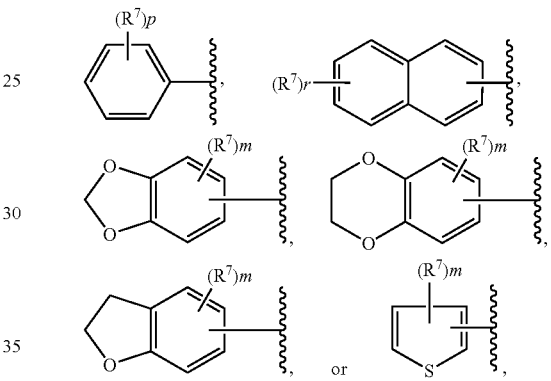

wherein $R^7$, m, p, r, and s are as defined in claim 3, its optically active substance, their pharmaceutically acceptable salt, or a solvate thereof.

10. A pharmaceutical composition which contains a compound of claim 1 as an active ingredient.

11. A metalloproteinase inhibitor which contains a compound of claim 1 as an active ingredient.

12. A matrix metalloproteinase inhibitor which contains a compound of claim 1 as an active ingredient.

13. A compound of claim 2, wherein $R^6$ is a group represented by the formula:

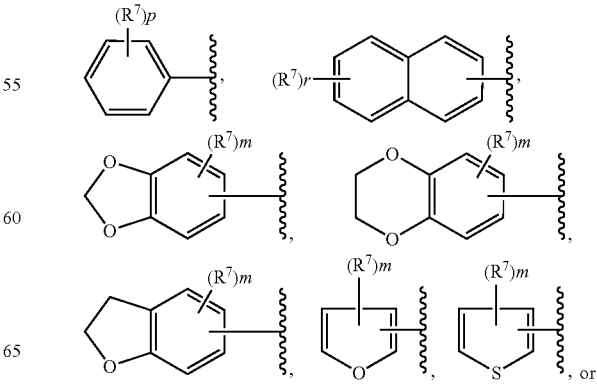

-continued

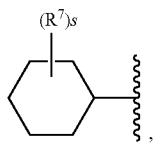

wherein R⁷ is each independently halogen, lower alkyl, cycloalkyl, lower alkenyl, lower alkynyl, lower alkyloxy, lower alkenyloxy, lower alkylthio, halo(lower)alkyl, halo(lower)alkyloxy, halo(lower)alkylthio, hydroxy, hydroxy(lower)alkyl, carboxy, lower alkyloxycarbonyl, lower alkylsulfonyl, carbamoyl, acyl, acyloxy, nitro, cyano, optionally substituted amino, or optionally substituted aminocarbonyl; m is an integer from 0 to 3; n is an integer from 0 to 4; p is an integer from 0 to 5; q is an integer from 0 to 6; r is an integer from 0 to 7; s is an integer from 0 to 11, its optically active substance, their pharmaceutically acceptable salt, or a solvate thereof.

* * * * *